US008569310B2

(12) United States Patent
Iserloh et al.

(10) Patent No.: US 8,569,310 B2
(45) Date of Patent: Oct. 29, 2013

(54) PENTAFLUOROSULFUR IMINO HETEROCYCLIC COMPOUNDS AS BACE-1 INHIBITORS, COMPOSITIONS AND THEIR USE

(75) Inventors: Ulrich Iserloh, Hoboken, NJ (US); Andrew W. Stamford, Chatham, NJ (US); Jared N Cumming, Garwood, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/391,441

(22) PCT Filed: Oct. 6, 2010

(86) PCT No.: PCT/US2010/051558
§ 371 (c)(1),
(2), (4) Date: Feb. 21, 2012

(87) PCT Pub. No.: WO2011/044185
PCT Pub. Date: Apr. 14, 2011

(65) Prior Publication Data
US 2012/0195881 A1    Aug. 2, 2012

Related U.S. Application Data

(60) Provisional application No. 61/249,686, filed on Oct. 8, 2009.

(51) Int. Cl.
*A01N 43/54* (2006.01)
*C07D 239/42* (2006.01)
*C07D 401/04* (2006.01)

(52) U.S. Cl.
USPC ............................ 514/256; 544/330; 544/331

(58) Field of Classification Search
USPC .................................. 514/256; 544/330, 331
See application file for complete search history.

(56) References Cited

U.S. PATENT DOCUMENTS

| 5,534,520 | A  | 7/1996  | Fisher et al. |
| 6,683,091 | B2 | 1/2004  | Asberom et al. |
| 7,648,983 | B2 | 1/2010  | Audia et al. |
| 7,994,167 | B2 | 8/2011  | Frank et al. |
| 8,338,413 | B1 | 12/2012 | Rueeger |
| 2006/0034848 | A1 | 2/2006 | Kinoshita et al. |
| 2007/0072925 | A1 | 3/2007 | Malamas et al. |
| 2007/0287692 | A1* | 12/2007 | Wu et al. .................. 514/210.02 |
| 2007/0299087 | A1 | 12/2007 | Berg et al. |
| 2009/0023762 | A1 | 1/2009 | Berg et al. |
| 2009/0062282 | A1 | 3/2009 | Albert et al. |
| 2010/0075957 | A1 | 3/2010 | Tamura et al. |
| 2011/0009395 | A1 | 1/2011 | Audia et al. |
| 2011/0046122 | A1 | 2/2011 | Andreini et al. |
| 2012/0148603 | A1* | 6/2012 | Stamford et al. .......... 424/172.1 |
| 2012/0183563 | A1* | 7/2012 | Scott et al. ................. 424/172.1 |
| 2012/0184540 | A1 | 7/2012 | Andreini et al. |
| 2012/0189642 | A1* | 7/2012 | Scott et al. ................. 424/172.1 |
| 2012/0196863 | A1 | 8/2012 | Andreini et al. |
| 2012/0258961 | A1 | 10/2012 | Suzuki et al. |
| 2012/0258962 | A1 | 10/2012 | Hilpert et al. |
| 2012/0302549 | A1 | 11/2012 | Narquizian et al. |

FOREIGN PATENT DOCUMENTS

| EP | 1942105 | 7/2008 |
| JP | 2012250933 | 12/2012 |
| WO | WO9004197 | 5/1990 |
| WO | WO9304047 | 3/1993 |
| WO | WO 0051992 A1 * | 9/2000 |
| WO | WO03097641 | 11/2003 |
| WO | WO2005014540 | 2/2005 |
| WO | WO2005016876 | 2/2005 |
| WO | WO2005058311 | 6/2005 |
| WO | WO2006009653 | 1/2006 |

(Continued)

OTHER PUBLICATIONS

S. Stachel et al., 47 Journal of Medicinal Chemistry 6447-6450 (2004).*

(Continued)

*Primary Examiner* — James O Wilson
*Assistant Examiner* — Alexander R Pagano
(74) *Attorney, Agent, or Firm* — Keith D. MacMillan; John C. Todaro

(57) ABSTRACT

In its many embodiments, the present invention provides certain pentafluorosulfur imino heterocyclic compounds, including compounds Formula (a) and pharmaceutically acceptable salts thereof. Compounds of Formula (a) have the general structure: (a) wherein each variable is selected independently and as defined herein. Pharmaceutical compositions comprising one or more such compounds (alone and in combination with one or more other active agents), and methods for their preparation and use in treating pathologies associated with amyloid beta (Aβ) protein, including Alzheimers Disease, are also disclosed.

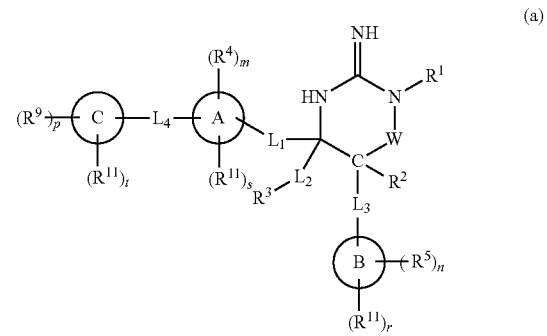

16 Claims, No Drawings

(56) References Cited

FOREIGN PATENT DOCUMENTS

| | | |
|---|---|---|
| WO | WO2006014762 | 2/2006 |
| WO | WO2006014944 | 2/2006 |
| WO | WO2006041404 | 4/2006 |
| WO | WO2006041405 | 4/2006 |
| WO | WO2006065277 | 6/2006 |
| WO | WO2006138192 | 12/2006 |
| WO | WO2006138195 | 12/2006 |
| WO | WO2006138217 | 12/2006 |
| WO | WO2006138230 | 12/2006 |
| WO | WO2006138264 | 12/2006 |
| WO | WO2006138265 | 12/2006 |
| WO | WO2006138266 | 12/2006 |
| WO | WO2007005366 | 1/2007 |
| WO | WO2007005404 | 1/2007 |
| WO | WO2007016012 | 2/2007 |
| WO | WO2007038271 | 4/2007 |
| WO | WO2007049532 | 5/2007 |
| WO | WO2007050721 | 5/2007 |
| WO | WO2007053506 | 5/2007 |
| WO | WO2007058580 | 5/2007 |
| WO | WO2007058581 | 5/2007 |
| WO | WO2007073284 | 6/2007 |
| WO | WO2007093621 | 8/2007 |
| WO | WO2007114771 | 10/2007 |
| WO | WO2007145568 | 12/2007 |
| WO | WO2007145569 | 12/2007 |
| WO | WO2007145570 | 12/2007 |
| WO | WO2007145571 | 12/2007 |
| WO | WO2007146225 | 12/2007 |
| WO | WO2007149033 | 12/2007 |
| WO | WO2008073365 | 6/2008 |
| WO | WO2008073370 | 6/2008 |
| WO | WO2008076045 | 6/2008 |
| WO | WO2008076046 | 6/2008 |
| WO | WO2008133273 | 6/2008 |
| WO | WO2008133274 | 6/2008 |
| WO | WO2008103351 | 8/2008 |
| WO | WO2009005470 | 1/2009 |
| WO | WO2009091016 | 7/2009 |
| WO | WO2009131974 | 10/2009 |
| WO | WO2009131975 | 10/2009 |
| WO | WO2009134617 | 11/2009 |
| WO | WO2009151098 | 12/2009 |
| WO | WO2010021680 | 2/2010 |
| WO | WO2010038686 | 4/2010 |
| WO | WO2010047372 | 4/2010 |
| WO | WO2010048149 | 4/2010 |
| WO | WO2010063718 | 6/2010 |
| WO | WO2010113848 | 10/2010 |
| WO | WO2011005738 | 1/2011 |
| WO | WO2011009897 | 1/2011 |
| WO | WO2011009898 | 1/2011 |
| WO | WO2011009943 | 1/2011 |
| WO | WO2011020806 | 2/2011 |
| WO | WO2011044181 | 4/2011 |
| WO | WO2011044184 | 4/2011 |
| WO | WO2011044185 | 4/2011 |
| WO | WO2011044187 | 4/2011 |
| WO | WO2011058763 | 5/2011 |
| WO | WO2011069934 | 6/2011 |
| WO | WO2011070781 | 6/2011 |
| WO | WO2011071057 | 6/2011 |
| WO | WO2011071109 | 6/2011 |
| WO | WO2011071135 | 6/2011 |
| WO | WO2011077726 | 6/2011 |
| WO | WO2011700029 | 6/2011 |
| WO | WO2011/142716 | 11/2011 |
| WO | WO2011154431 | 12/2011 |
| WO | WO2012006953 | 1/2012 |
| WO | WO2012147762 | 1/2012 |
| WO | WO2012147763 | 1/2012 |
| WO | WO2012057247 | 5/2012 |
| WO | WO2012057248 | 5/2012 |
| WO | WO2012095451 | 7/2012 |
| WO | WO2012095463 | 7/2012 |
| WO | WO2012095469 | 7/2012 |
| WO | WO2012095521 | 7/2012 |
| WO | WO2012098213 | 7/2012 |
| WO | WO2012098461 | 7/2012 |
| WO | WO2012138590 | 10/2012 |
| WO | WO2012138734 | 10/2012 |
| WO | WO2012139425 | 10/2012 |
| WO | WO2012139993 | 10/2012 |
| WO | WO2012156284 | 11/2012 |
| WO | WO2012168164 | 12/2012 |
| WO | WO2012168175 | 12/2012 |
| WO | WO2013028670 | 2/2013 |

OTHER PUBLICATIONS

CAPLUS Abstract of JP 2012250933 (Accession Number: 2012:1853414) (2012).*

Abramov, et al., Amyloid—as a positive endogenous regulator of release probability at hippocampal synapses, Nature Neuroscience 12, 1567-1576 (2009) Published online: Nov. 22, 2009 | doi:10.1038/nn.2433.

Barton, et al., On the Structure of Some Substituted 4, 6-Pyrimidinones, Department of Organic Chemistry, College of Medicine, Jagiellonian University, Ingardena 3, 30-060-Krakow, Poland, Polish J. Chem., 69, 235-245 (1995), revised manuscript Oct. 25, 1994.

Cho, et al, S-Nitrosylation of Drp1 Mediates β-Amyloid-Related Mitochondrial Fission and Neuronal Injury, Science Apr. 3, 2009: vol. 324 No. 5923 pp. 102-105.

Cole, et al., Review: The Alzheimer's disease B-secretase enzyme, BACEI, , Molecular Neurodegeneration 2007, 2:22, Published Nov. 15, 2007.

European Search Report and Supplementary European Search Report and Opinion for EP10822567.3, Feb. 21, 2013.

European Search Report and Supplementary European Search Report and Opinion for EP2485591, Feb. 4, 2013.

European Search Report and Supplementary European Search Report and Opinion for EP2485590, Apr. 12, 2013.

Farah, et al., Reduced BACE1 Activity Enhances Clearance of Myelin Debris and Regeneration of Axons in the Injured Peripheral Nervous System, The Journal of Neuroscience, Apr. 13, 2011 • 31(15):5744-5754.

Getchell, et al., 3-Nitrotyrosine immunoreactivity in olfactory receptor neurons of patients with Alzheimer's disease: implications for impaired odor sensitivity, Neurobiology of Aging 24 (2003) 663-673., accepted Oct. 8, 2002, pp. 663-673.

Guo, et al., Targeting Amyloid-B in Glaucoma Treatment, pp. 13444-13449, PNAS, Aug. 14, 2007, vol. 104,No. 33.

Loane, et al., Amyloid Precursor Protein Secretases as Therapeutic Targets for Traumatic Brain Injury, Nature Medicine, Advance Online Publication, Received Aug. 27, 2008; accepted Feb. 18, 2009; published online Mar. 15, 2009; doi:10.1038/nm.1940, pp. 1-3.

Luo, et al., mice deficient in BACE1, the Alzheimer's B-secretase, have normal phenotype and abolished B-amyloid, Nature Neuroscience, vol. 4, No. 3, Mar. 2001.

McConlogue, et al., Partial reduction of BACE1 as dramatic effects on Alzheimer's plaque and synaptic pathology in APP transgenic mice, J. Biological Chem., vol. 282, No. 36, pp. 26326-26334, Sep. 7, 2007.

PCT Search Report for International Application WO2011044187, Apr. 14, 2011.

PCT Written Opinion for International Application WO2011044187, Apr. 8, 2012.

PCT Search Report for International Application WO2011/044181, Apr. 14, 2011.

PCT Written Opinion for International Application WO2011/044181, Apr. 8, 2012.

European Search Report and Supplementary European Search Report and Opinion for EP2485920, mailed Mar. 25, 2013.

PCT Search Report for International Application WO2011044185, Apr. 30, 2012.

PCT Written Opinion for International Application WO2011044185, Apr. 30, 2012.

(56) References Cited

OTHER PUBLICATIONS

PCT Search Report for International Application WO2011044184, Apr. 14, 2011.

PCT Written Opinion for International Application WO2011044184, Apr. 8, 2012.

Ohno, et al., BACE1 deficiency rescues memory deficits and Cholinergic function in a mouse model of Alzheimer's disease, Neuron, vol. 41, 27-33, Jan. 8, 2004.

Ohno, et al. BACE1 gene deletion prevents neuron loss and memory deficits in 5XFAD APP/PS1 transgenic mice, Neurobiology of disease 26 (2006), pp. 134-145.

Osherovich, L. AB's Dry (AMD) Humor, SciBX 4(26); doi:10.1038/scibx.2011.727, Published online Jun. 30, 2011.

Roberds, et al., BACE knockout mice are healthy despite lacking the primary B-secretase activity in the brain: implications for Alzheimer's disease therapeutics, Human Mol. Genetics, vol. 10, No. 12, pp. 1317-1324. Apr. 3, 2004.

Solloway, et al., A randomized, double-blind, placebo-controlled clinical trial of intravenous bapineuzumab in patients with mild-to-moderate Alzheimer's disease who are alipoprotein E4 non-carriers, European Federation of Neurological Societies, Stockholm, Sweden, Sep. 12, 2012.

Sperling, et al., A randomized, double-blind, placebo-controlled clinical trial of intravenous bapineuzumab in patients with mild-to-moderate Alzheimer's disease who are alipoprotein E4 non-carriers, European Federation of Neurological Societies, Stockholm, Sweden, Sep. 11, 2012.

Stachel, et al., Structure-Based Design of Potent and Selective Cell-Permeable Inhibitors of Human Beta-Secretase (BACE-1), J. Med. Chem., 2004, vol. 47, pp. 6447-6450.

Weiner, Further insights into Alzheimer disease pathogenesis, Weiner, M. W. Nat. Rev. Neurol. 9, 65-66 (2013); published online Jan. 22, 2013.

Welch, J.T., et al., The synthesis and biological activity of pentafluorosulfanyl analogs of fluoxetine, fenfluramine, and norfenfluramine , Bioorganic & Medicinal Chemistry; v:15 i:21 p. 6659-6666; Nov. 1, 2007.

Copending U.S. Appl. No. 13/392,955, Imino Thiadiazine Dioxide Compounds As BACE-1 Inhibitors, Compositions, and Their Use, filed Oct. 6, 2010.

Copending U.S. Appl. No. 13/392,297, Imino Thiadiazine Dioxide Compounds As BACE-1 Inhibitors, Compositions, and Their Use, filed Oct. 6, 2010.

Copending U.S. Appl. No. 13/390,856, Afluorosulfur Imino Heterocyclic Compounds As BACE-1 Inhibitors, Compositions, and Their Use, U.S. Appl. No. 13/390,856.

* cited by examiner

PENTAFLUOROSULFUR IMINO HETEROCYCLIC COMPOUNDS AS BACE-1 INHIBITORS, COMPOSITIONS AND THEIR USE

CROSS REFERENCE TO RELATED APPLICATIONS

This application is the national stage application filed under 37 U.S.C. 371 based on International Patent Application No PCT/US2010/051558, filed on Oct. 06, 2010, which claims priority to U.S. Provisional Application No. 61/249,686 filed on Oct. 08, 2009, each of which is incorporated by reference.

FIELD OF THE INVENTION

This invention provides certain pentafluorosulfur imino heterocyclic compounds and compositions comprising these compounds. The pentafluorosulfur imino heterocyclic compounds and compositions of the invention are useful as BACE-1 inhibitors and for the treatment and prevention of various pathologies related to β-amyloid ("Aβ") production.

BACKGROUND

Amyloid beta peptide ("Aβ") is a primary component of β amyloid fibrils and plaques, which are regarded as a causative feature in an increasing number of pathologies. Examples of such pathologies include, but are not limited to, Alzheimer's Disease, Down's syndrome, Parkinson's disease, memory loss (including memory loss associated with Alzheimer's disease and Parkinson's disease), attention deficit symptoms (including attention deficit symptoms associated with Alzheimer's disease ("AD"), Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration, neurodegeneration, olfactory impairment (including olfactory impairment associated with Alzheimer's disease, Parkinson's disease, and Down's syndrome), β-amyloid angiopathy (including cerebral amyloid angiopathy), hereditary cerebral hemorrhage, mild cognitive impairment ("MCI"), glaucoma, amyloidosis, type II diabetes, hemodialysis ($β_2$ microglobulins and complications arising therefrom), neurodegenerative diseases such as scrapie, bovine spongiform encephalitis, Creutzfeld-Jakob disease, traumatic brain injury, and the like.

Aβ peptides are short peptides which are made from the abnormal proteolytic break-down of the transmembrane protein called amyloid precursor protein ("APP"). Aβ peptides are made from the cleavage of APP by β-secretase activity at the position corresponding to the N-terminus of Aβ, and by γ-secretase activity at the position corresponding to the C-terminus of Aβ. (APP is also cleaved by α-secretase activity, resulting in the secreted, non-amyloidogenic fragment known as soluble APPα.) Beta site APP Cleaving Enzyme ("BACE-1") is regarded as the primary aspartyl protease responsible for the production of abnormal Aβ by β-secretase activity. The inhibition of BACE-1 has been shown to inhibit the production of Aβ.

Alzheimer's disease ("AD") is estimated to afflict more than 20 million people worldwide and is believed to be the most common cause of dementia. AD is a disease characterized by degeneration and loss of neurons and also by the formation of senile plaques and neurofibrillary tangles. Presently, treatment of Alzheimer's disease is limited to the treatment of its symptoms rather than the underlying causes. Symptom-improving agents approved for this purpose include, for example, N-methyl-D-aspartate receptor antagonists such as memantine (Namenda®, Forrest Pharmaceuticals, Inc.), cholinesterase inhibitors such as donepezil (Aricept®, Pfizer), rivastigmine (Exelon®, Novartis), galantamine (Razadyne Reminyl®), and tacrine (Cognex®).

In AD, Aβ peptides, abnormally formed through β-secretase and γ-secretase activity, can form tertiary structures that aggregate to form amyloid fibrils. Aβ peptides have also been shown to form Aβ oligomers (sometimes referred to as "Abeta aggregates" or "Abeta oligomers"). Aβ oligomers are small multimeric structures composed of 2 to 12 Aβ peptides that are structurally distinct from Aβ fibrils. Amyloid fibrils can deposit outside neurons in dense formations known as senile plaques, neuritic plaques, or diffuse plaques in regions of the brain important to memory and cognition. Aβ oligomers are cytotoxic when injected in the brains of rats or in cell culture. This Aβ plaque formation and deposition and/or Aβ oligomer formation, and the resultant neuronal death and cognitive impairment, are among the hallmarks of AD pathophysiology. Other hallmarks of AD pathophysiology include intracellular neurofibrillary tangles comprised of abnormally phosphorylated tau protein, and neuroinflammation.

Evidence suggests that Aβ and Aβ fibrils and plaque play a causal role in AD pathophysiology. (See Ohno et al., *Neurobiology of Disease*, No. 26 (2007), 134-145.) Mutations in the genes for APP and presenilins ½ (PS½) are known to cause familial AD and an increase in the production of the 42-amino acid form of Aβ is regarded as causative. Aβ has been shown to be neurotoxic in culture and in vivo. For example, when injected into the brains of aged primates, fibrillar Aβ causes neuron cell death around the injection site. Other direct and circumstantial evidence of the role of Aβ in Alzheimer etiology has also been published.

BACE-1 has become an accepted therapeutic target for the treatment of Alzheimer's disease. For example, McConlogue et al., *J. Bio. Chem.*, vol. 282, No. 36 (September 2007), have shown that partial reductions of BACE-1 enzyme activity and concomitant reductions of Aβ levels lead to a dramatic inhibition of Aβ-driven AD-like pathology (while minimizing potential side effects of full inhibition), making β-secretase a target for therapeutic intervention in AD. Ohno et al. *Neurobiology of Disease*, No. 26 (2007), 134-145, report that genetic deletion of BACE-1 in 5XFAD mice abrogates Aβ generation, blocks amyloid deposition, prevents neuron loss found in the cerebral cortex and subiculum (brain regions manifesting the most severe amyloidosis in 5XFAD mice), and rescues memory deficits in 5XFAD mice. The group also reports that Aβ is ultimately responsible for neuron death in AD and conclude that BACE-1 inhibition has been validated as an approach for the treatment of AD. Roberds et al., *Human Mol. Genetics*, 2001, Vol. 10, No. 12, 1317-1324, established that inhibition or loss of β-secretase activity produces no profound phenotypic defects while inducing a concomitant reduction in β-amyloid peptide. Luo et al., *Nature Neuroscience*, vol. 4, no. 3, March 2001, report that mice deficient in BACE-1 have normal phenotype and abolished β-amyloid generation.

BACE-1 has also been identified or implicated as a therapeutic target for a number of other diverse pathologies in which Aβ or Aβ fragments have been identified to play a causative role. One such example is in the treatment of AD-type symptoms of patients with Down's syndrome. The gene encoding APP is found on chromosome 21, which is also the chromosome found as an extra copy in Down's syndrome. Down's syndrome patients tend to acquire AD at an early age, with almost all those over 40 years of age showing Alzheimer's-type pathology. This is thought to be due to the extra copy of the APP gene found in these patients, which leads to overexpression of APP and therefore to increased levels of Aβ causing the prevalence of AD seen in this population. Furthermore, Down's patients who have a duplication of a small region of chromosome 21 that does not include the APP gene do not develop AD pathology. Thus, it is thought that inhibitors of BACE-1 could be useful in reducing Alzheimer's type pathology in Down's syndrome patients.

Another example is in the treatment of glaucoma (Guo et al., *PNAS*, vol. 104, no. 33, Aug. 14, 2007). Glaucoma is a retinal disease of the eye and a major cause of irreversible blindness worldwide. Guo et al. report that Aβ colocalizes with apoptotic retinal ganglion cells (RGCs) in experimental glaucoma and induces significant RGC cell loss in vivo in a dose- and time-dependent manner. The group report having demonstrated that targeting different components of the Aβ formation and aggregation pathway, including inhibition of β-secretase alone and together with other approaches, can effectively reduce glaucomatous RGC apoptosis in vivo. Thus, the reduction of Aβ production by the inhibition of BACE-1 could be useful, alone or in combination with other approaches, for the treatment of glaucoma.

Another example is in the treatment of olfactory impairment. Getchell et al., *Neurobiology of Aging*, 24 (2003), 663-673, have observed that the olfactory epithelium, a neuroepithelium that lines the posterior-dorsal region of the nasal cavity, exhibits many of the same pathological changes found in the brains of AD patients, including deposits of Aβ, the presence of hyperphosphorylated tau protein, and dystrophic neurites among others. Other evidence in this connection has been reported by Bacon A W, et al., *Ann NY Acad Sci* 2002; 855:723-31; Crino P B, Martin J A, Hill W D, et al., *Ann Otol Rhinol Laryngol*, 1995; 104:655-61; Davies D C, et al., *Neurobiol Aging*, 1993; 14:353-7; Devanand D P, et al., *Am J Psychiatr*, 2000; 157:1399-405; and Doty R L, et al., *Brain Res Bull*, 1987; 18:597-600. It is reasonable to suggest that addressing such changes by reduction of Aβ by inhibition of BACE-1 could help to restore olfactory sensitivity in patients with AD.

Other diverse pathologies characterized by the inappropriate formation and deposition of Aβ or fragments thereof, and/or by the presence of amyloid fibrils, include neurodegenerative diseases such as scrapie, bovine spongiform encephalitis, Creutzfeld-Jakob disease and the like, type II diabetes (which is characterized by the localized accumulation of cytotoxic amyloid fibrils in the insulin producing cells of the pancreas), and amyloid angiopathy. In this regard reference can be made to the patent literature. For example, Kong et al., US2008/0015180, disclose methods and compositions for treating amyloidosis with agents that inhibit Aβ peptide formation. As another example, Loane, et al. report the targeting of amyloid precursor protein secretases as therapeutic targets for traumatic brain injury. (Loane et al., "Amyloid precursor protein secretases as therapeutic targets for traumatic brain injury", *Nature Medicine, Advance Online Publication*, published online Mar. 15, 2009.)

Still other diverse pathologies characterized by the inappropriate formation and deposition of Aβ or fragments thereof, and/or by the presence of amyloid fibrils, and/or for which inhibitor(s) of BACE-1 is expected to be of therapeutic value are discussed further hereinbelow.

The therapeutic potential of inhibiting the deposition of Aβ has motivated many groups to characterize BACE-1 and to identify BACE-1 and other secretase enzyme inhibitors. Examples from the patent literature are growing and include WO2006009653, WO2007005404, WO2007005366, WO2007038271, WO2007016012, US2005/0282826, US2007072925, WO2007149033, WO2007145568, WO2007145569, WO2007145570, WO2007145571, WO2007114771, US20070299087, WO2005/016876, WO2005/014540, WO2005/058311, WO2006/065277, WO2006/014762, WO2006/014944, WO2006/138195, WO2006/138264, WO2006/138192, WO2006/138217, WO2007/050721, WO2007/053506, WO2007/146225, WO2006/138230, WO2006/138265, WO2006/138266, WO2007/053506, WO2007/146225, WO2008/073365, WO2008/073370, WO2008/103351, US2009/041201, and US2009/041202.

SUMMARY OF THE INVENTION

The present invention provides certain pentafluorosulfur imino heterocyclic compounds which are collectively or individually referred to herein as "compound(s) of the invention", as described herein.

In each of the various embodiments of the compounds of the invention described herein, including those of Formulas (a), (I), (IA), (IA-1), and (IA-2), (II), (IIA), (IIA-1), and (IIA-2), and the various embodiments thereof, each variable is selected independently of each others unless otherwise indicated.

In each of the various embodiments of the compounds of the invention described herein, including those of Formulas (a), (I), (IA), (IA-1), and (IA-2), (II), (IIA), (IIA-1), and (IIA-2), and the various embodiments thereof and the compounds of the examples, such formulas and examples are intended to encompass all forms of the compounds such as, for example, any solvates, hydrates, stereoisomers, and tautomers of said compounds and of any pharmaceutically acceptable salts thereof.

In one embodiment, the compounds of the invention have the structural Formula (a):

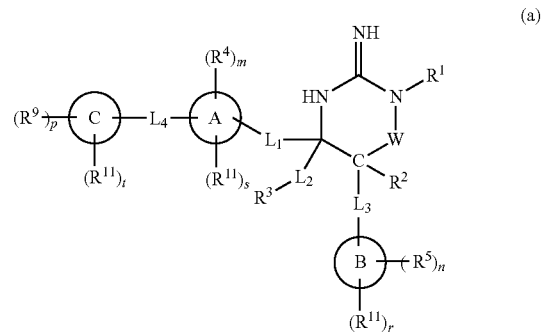

wherein:

W is selected from the group consisting of —C(O)—, —C(S)—, and —C(=NR$^{8A}$)—;

-L$_1$- is present or absent and when present represents a divalent moiety selected from the group consisting of -alkyl-, -haloalkyl-, -heteroalkyl-, -alkenyl-, and -alkynyl-;

-L$_2$- is present or absent and when present represents a divalent moiety selected from the group consisting of -alkyl-, -haloalkyl-, -heteroalkyl-, -alkenyl-, and -alkynyl-;

-L$_3$- is present or absent and when present represents a divalent moiety selected from the group consisting of -alkyl-, -haloalkyl-, -heteroalkyl-, -alkenyl-, and -alkynyl-;

each -L$_4$- (when present) independently is present or absent and when present represents a divalent moiety independently selected from the group consisting of -alkyl-, -haloalkyl-, -heteroalkyl-, -alkenyl-, -alkynyl-, —N($R^8$)—, —NHC(O)—, and —C(O)NH—;

m, n, p, q, r, s, and t are each independently selected integers, wherein:
m is 0 or more,
n is 0 or more,
p is 0 or more,
q is 0 or more,
r is 0, 1, or 2,
s is 0, 1, or 2,
t is 0, 1, or 2,
with the provisos that:
(i) the maximum value of the sum of m, q, and s is the maximum number of available substitutable hydrogen atoms on ring A,
(ii) the maximum value of the sum of n and r is the maximum number of available substitutable hydrogen atoms on ring B, and
(iii) the maximum value of the sum of p and t is the maximum number of available substitutable hydrogen atoms on ring C, and
(iv) the sum of r, s, and t is 1 or 2;

$R^1$ is selected from the group consisting of: H, alkyl, haloalkyl, heteroalkyl, heterohaloalkyl, cycloalkyl, cycloalkylalkyl-, heterocycloalkyl, heterocycloalkylalkyl-, aryl, arylalkyl-, heteroaryl, and heteroarylalkyl-,
wherein each of said alkyl, haloalkyl, heteroalkyl, heterohaloalkyl, cycloalkyl, cycloalkylalkyl-, heterocycloalkyl, heterocycloalkylalkyl-, aryl, arylalkyl-, heteroaryl, and heteroarylalkyl- of $R^1$ is unsubstituted or substituted with from 1 to 5 independently selected $R^{10}$ groups;

$R^2$ is selected from the group consisting of H, alkyl, halo, haloalkyl, aryl, arylalkyl-, heteroaryl, heteroarylalkyl-, cycloalkyl, cycloalkylalkyl-, cycloalkenyl, heterocycloalkyl, and heterocycloalkenyl,
wherein each of said alkyl, haloalkyl, aryl, arylalkyl-, heteroaryl, heteroarylalkyl-, cycloalkyl, cycloalkylalkyl-, cycloalkenyl, heterocycloalkyl, and heterocycloalkenyl of $R^2$ is unsubstituted or substituted with from 1 to 5 independently selected $R^{10}$ groups;

$R^3$ is selected from the group consisting of alkyl, aryl, heteroaryl, cycloalkyl, cycloalkenyl, heterocycloalkyl, and heterocycloalkenyl,
wherein each of said alkyl, aryl, heteroaryl, cycloalkyl, cycloalkenyl, heterocycloalkyl, and heterocycloalkenyl of $R^3$ is unsubstituted or substituted with from 1 to 5 independently selected $R^{10}$ groups;

ring A is selected from the group consisting of monocyclic aryl, monocyclic heteroaryl, monocyclic cycloalkyl, monocyclic cycloalkenyl, monocyclic heterocycloalkyl, monocyclic heterocycloalkenyl, and a multicyclic group;

each $R^4$ (when present) is independently selected from the group consisting of halo, —CN, —$NO_2$, —Si($R^6$)$_3$, —P(O)(O$R^7$)$_2$, —P(O)(O$R^7$)($R^7$), —N($R^8$)$_2$, —$NR^8$C(O)$R^7$, —$NR^8$S(O)$_2R^7$, —$NR^8$C(O)N($R^8$)$_2$, —$NR^8$C(O)O$R^7$, —C(O)$R^7$, —C(O)$_2R^7$, —C(O)N($R^8$)$_2$, —S(O)$R^7$, —S(O)$_2R^7$, —S(O)$_2$N($R^8$)$_2$, —O$R^7$, —S$R^7$, alkyl, haloalkyl, haloalkoxy, heteroalkyl, alkenyl, alkynyl, cycloalkyl, cycloalkylalkyl-, heterocycloalkyl, aryl, and heteroaryl,
wherein each said alkyl, haloalkyl, haloalkoxy, heteroalkyl, alkenyl, alkynyl, cycloalkyl, cycloalkylalkyl-, heterocycloalkyl, aryl, and heteroaryl of $R^4$ (when present) is optionally independently unsubstituted or further substituted with one or more independently selected groups selected from the group consisting of lower alkyl, lower alkenyl, lower alkynyl, lower heteroalkyl, halo, —CN, —$SF_5$, —$OSF_5$, —$NO_2$, —N($R^8$)$_2$, —O$R^7$, —C(O)N($R^8$)$_2$, and cycloalkyl;

ring B is selected from the group consisting of monocyclic aryl, monocyclic heteroaryl, monocyclic cycloalkyl, monocyclic cycloalkenyl, monocyclic heterocycloalkyl, monocyclic heterocycloalkenyl, and a multicyclic group;

each $R^5$ (when present) is independently selected from the group consisting of halo, —CN, —$NO_2$, —Si($R^6$)$_3$, —P(O)(O$R^7$)$_2$, —(O)(O$R^7$)($R^7$), —N($R^8$)$_2$, —$NR^8$C(O)$R^7$, —$NR^8$S(O)$_2R^7$, —$NR^8$C(O)N($R^8$)$_2$, —$NR^8$C(O)O$R^7$, —C(O)$R^7$, —C(O)$_2R^7$, —C(O)N($R^8$)$_2$, —S(O)$R^7$, —S(O)$_2R^7$, —S(O)$_2$N($R^8$)$_2$, —O$R^7$, —S$R^7$, alkyl, haloalkyl, haloalkoxy, heteroalkyl, alkenyl, alkynyl, cycloalkyl, cycloalkylalkyl-, heterocycloalkyl, aryl, and heteroaryl,
wherein each said alkyl, haloalkyl, haloalkoxy, heteroalkyl, alkenyl, alkynyl, cycloalkyl, cycloalkylalkyl-, heterocycloalkyl, aryl, and heteroaryl of $R^5$ (when present) is optionally independently unsubstituted or further substituted with one or more independently selected groups selected from the group consisting of lower alkyl, lower alkenyl, lower alkynyl, lower heteroalkyl, halo, —CN, —$SF_5$, —$OSF_5$, —$NO_2$, —N($R^8$)$_2$, —O$R^7$, —C(O)N($R^8$)$_2$, and cycloalkyl;

each ring C (when present) is independently selected from the group consisting of monocyclic aryl, monocyclic heteroaryl, monocyclic cycloalkyl, monocyclic cycloalkenyl, monocyclic heterocycloalkyl, monocyclic heterocycloalkenyl, and a multicyclic group;

each $R^6$ (when present) is independently selected from the group consisting of alkyl, aryl, arylalkyl-, haloalkyl, cycloalkyl, cycloalkylalkyl-, heteroaryl, and heteroarylalkyl-;

each $R^7$ (when present) is independently selected from the group consisting of H, alkyl, alkenyl, heteroalkyl, haloalkyl, aryl, arylalkyl-, heteroaryl, heteroarylalkyl-, cycloalkyl, cycloalkylalkyl-, heterocycloalkyl, and heterocycloalkylalkyl-;

each $R^8$ (when present) is independently selected from the group consisting of H, alkyl, alkenyl, heteroalkyl, haloalkyl, aryl, arylalkyl-, heteroaryl, heteroarylalkyl-, cycloalkyl, cycloalkylalkyl-, heterocycloalkyl, and heterocycloalkylalkyl-;

$R^{8.4}$ is selected from the group consisting of alkyl, alkenyl, cycloalkyl, cycloalkylalkyl, heterocycloalkyl, heterocycloalkylalkyl, aryl, arylalkyl, heteroaryl, heteroarylalkyl, arylcycloalkyl, O$R^7$, —CN, —C(O)$R^7$, —C(O)O$R^7$, —S(O)$_2R^7$, —C(O)N($R^8$)$_2$, —S(O)N($R^8$)$_2$, —S(O)$_2$N($R^8$)$_2$, —$NO_2$, and —N($R^8$)$_2$;

each $R^9$ (when present) is independently selected from the group consisting of: halogen, —CN, —$NO_2$, —Si($R^6$)$_3$, —P(O)(O$R^7$)$_2$, —P(O)(O$R^7$)($R^7$), —N($R^8$)$_2$, —$NR^8$C(O)$R^7$, —$NR^8$S(O)$_2R^7$, —$NR^8$C(O)N($R^8$)$_2$, —$NR^8$C(O)O$R^7$, —C(O)$R^7$, —C(O)$_2R^7$, —C(O)N($R^8$)$_2$, —S(O)$R^7$, —S(O)$_2R^7$, —S(O)$_2$N($R^8$)$_2$, —O$R^7$, —S$R^7$, alkyl, haloalkyl, heteroalkyl, alkenyl, alkynyl, aryl, arylalkyl-, cycloalkyl, heteroaryl, heteroarylalkyl-, and heterocycloalkyl;

each $R^{10}$ (when present) is independently selected from the group consisting of halo, —CN, —$NO_2$, —Si($R^6$)$_3$, —P(O)(O$R^7$)$_2$, —P(O)(O$R^7$)($R^7$), —N($R^5$)$_2$, —$NR^8$C(O)$R^7$, —$NR^8$S(O)$_2R^7$, —$NR^8$C(O)N($R^8$)$_2$, —$NR^8$C(O)O$R^7$, —C(O)$R^7$, —C(O)$_2R^7$, —C(O)N($R^8$)$_2$, —S(O)$R^7$, —S(O)$_2R^7$, —S(O)$_2$N($R^8$)$_2$, —O$R^7$, —S$R^7$, alkyl, haloalkyl, haloalkoxy, heteroalkyl, alkenyl, alkynyl, cycloalkyl, heterocycloalkyl, aryl, and heteroaryl,
wherein each said alkyl, haloalkyl, haloalkoxy, heteroalkyl, alkenyl, alkynyl, cycloalkyl, heterocycloalkyl, aryl, and heteroaryl of $R^{10}$ (when present) is optionally independently unsubstituted or further substituted with one or more independently selected groups selected from the group consisting of lower alkyl, lower alkenyl, lower alkynyl, lower heteroalkyl, halo, —CN, —NO$_2$, —N(R$^8$)$_2$, —OR$^7$, —C(O)N(R$^8$)$_2$, and cycloalkyl; and each $R^{11}$ is independently selected from the group consisting of —SF$_5$ and —OSF$_5$.

In other embodiments, the invention provides various methods of treating, preventing, ameliorating, and/or delaying the onset of an amyloid β pathology (Aβ pathology) and/or a symptom or symptoms thereof, comprising administering a composition comprising an effective amount of one or more compounds of the invention, or a tautomer thereof, or pharmaceutically acceptable salt or solvate of said compound(s) and/or said tautomer(s), to a patient in need thereof. Such methods optionally additionally comprise administering an effective amount of one or more additional therapeutic agents suitable for treating the patient being treated.

These and other embodiments of the invention, which are described in detail below or will become readily apparent to those of ordinary skill in the art, are included within the scope of the invention.

DETAILED DESCRIPTION

In one embodiment, the compounds of the invention have the structural Formula (a) as described above.

In one embodiment, in Formula (a), q is 0 or 1.
In one embodiment, in Formula (a), q is 1;
In one embodiment, in Formula (a), q is 0 and the compounds of Formula (a) have a structure according to Formula (I):

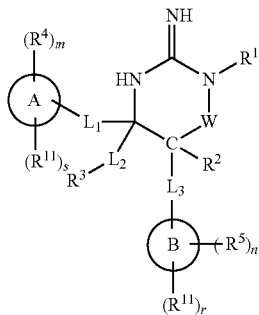

(I)

wherein:
W is selected from the group consisting of —C(O)—, —C(S)—, and —C(=NR$^{8A}$)—;
-L$_1$- is present or absent and when present represents a divalent moiety selected from the group consisting of -alkyl-, -haloalkyl-, -heteroalkyl-, -alkenyl-, and -alkynyl-;
-L$_2$- is present or absent and when present represents a divalent moiety selected from the group consisting of -alkyl-, -haloalkyl-, -heteroalkyl-, -alkenyl-, and -alkynyl-;
-L$_3$- is present or absent and when present represents a divalent moiety selected from the group consisting of -alkyl-, -haloalkyl-, -heteroalkyl-, -alkenyl-, and -alkynyl-;
m, n, r, and s are each independently selected integers, wherein:
m is 0 or more,
n is 0 or more,
r is 0, 1, or 2,
s is 0, 1, or 2, with the provisos that:
(i) the maximum value of the sum of m and s is the maximum number of available substitutable hydrogen atoms on ring A,
(ii) the maximum value of the sum of n and r is the maximum number of available substitutable hydrogen atoms on ring B, and
(iii) the sum of r and s is 1 or 2;

$R^1$ is selected from the group consisting of: H, alkyl, haloalkyl, heteroalkyl, heterohaloalkyl, cycloalkyl, cycloalkylalkyl-, heterocycloalkyl, heterocycloalkylalkyl-, aryl, arylalkyl-, heteroaryl, and heteroarylalkyl-,
wherein each of said alkyl, haloalkyl, heteroalkyl, heterohaloalkyl, cycloalkyl, cycloalkylalkyl-, heterocycloalkyl, heterocycloalkylalkyl-, aryl, arylalkyl-, heteroaryl, and heteroarylalkyl- of $R^1$ is unsubstituted or substituted with from 1 to 5 independently selected $R^{10}$ groups;

$R^2$ is selected from the group consisting of H, alkyl, halo, haloalkyl, aryl, arylalkyl-, heteroaryl, heteroarylalkyl-, cycloalkyl, cycloalkylalkyl-, cycloalkenyl, heterocycloalkyl, and heterocycloalkenyl,
wherein each of said alkyl, haloalkyl, aryl, arylalkyl-, heteroaryl, heteroarylalkyl-, cycloalkyl, cycloalkylalkyl-, cycloalkenyl, heterocycloalkyl, and heterocycloalkenyl of $R^2$ is unsubstituted or substituted with from 1 to 5 independently selected $R^{10}$ groups;

$R^3$ is selected from the group consisting of alkyl, aryl, heteroaryl, cycloalkyl, cycloalkenyl, heterocycloalkyl, and heterocycloalkenyl,
wherein each of said alkyl, aryl, heteroaryl, cycloalkyl, cycloalkenyl, heterocycloalkyl, and heterocycloalkenyl of $R^3$ is unsubstituted or substituted with from 1 to 5 independently selected $R^{10}$ groups;

ring A is selected from the group consisting of monocyclic aryl, monocyclic heteroaryl, monocyclic cycloalkyl, monocyclic cycloalkenyl, monocyclic heterocycloalkyl, monocyclic heterocycloalkenyl, and a multicyclic group;

each $R^4$ (when present) is independently selected from the group consisting of halo, —CN, —NO$_2$, —Si(R$^6$)$_3$, —P(O)(OR$^7$)$_2$, —P(O)(OR$^7$)(R$^7$), —N(R$^8$)$_2$, —NR$^8$C(O)R$^7$, —NR$^8$S(O)$_2$R$^7$, —NR$^8$C(O)N(R$^8$)$_2$, —NR$^8$C(O)OR$^7$, —C(O)R$^7$, —C(O)$_2$R$^7$, —C(O)N(R$^8$)$_2$, —S(O)R$^7$, —S(O)$_2$R$^7$, —S(O)$_2$N(R$^8$)$_2$, —OR$^7$, —SR$^7$, alkyl, haloalkyl, haloalkoxy, heteroalkyl, alkenyl, alkynyl, cycloalkyl, cycloalkylalkyl-, heterocycloalkyl, aryl, and heteroaryl,
wherein each said alkyl, haloalkyl, haloalkoxy, heteroalkyl, alkenyl, alkynyl, cycloalkyl, cycloalkylalkyl-, heterocycloalkyl, aryl, and heteroaryl of $R^4$ (when present) is optionally independently unsubstituted or further substituted with one or more independently selected groups selected from the group consisting of lower alkyl, lower alkenyl, lower alkynyl, lower heteroalkyl, halo, —CN, —SF$_5$, —OSF$_5$, —NO$_2$, —N(R$^8$)$_2$, —OR$^7$, —C(O)N(R$^8$)$_2$, and cycloalkyl;

ring B is selected from the group consisting of monocyclic aryl, monocyclic heteroaryl, monocyclic cycloalkyl, monocyclic cycloalkenyl, monocyclic heterocycloalkyl, monocyclic heterocycloalkenyl, and a multicyclic group;

each $R^5$ (when present) is independently selected from the group consisting of halo, —CN, —NO$_2$, —Si(R$^6$)$_3$, —P(O)(OR$^7$)$_2$, —P(O)(OR$^7$)(R$^7$), —N(R$^8$)$_2$, —NR$^8$C(O)R$^7$, —NR$^8$S(O)$_2$R$^7$, —NR$^8$C(O)N(R$^8$)$_2$, —NR$^8$C(O)OR$^7$, —C(O)R$^7$, —C(O)$_2$R$^7$, —C(O)N(R$^8$)$_2$, —S(O)R$^7$, —S(O)$_2$R$^7$, —S(O)$_2$N(R$^8$)$_2$, —OR$^7$, —SR$^7$, alkyl, haloalkyl, haloalkoxy, heteroalkyl, alkenyl, alkynyl, cycloalkyl, cycloalkylalkyl-, heterocycloalkyl, aryl, and heteroaryl, wherein each said alkyl, haloalkyl, haloalkoxy, heteroalkyl, alkenyl, alkynyl, cycloalkyl, cycloalkylalkyl-, heterocycloalkyl, aryl, and heteroaryl of $R^5$ (when present) is optionally independently unsubstituted or further substituted with one or more independently selected groups selected from the group consisting of lower alkyl, lower alkenyl, lower alkynyl, lower heteroalkyl, halo, —CN, —SF$_5$, —OSF$_5$, —NO$_2$, —N(R$^8$)$_2$, —OR$^7$, —C(O)N(R$^8$)$_2$, and cycloalkyl;

each $R^6$ (when present) is independently selected from the group consisting of alkyl, aryl, arylalkyl-, haloalkyl, cycloalkyl, cycloalkylalkyl-, heteroaryl, and heteroarylalkyl-;

each $R^7$ (when present) is independently selected from the group consisting of H, alkyl, alkenyl, heteroalkyl, haloalkyl, aryl, arylalkyl-, heteroaryl, heteroarylalkyl-, cycloalkyl, cycloalkylalkyl-, heterocycloalkyl, and heterocycloalkylalkyl-;

each $R^8$ (when present) is independently selected from the group consisting of H, alkyl, alkenyl, heteroalkyl, haloalkyl, aryl, arylalkyl-, heteroaryl, heteroarylalkyl-, cycloalkyl, cycloalkylalkyl-, heterocycloalkyl, and heterocycloalkylalkyl-;

$R^{8A}$ is selected from the group consisting of alkyl, alkenyl, cycloalkyl, cycloalkylalkyl, heterocycloalkyl, heterocycloalkylalkyl, aryl, arylalkyl, heteroaryl, heteroarylalkyl, arylcycloalkyl, OR$^7$, —CN, —C(O)R$^7$, —C(O)OR$^7$, —S(O)$_2$R$^7$, —C(O)N(R$^8$)$_2$, —S(O)N(R$^8$)$_2$, —S(O)$_2$N(R$^8$)$_2$, —NO$_2$, and —N(R$^8$)$_2$;

each $R^{10}$ (when present) is independently selected from the group consisting of halo, —CN, —NO$_2$, —Si(R$^6$)$_3$, —P(O)(OR$^7$)$_2$, —P(O)(OR$^7$)(R$^7$), —N(R$^8$)$_2$, —NR$^8$C(O)R$^7$, —NR$^8$S(O)$_2$R$^7$, —NR$^8$C(O)N(R$^8$)$_2$, —NR$^8$C(O)OR$^7$, —C(O)R$^7$, —C(O)$_2$R$^7$, —C(O)N(R$^8$)$_2$, —S(O)R$^7$, —S(O)$_2$R$^7$, —S(O)$_2$N(R$^8$)$_2$, —OR$^7$, —SR$^7$, alkyl, haloalkyl, haloalkoxy, heteroalkyl, alkenyl, alkynyl, cycloalkyl, heterocycloalkyl, aryl, and heteroaryl, wherein each said alkyl, haloalkyl, haloalkoxy, heteroalkyl, alkenyl, alkynyl, cycloalkyl, heterocycloalkyl, aryl, and heteroaryl of $R^{10}$ (when present) is optionally independently unsubstituted or further substituted with one or more independently selected groups selected from the group consisting of lower alkyl, lower alkenyl, lower alkynyl, lower heteroalkyl, halo, —CN, —NO$_2$, —N(R$^8$)$_2$, —C(O)N(R$^8$)$_2$, and cycloalkyl; and each $R^{11}$ is independently selected from the group consisting of —SF$_5$ and —OSF$_5$.

In one embodiment, the compounds of the invention have the structural Formula (IA):

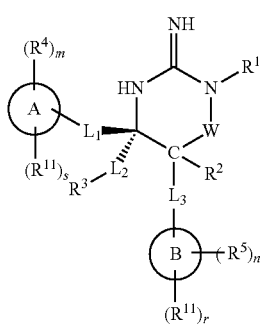

(IA)

wherein each of W, $L_1$, $L_2$, $L_3$, $R^1$, $R^2$, $R^3$, $R^4$, $R^5$, $R^{11}$, ring A, ring B, m, n, r, and s are as defined in Formula (I).

In one embodiment, the compounds of the invention have the structural Formula (IA-1):

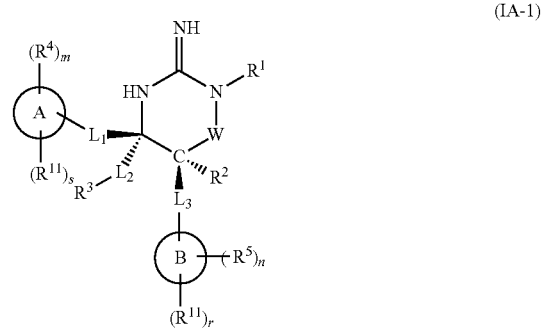

(IA-1)

wherein each of W, $L_1$, $L_2$, $L_3$, $R^1$, $R^2$, $R^3$, $R^4$, $R^5$, $R^{11}$, ring A, ring B, m, n, r, and s are as defined in Formula (I).

In one embodiment, the compounds of the invention have the structural Formula (IA-2):

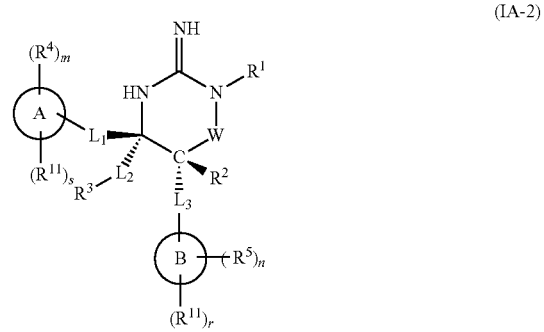

(IA-2)

wherein each of W, $L_1$, $L_2$, $L_3$, $R^1$, $R^2$, $R^3$, $R^4$, $R^5$, $R^{11}$, ring A, ring B, m, n, r, and s are as defined in Formula (I).

In one embodiment, in each of Formulas (a), (I), (IA), (IA-1), and (IA-2), W is selected from the group consisting of —C(O)— and —C(S)—.

In one embodiment, in each of Formulas (a), (I), (IA), (IA-1), and (IA-2), W is selected from the group consisting of —C(O)— and —C(=NR$^{8A}$)—.

In one embodiment, in each of Formulas (a), (I), (IA), (IA-1), and (IA-2), W is selected from the group consisting of —C(S)— and —C(=NR$^{8A}$)—.

In one embodiment, in each of Formulas (a), (I), (IA), (IA-1), and (IA-2), W is —C(O)—.

In one embodiment, in each of Formulas (a), (I), (IA), (IA-1), and (IA-2), W is —C(S)—.

In one embodiment, in each of Formulas (a), (I), (IA), (IA-1), and (IA-2), W is —C(=NR$^{8A}$)—.

In one embodiment, in each of Formulas (a), (I), (IA), (IA-1), and (IA-2), W is —C(=NR$^{8A}$)—, wherein $R^{8A}$ is selected from the group consisting of H and lower alkyl.

In one embodiment, in each of Formulas (a), (I), (IA), (IA-1), and (IA-2), $R^1$ is selected from the group consisting of H, lower alkyl, and cyclopropyl.

In one embodiment, in each of Formulas (a), (I), (IA), (IA-1), and (IA-2), $R^1$ is selected from the group consisting of H and methyl.

In one embodiment, in each of Formulas (a), (I), (IA), (IA-1), and (IA-2), $R^1$ is H.

In one embodiment, in each of Formulas (a), (I), (IA), (IA-1), and (IA-2), $R^1$ is methyl.

In one embodiment, in each of Formulas (a), (I), (IA), (IA-1), and (IA-2), $R^2$ is H.

In one embodiment, in each of Formulas (I), (IA), (IA-1), and (IA-2):

$R^1$ is selected from the group consisting of H, lower alkyl, and cyclopropyl; and $R^2$ is H.

In one embodiment, in each of Formulas (a), (I), (IA), (IA-1), and (IA-2), -$L_2$- is absent or a —$CH_2$— group.

In one embodiment, in each of Formulas (a), (I), (IA), (IA-1), and (IA-2), -$L_2$- is a bond.

In one embodiment, in each of Formulas (a), (I), (IA), (IA-1), and (IA-2), -$L_2$- is a —$CH_2$— group.

In one embodiment, in each of Formulas (a), (I), (IA), (IA-1), and (IA-2), $R^3$ is selected from the group consisting H, alkyl, haloalkyl, heteroalkyl, cycloalkyl, and cycloalkylalkyl-.

In one embodiment, in each of Formulas (a), (I), (IA), (IA-1), and (IA-2), $R^3$ is lower alkyl.

In one embodiment, in each of Formulas (a), (I), (IA), (IA-1), and (IA-2), $R^3$ is methyl.

In one embodiment, in each of Formulas (a), (I), (IA), (IA-1), and (IA-2), -$L_2$- is absent and $R^3$ is methyl.

In one embodiment, in each of Formulas (I), (IA), (IA-1), and (IA-2):

$R^1$ is selected from the group consisting of H, lower alkyl, and cyclopropyl;

$R^2$ is H;

-$L_2$- is a bond; and $R^3$ is methyl.

In one embodiment, the compounds of the invention have the structural Formula (II):

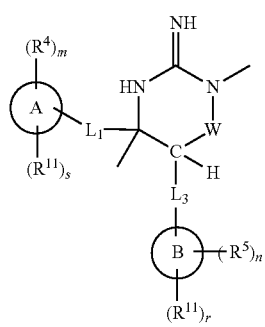

(II)

wherein each of W, -$L_1$-, -$L_3$-, ring A, ring B, $R^4$, $R^5$, $R^{11}$, m, n, r and s are each as defined in Formula (I).

In one embodiment, the compounds of the invention have the structural Formula (IIA):

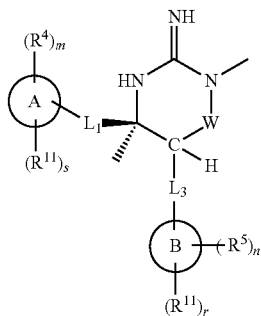

(IIA)

wherein each of W, -$L_1$-, -$L_3$-, ring A, ring B, $R^4$, $R^5$, $R^{11}$, m, n, r and s are each as defined in Formula (I).

In one embodiment, the compounds of the invention have the structural Formula (IIA-1):

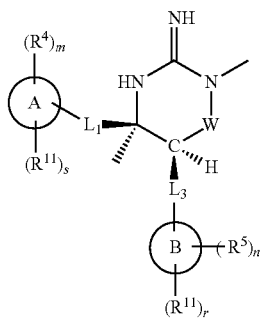

(IIA-1)

wherein each of W, -$L_1$-, -$L_3$-, ring A, ring B, $R^4$, $R^5$, $R^{11}$, n, r and s are each as defined in Formula (I).

In one embodiment, the compounds of the invention have the structural Formula (IIA-2):

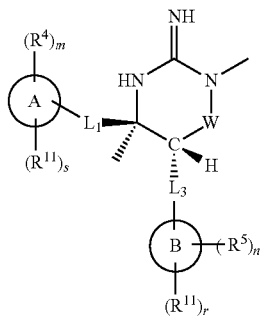

(IIA-2)

wherein each of W, -$L_1$-, -$L_3$-, ring A, ring B, $R^4$, $R^5$, $R^{11}$, m, n, r and s are each as defined in Formula (I).

In one embodiment, in each of Formulas (a), (I), (IA), (IA-1), and (IA-2), (II), (IIA), (IIA-1), and (IIA-2):

W is selected from the group consisting of —C(O)— and —C(S)—.

In one embodiment, in each of Formulas (a), (I), (IA), (IA-1), and (IA-2), (II), (IIA), (IIA-1), and (IIA-2):

W is selected from the group consisting of —C(O)— and —C(=$NR^{8A}$)—.

In one embodiment, in each of Formulas (a), (I), (IA), (IA-1), and (IA-2), (II), (IIA), (IIA-1), and (IIA-2):

W is selected from the group consisting of —C(S)— and —C(=NR$^{8A}$)—.

In one embodiment, in each of Formulas (a), (I), (IA), (IA-1), and (IA-2), (II), (IIA), (IIA-1), and (IIA-2):
W is —C(O)—.

In one embodiment, in each of Formulas (a), (I), (IA), (IA-1), and (IA-2), (II), (IIA), (IIA-1), and (IIA-2):
W is —C(S)—.

In one embodiment, in each of Formulas (a), (I), (IA), (IA-1), and (IA-2), (II), (IIA), (IIA-1), and (IIA-2):
W is —C(=NR$^{8A}$)—.

In one embodiment, in each of Formulas (a), (I), (IA), (IA-1), and (IA-2), (II), (IIA), (IIA-1), and (IIA-2):
W is —C(=NR$^{8A}$)—, wherein R$^{8A}$ is selected from the group consisting of H and lower alkyl.

In one embodiment, in each of Formulas (a), (I), (IA), (IA-1), and (IA-2), (II), (IIA), (IIA-1), and (IIA-2):
-L$_1$- is absent or a divalent -alkyl- group.

In one embodiment, in each of Formulas (a), (I), (IA), (IA-1), and (IA-2), (II), (IIA), (IIA-1), and (IIA-2):
-L$_1$- is a bond.

In one embodiment, in each of Formulas (a), (I), (IA), (IA-1), and (IA-2), (II), (IIA), (IIA-1), and (IIA-2):
-L$_1$- is a divalent -alkyl- group.

In one embodiment, in each of Formulas (a), (I), (IA), (IA-1), and (IA-2), (II), (IIA), (IIA-1), and (IIA-2):
-L$_1$- is a divalent —CH$_2$— group.

In one embodiment, in each of Formulas (a), (I), (IA), (IA-1), and (IA-2), (II), (IIA), (IIA-1), and (IIA-2):
m is 0 or more;
s is 0, 1, or 2,
with the proviso that the sum of r and s is 1 or 2; and
ring A is selected from the group consisting of phenyl and monocyclic heteroaryl.

In one embodiment, in each of Formulas (a), (I), (IA), (IA-1), and (IA-2), (II), (IIA), (IIA-1), and (IIA-2):
m is 0 or more;
s is 0, 1, or 2,
with the proviso that the sum of r and s is 1 or 2; and
ring A is selected from the group consisting of phenyl, pyridyl, pyrazinyl, furanyl, thienyl, pyrimidinyl, pyridazinyl, thiazolyl, oxazolyl, pyrazolyl, imidazolyl, isoxazolyl, and isothiazolyl.

In one embodiment, in each of Formulas (a), (I), (IA), (IA-1), and (IA-2), (II), (IIA), (IIA-1), and (IIA-2):
m is 0 or more;
s is 0, 1, or 2,
with the proviso that the sum of r and s is 1 or 2; and
ring A is selected from the group consisting of phenyl, pyridyl, pyrazolyl, and thienyl.

In one embodiment, in each of Formulas (a), (I), (IA), (IA-1), and (IA-2), (II), (IIA), (IIA-1), and (IIA-2):
m is 0 or more;
s is 0, 1, or 2; and
ring A is selected from the group consisting of phenyl and thienyl;
wherein, when ring A is phenyl, the sum of m and s is 0 to 5, and
when ring A is thienyl, the sum of m and s is 0 to 3; and
with the proviso that the sum of r and s is 1 or 2.

In one embodiment, in each of Formulas (a), (I), (IA), (IA-1), and (IA-2), (II), (IIA), (IIA-1), and (IIA-2):
m is 0 or more;
s is 0, 1, or 2; and
ring A is selected from the group consisting of phenyl and thienyl;
wherein, when ring A is phenyl, the sum of m and s is 0 to 5, and
when ring A is thienyl, the sum of m and s is 0 to 3; and
with the proviso that the sum of r and s is 1 or 2.

In one embodiment, in each of Formulas (a), (I), (IA), (IA-1), and (IA-2), (II), (IIA), (IIA-1), and (IIA-2):
m is 0, 1, 2, or 3;
s is 0, 1, or 2; and
ring A is selected from the group consisting of phenyl and thienyl;
wherein, when ring A is phenyl, the sum of m and s is 0 to 5, and
when ring A is thienyl, the sum of m and s is 0 to 3; and
with the proviso that the sum of r and s is 1 or 2.

In one embodiment, in each of Formulas (a), (I), (IA), (IA-1), and (IA-2), (II), (IIA), (IIA-1), and (IIA-2):
m is 0, 1, 2, or 3;
s is 0; and
ring A is selected from the group consisting of phenyl and thienyl;
and
r is 1 or 2.

In one embodiment, in each of Formulas (a), (I), (IA), (IA-1), and (IA-2), (II), (IIA), (IIA-1), and (IIA-2):
each R$^4$ (when present) is independently selected from the group consisting of halo, —CN, —NO$_2$, —N(R$^8$)$_2$, —NR$^8$C(O)R$^7$, —C(O)N(R$^8$)$_2$, —OR$^7$, alkyl, haloalkyl, heteroalkyl, and alkynyl.

In one embodiment, in each of Formulas (a), (I), (IA), (IA-1), and (IA-2), (II), (IIA), (IIA-1), and (IIA-2):
each R$^4$ (when present) is independently selected from the group consisting of halo, —CN, —NO$_2$, —N(R$^8$)$_2$, —NR$^8$C(O)R$^7$, —C(O)N(R$^8$)$_2$, —OR$^7$, alkyl, haloalkyl, heteroalkyl, and alkynyl, wherein each R$^7$ and each R$^8$ (when present) is independently selected from H and lower alkyl.

In one embodiment, in each of Formulas (a), (I), (IA), (IA-1), and (IA-2), (II), (IIA), (IIA-1), and (IIA-2):
each R$^4$ (when present) is independently selected from the group consisting of halo.

In one embodiment, in each of Formulas (a), (I), (IA), (IA-1), and (IA-2), (II), (IIA), (IIA-1), and (IIA-2):
each R$^4$ (when present) is independently selected from the group consisting of fluoro, chloro, and bromo.

In one embodiment, in each of Formulas (a), (I), (IA), (IA-1), and (IA-2), (II), (IIA), (IIA-1), and (IIA-2):
each R$^4$ (when present) is independently selected from the group consisting of fluoro and bromo.

In one embodiment, in each of Formulas (a), (I), (IA), (IA-1), and (IA-2), (II), (IIA), (IIA-1), and (IIA-2):
each R$^4$ (when present) is fluoro.

In one embodiment, in each of Formulas (a), (I), (IA), (IA-1), and (IA-2), (II), (IIA), (IIA-1), and (IIA-2):
m is 0, 1, 2, or 3;
s is 0;
ring A is selected from the group consisting of phenyl and thienyl;
r is 1 or 2; and
each R$^4$ (when present) is independently selected from the group consisting of halo, —CN, —NO$_2$, —N(R$^8$)$_2$, —NR$^8$C(O)R$^7$, —C(O)N(R$^8$)$_2$, —OR$^7$, alkyl, haloalkyl, heteroalkyl, and alkynyl.

In one embodiment, in each of Formulas (a), (I), (IA), (IA-1), and (IA-2), (II), (IIA), (IIA-1), and (IIA-2):
m is 0, 1, 2, or 3;
s is 0;

ring A is selected from the group consisting of phenyl and thienyl;

r is 1 or 2; and each $R^4$ (when present) is independently selected from the group consisting of halo, —CN, —NO$_2$, —N(R$^8$)$_2$, —NR$^8$C(O)R$^7$, —C(O)N(R$^8$)$_2$, —OR$^7$, alkyl, haloalkyl, heteroalkyl, and alkynyl, wherein each $R^7$ and each $R^8$ (when present) is independently selected from H and lower alkyl.

In one embodiment, in each of Formulas (a), (I), (IA), (IA-1), and (IA-2), (II), (IIA), (IIA-1), and (IIA-2):

m is 0, 1, 2, or 3;

s is 0;

ring A is selected from the group consisting of phenyl and thienyl;

r is 1 or 2; and each $R^4$ (when present) is independently selected from the group consisting of halo.

In one embodiment, in each of Formulas (a), (I), (IA), (IA-1), and (IA-2), (II), (IIA), (IIA-1), and (IIA-2):

m is 0, 1, 2, or 3;

s is 0;

ring A is selected from the group consisting of phenyl and thienyl;

r is 1 or 2; and each $R^4$ (when present) is independently selected from the group consisting of fluoro, chloro, and bromo.

In one embodiment, in each of Formulas (a), (I), (IA), (IA-1), and (IA-2), (II), (IIA), (IIA-1), and (IIA-2):

m is 0, 1, 2, or 3;

s is 0;

ring A is selected from the group consisting of phenyl and thienyl;

r is 1 or 2; and each $R^4$ (when present) is independently selected from the group consisting of fluoro and bromo.

In one embodiment, in each of Formulas (a), (I), (IA), (IA-1), and (IA-2), (II), (IIA), (IIA-1), and (IIA-2):

m is 0, 1, 2, or 3;

s is 0;

ring A is selected from the group consisting of phenyl and thienyl;

r is 1 or 2; and each $R^4$ (when present) is fluoro.

In one embodiment, in each of Formulas (a), (I), (IA), (IA-1), and (IA-2), (II), (IIA), (IIA-1), and (IIA-2):

-L$_1$- is absent or a —CH$_2$—;

s is 0;

r is 1 or 2;

the moiety, is selected from the group consisting of

In one embodiment, in each of Formulas (a), (I), (IA), (IA-1), and (IA-2), (II), (IIA), (IIA-1), and (IIA-2):

-L$_3$- is absent or a -alkyl- group.

In one embodiment, in each of Formulas (a), (I), (IA), (IA-1), and (IA-2), (II), (IIA), (IIA-1), and (IIA-2):

-L$_3$- is a bond.

In one embodiment, in each of Formulas (a), (I), (IA), (IA-1), and (IA-2), (II), (IIA), (IIA-1), and (IIA-2):

-L$_3$- is a -alkyl- group.

In one embodiment, in each of Formulas (a), (I), (IA), (IA-1), and (IA-2), (II), (IIA), (IIA-1), and (IIA-2):

-L$_3$- is absent or a divalent —CH$_2$— group.

In one embodiment, in each of Formulas (a), (I), (IA), (IA-1), and (IA-2), (II), (IIA), (IIA-1), and (IIA-2):

-L$_3$- is a —CH$_2$— group.

In one embodiment, in each of Formulas (a), (I), (IA), (IA-1), and (IA-2), (II), (IIA), (IIA-1), and (IIA-2):

n is 0 or more;

r is 0, 1, or 2, s is 0, 1, or 2, with the provisos that:
(i) the maximum value of the sum of n and r is the maximum number of substitutable hydrogen atoms on ring B, and
(ii) the sum of r and s is 1 or 2; and
ring B is selected from the group consisting of phenyl, benzoxazolyl, benzofuranyl, benzimidazolyl, benzisoxazolyl, pyridyl, pyrazinyl, furanyl, thienyl, pyrimidinyl, pyridazinyl, thiazolyl, oxazolyl, quinolinyl, isoquinolinyl, dihydroquinolinyl, naphthyl, benzothienyl, benzothiazolyl, indazolyl, and indolyl.

In one embodiment, in each of Formulas (a), (I), (IA), (IA-1), and (IA-2), (II), (IIA), (IIA-1), and (IIA-2):
n is 0 or more;
r is 0, 1, or 2, with the provisos that:
(i) the maximum value of the sum of n and r is the maximum number of substitutable hydrogen atoms on ring B, and
(ii) the sum of r and s is 1 or 2; and
ring B is selected from the group consisting of phenyl, indolyl, benzisoxazolyl, benzoxazolyl, benziomidazolyl, pyridyl, thienyl, naphthyl, quinolinyl, isoquinolinyl, and benzothienyl.

In one embodiment, in each of Formulas (a), (I), (IA), (IA-1), and (IA-2), (II), (IIA), (IIA-1), and (IIA-2):
each $R^5$ (when present) is independently selected from the group consisting of halo, —CN, —N($R^8$)$_2$, —NR$^8$C(O)R$^7$, —NR$^8$S(O)$_2$R$^7$, —C(O)R$^7$, —S(O)R$^7$, —S(O)$_2$R$^7$, —OR$^7$, —SR$^7$, alkyl, haloalkyl, heteroalkyl, —O-heteroalkyl, alkenyl, alkynyl, cycloalkyl, heterocycloalkyl, aryl, and monocyclic heteroaryl,
wherein each said alkyl, said alkenyl, said alkynyl, said cycloalkyl, said heterocycloalkyl, said aryl, and said monocyclic heteroaryl of $R^5$ (when present) is optionally and independently further substituted with one or more groups independently selected from the group consisting of halo, lower alkyl, lower alkenyl, lower alkynyl, lower heteroalkyl, —NO$_2$, —N($R^8$)$_2$, and —OR$^7$.

In one embodiment, in each of Formulas (a), (I), (IA), (IA-1), and (IA-2), (II), (IIA), (IIA-1), and (IIA-2):
each $R^5$ (when present) is independently selected from the group consisting of halo, —CN, —N($R^8$)$_2$, —NR$^8$C(O)R$^7$, —NR$^8$S(O)$_2$R$^7$, —C(O)R$^7$, —S(O)R$^7$, —S(O)$_2$R$^7$, —OR$^7$, —SR$^7$, alkyl, haloalkyl, heteroalkyl, —O-heteroalkyl, alkynyl, cyclopropyl, cyclobutyl, cyclopentyl, cyclohexyl, phenyl, pyridyl, furanyl, thienyl, pyridazinyl, oxazolyl, isoxazolyl, oxetanyl, pyrrolyl, oxadiazolyl, pyrrolidinyl, furanyl, piperidinyl, and tetrahydropyranyl;
wherein each $R^7$ and each $R^8$ (when present) is independently selected from the group consisting of H and lower alkyl,
and
wherein each said alkyl, -alkoxy, haloalkyl, heteroalkyl, —O-heteroalkyl, alkenyl, alkynyl, cyclopropyl, cyclobutyl, cyclopentyl, cyclohexyl, phenyl, pyridyl, furanyl, thienyl, pyridazinyl, oxazolyl, isoxazolyl, oxetanyl, and pyrrolyl of $R^5$ (when present) is optionally and independently further substituted with one or more groups independently selected from the group consisting of halo, lower alkyl, lower alkenyl, lower alkynyl, lower heteroalkyl, —CN, —NO$_2$, —N($R^8$)$_2$, and —OH.

In one embodiment, in each of Formulas (a), (I), (IA), (IA-1), and (IA-2), (II), (IIA), (IIA-1), and (IIA-2):
each $R^5$ (when present) is independently selected from the group consisting of halo, —CN, —N($R^8$)$_2$, —NR$^8$C(O)R$^7$, —NR$^8$S(O)$_2$R$^7$, —C(O)R$^7$, —S(O)R$^7$, —S(O)$_2$R$^7$, —OR$^7$, —SR$^7$, alkyl, haloalkyl, heteroalkyl, —O-heteroalkyl, alkynyl, cyclopropyl, cyclobutyl, cyclopentyl, cyclohexyl, phenyl, pyridyl, furanyl, thienyl, pyridazinyl, oxazolyl, isoxazolyl, oxetanyl, and pyrrolyl,
wherein each said alkyl, -alkoxy, haloalkyl, heteroalkyl, —O-heteroalkyl, alkynyl, cyclopropyl, cyclobutyl, cyclopentyl, cyclohexyl, phenyl, pyridyl, furanyl, thienyl, pyridazinyl, oxazolyl, isoxazolyl, oxetanyl, and pyrrolyl of $R^5$ (when present) is optionally and independently further substituted with one or more groups independently selected from the group consisting of halo, lower alkyl, lower alkenyl, lower alkynyl, lower heteroalkyl, —NO$_2$, —N($R^8$)$_2$, and —OH,
and
wherein each $R^7$ and each $R^8$ (when present) is independently selected from the group consisting of H and lower alkyl.

In one embodiment, in each of Formulas (a), (I), (IA), (IA-1), and (IA-2), (II), (IIA), (IIA-1), and (IIA-2):
each $R^5$ (when present) is independently selected from the group consisting of halo, —ON, lower alkyl, lower alkenyl, lower haloalkyl, —C(O)-cyclopropyl, oxetanyl, lower alkyl-substituted oxetanyl, cyclopropyl, lower heteroalkyl substituted cyclopropyl, lower alkyl-CN, lower heteroalkyl, and phenyl.

In one embodiment, in each of Formulas (a), (I), (IA), (IA-1), and (IA-2), (II), (IIA), (IIA-1), and (IIA-2):
n is 0 or more, with the proviso that the sum of n and r is the maximum number of substitutable hydrogen atoms on ring B;
r is 0, 1, or 2, with the proviso that the sum of r and s is 1 or 2; and
each $R^5$ (when present) is independently selected from the group consisting of halo, —CN, —N($R^8$)$_2$, —NR$^8$C(O)R$^7$, —NR$^8$S(O)$_2$R$^7$, —C(O)R$^7$, —S(O)R$^7$, —S(O)$_2$R$^7$, —OR$^7$, —SR$^7$, alkyl, haloalkyl, heteroalkyl, —O-heteroalkyl, alkenyl, alkynyl, cycloalkyl, heterocycloalkyl, aryl, and monocyclic heteroaryl,
wherein each said alkyl, said alkenyl, said alkynyl, said cycloalkyl, said heterocycloalkyl, said aryl, and said monocyclic heteroaryl of $R^5$ (when present) is optionally and independently further substituted with one or more groups independently selected from the group consisting of halo, lower alkyl, lower alkenyl, lower alkynyl, lower heteroalkyl, —CM, —NO$_2$, —N($R^8$)$_2$, and —OR$^7$.

In one embodiment, in each of Formulas (a), (I), (IA), (IA-1), and (IA-2), (II), (IIA), (IIA-1), and (IIA-2):
n is 0 or more, with the proviso that the sum of n and r is the maximum number of substitutable hydrogen atoms on ring B;
r is 0, 1, or 2, with the proviso that the sum of r and s is 1 or 2; and
each $R^5$ (when present) is independently selected from the group consisting of halo, —CN, —N($R^8$)$_2$, —NR$^8$C(O)R$^7$, —NR$^8$S(O)$_2$R$^7$, —C(O)R$^7$, —S(O)R$^7$, —S(O)$_2$R$^7$, —OR$^7$, —SR$^7$, alkyl, haloalkyl, heteroalkyl, —O-heteroalkyl, alkynyl, cyclopropyl, cyclobutyl, cyclopentyl, cyclohexyl, phenyl, pyridyl, furanyl, thienyl, pyridazinyl, oxazolyl, isoxazolyl, oxetanyl, pyrrolyl, oxadiazolyl, pyrrolidinyl, furanyl, piperidinyl, and tetrahydropyranyl;
wherein each $R^7$ and each $R^8$ (when present) is independently selected from the group consisting of H and lower alkyl, and
wherein each said alkyl, -alkoxy, haloalkyl, heteroalkyl, —O-heteroalkyl, alkenyl, alkynyl, cyclopropyl, cyclobutyl, cyclopentyl, cyclohexyl, phenyl, pyridyl, furanyl, thienyl, pyridazinyl, oxazolyl, isoxazolyl, oxetanyl, and pyrrolyl of $R^5$ (when present) is optionally and independently further substituted with one or more groups independently selected from the group consisting of halo, lower alkyl, lower alkenyl, lower alkynyl, lower heteroalkyl, —CN, —NO$_2$, —N(R$^8$)$_2$, and —OH.

In one embodiment, in each of Formulas (a), (I), (IA), (IA-1), and (IA-2), (II), (IIA), (IIA-1), and (IIA-2):

n is 0 or more, with the proviso that the sum of n and r is the maximum number of substitutable hydrogen atoms on ring B;

r is 0, 1, or 2, with the proviso that the sum of r and s is 1 or 2; and each $R^5$ (when present) is independently selected from the group consisting of halo, —CN, —N(R$^8$)$_2$, —NR$^8$C(O)R$^7$, —NR$^8$S(O)$_2$R$^7$, —C(O)R$^7$, —S(O)R$^7$, —S(O)$_2$R$^7$, —OR$^7$, —SR$^7$, alkyl, haloalkyl, heteroalkyl, —O-heteroalkyl, alkenyl, alkynyl, cyclopropyl, cyclobutyl, cyclopentyl, cyclohexyl, phenyl, pyridyl, furanyl, thienyl, pyridazinyl, oxazolyl, isoxazolyl, oxetanyl, and pyrrolyl, wherein each said alkyl, -alkoxy, haloalkyl, heteroalkyl, —O-heteroalkyl, alkynyl, cyclopropyl, cyclobutyl, cyclopentyl, cyclohexyl, phenyl, pyridyl, furanyl, thienyl, pyridazinyl, oxazolyl, isoxazolyl, oxetanyl, and pyrrolyl of $R^5$ (when present) is optionally and independently further substituted with one or more groups independently selected from the group consisting of halo, lower alkyl, lower alkenyl, lower alkynyl, lower heteroalkyl, —CN, —NO$_2$, —N(R$^8$)$_2$, and —OH, and wherein each $R^7$ and each $R^8$ (when present) is independently selected from the group consisting of H and lower alkyl.

In one embodiment, in each of Formulas (a), (I), (IA), (IA-1), and (IA-2), (II), (IIA), (IIA-1), and (IIA-2):

n is 0 or more, with the proviso that the sum of n and r is the maximum number of substitutable hydrogen atoms on ring B;

r is 0, 1, or 2, with the proviso that the sum of r and s is 1 or 2; and each $R^5$ (when present) is independently selected from the group consisting of halo, —CN, lower alkyl, lower alkenyl, lower haloalkyl, —C(O)-cyclopropyl, oxetanyl, lower alkyl-substituted oxetanyl, cyclopropyl, lower heteroalkyl substituted cyclopropyl, lower alkyl-CN, lower heteroalkyl, and phenyl.

In one embodiment, in each of Formulas (a), (I), (IA), (IA-1), and (IA-2), (II), (IIA), (IIA-1), and (IIA-2):

-$L_3$- is absent or a divalent —CH$_2$— group;

n is 0 or more;

r is 0, 1, or 2;

with the provisos that:

(i) that the sum of n and r is the maximum number of substitutable hydrogen atoms on ring B, and (ii) the sum of r and s is 1 or 2;

ring B is phenyl and the moiety

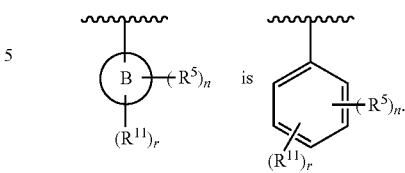

In one embodiment, in each of Formulas (a), (I), (IA), (IA-1), and (IA-2), (II), (IIA), (IIA-1), and (IIA-2):

-$L_3$- is absent or a divalent —CH$_2$— group;

ring B is phenyl;

n is 0;

r is 1; and and the moiety

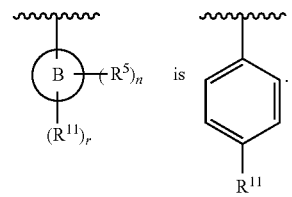

In one such embodiment, s is 0 and $R^{11}$ is —SF$_5$. In another such embodiment, s is 0 and $R^{11}$ is —OSF$_5$.

In one embodiment, in each of Formulas (a), (I), (IA), (IA-1), and (IA-2), (II), (IIA), (IIA-1), and (IIA-2):

-$L_1$- is absent or a divalent -alkyl- group;

m is 0 or more;

s is 0, 1, or 2;

ring A is selected from the group consisting of phenyl, pyridyl, pyrazinyl, pyrazolyl, furanyl, thienyl, pyrimidinyl, pyridazinyl, thiazolyl, and oxazolyl;

each $R^4$ (when present) is independently selected from the group consisting of halo, —CN, —NO$_2$, —N(R$^8$)$_2$, —NR$^8$C(O)R$^7$, —C(O)N(R$^8$)$_2$, —OR$^7$, alkyl, haloalkyl, heteroalkyl, and alkynyl;

-$L_3$- is absent or a divalent —CH$_2$— group;

n is 0 or more;

r is 0, 1, or 2;

ring B is selected from the group consisting of phenyl, benzoxazolyl, benzofuranyl, benzimidazolyl, benzisoxazolyl, pyridyl, pyrazinyl, furanyl, thienyl, pyrimidinyl, pyridazinyl, thiazolyl, oxazolyl, quinolinyl, isoquinolinyl, dihydroquinolinyl, naphthyl, benzothienyl, benzothiazolyl, indazolyl, and indolyl;

each $R^5$ (when present) is independently selected from the group consisting of halo, —CN, —N(R$^8$)$_2$, —NR$^8$C(O)R$^7$, —NR$^8$S(O)$_2$R$^7$, —C(O)R$^7$, —S(O)R$^7$, —S(O)$_2$R$^7$, —SR$^7$, alkyl, haloalkyl, heteroalkyl, —O-heteroalkyl, alkenyl, cycloalkyl, heterocycloalkyl, aryl, and monocyclic heteroaryl, wherein each said alkyl, said alkenyl, said alkenyl, said cycloalkyl, said heterocycloalkyl, said aryl, and said monocyclic heteroaryl of $R^5$ (when present) is optionally and independently further substituted with one or more groups independently selected from the group consisting of halo, lower alkyl, lower alkenyl, lower alkynyl, lower heteroalkyl, —CN, —NO$_2$, —N(R$^8$)$_2$, and —OH;

with the provisos that:

(i) the sum of m and s is the maximum number of substitutable hydrogen atoms on ring A, (ii) the sum of n and r is the maximum number of substitutable hydrogen atoms on ring B, and (iii) the sum of r and s is 1 or 2.

In one embodiment, in each of Formulas (a), (I), (IA), (IA-1), and (IA-2), (II), (IIA), (IIA-1), and (IIA-2):

-$L_1$- is absent or a divalent —$CH_2$— group;

ring A is selected from the group consisting of phenyl and thienyl;

wherein, when ring A is phenyl, the sum of m and s is 0 to 5, and when ring A is thienyl, the sum of m and s is 0 to 3;

each $R^4$ (when present) is independently selected from the group consisting of halo, —CN, —$NO_2$, —$N(R^8)_2$, —$NR^8C(O)R^7$, —$C(O)N(R^8)_2$, —$OR^7$, alkyl, haloalkyl, heteroalkyl, and alkynyl;

-$L_3$- is absent or a diavalent -alkyl- group;

ring B is selected from the group consisting of phenyl, pyridyl, thienyl, naphthyl, quinolinyl, isoquinolinyl, and benzothienyl;

n is 0 or more;

r is 0, 1, or 2, with the provisos that (i) the sum of n and r is the maximum number of substitutable hydrogen atoms on ring B, and (ii) the sum of r and s is 1 or 2;

each $R^5$ (when present) is independently selected from the group consisting of halo, —CN, —$N(R^8)_2$, —$NR^8C(O)R^7$, —$NR^8S(O)_2R^7$, —$C(O)R^7$, —$S(O)R^7$, —$S(O)_2R^7$, —$OR^7$, —$SR^7$, alkyl, haloalkyl, heteroalkyl, —O-heteroalkyl, alkenyl, alkynyl, cyclopropyl, cyclobutyl, cyclopentyl, cyclohexyl, phenyl, pyridyl, furanyl, thienyl, pyridazinyl, oxazolyl, isoxazolyl, oxetanyl, and pyrrolyl, wherein each said alkyl, -alkoxy, haloalkyl, heteroalkyl, —O-heteroalkyl, alkynyl, cyclopropyl, cyclobutyl, cyclopentyl, cyclohexyl, phenyl, pyridyl, furanyl, thienyl, pyridazinyl, oxazolyl, isoxazolyl, oxetanyl, and pyrrolyl of $R^5$ (when present) is optionally and independently further substituted with one or more groups independently selected from the group consisting of halo, lower alkyl, lower alkenyl, lower alkynyl, lower heteroalkyl, —CN, —$NO_2$, —$N(R^8)_2$, and —OH;

and each $R^7$ and each $R^8$ (when present) is independently selected from the group consisting of H and lower alkyl.

In one embodiment, in each of Formulas (a), (I), (IA), (IA-1), and (IA-2), (II), (IIA), (IIA-1), and (IIA-2):

-$L_1$- is absent or a divalent —$CH_2$— group;

s is 0;

the moiety,

![structure with ring A, $(R^4)_m$, $(R^{11})_s$]

is selected from the group consisting of

![thiophene with Br], ![thiophene with F],

![thiophene with F,S,F], ![thiophene with F,S,F],

![thiophene with F], ![thiophene with F,F],

![thiophene with F,Br], ![thiophene with NC,S],

![phenyl with F,F], ![phenyl with F,F,F],

![phenyl with F,F], ![phenyl with F,F,F],

![phenyl with F,F], ![phenyl with F,F],

![phenyl with F,F,Br], ![phenyl with F],

![phenyl with F,F], and ![phenyl with F,F];

n is 0, 1, 2, or 3;

r is 1 or 2;

ring B is selected from the group consisting of phenyl, pyridyl, thienyl, naphthyl, quinolinyl, isoquinolinyl, and benzothienyl; and each $R^5$ (when present) is independently selected from the group consisting of halo, —CN, lower alkyl, lower alkenyl, lower haloalkyl, —C(O)-cyclopropyl, oxetanyl, lower alkyl-substituted oxetanyl, cyclopropyl, lower heteroalkyl substituted cyclopropyl, lower alkyl-CN, lower heteroalkyl, and phenyl.

In one embodiment, in each of Formulas (a), (I), (IA), (IA-1), and (IA-2), (II), (IIA), (IIA-1), and (IIA-2):

-$L_1$- is absent or a divalent —$CH_2$— group;

s is 0;

the moiety,

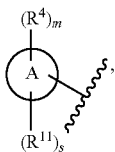

is selected from the group consisting of

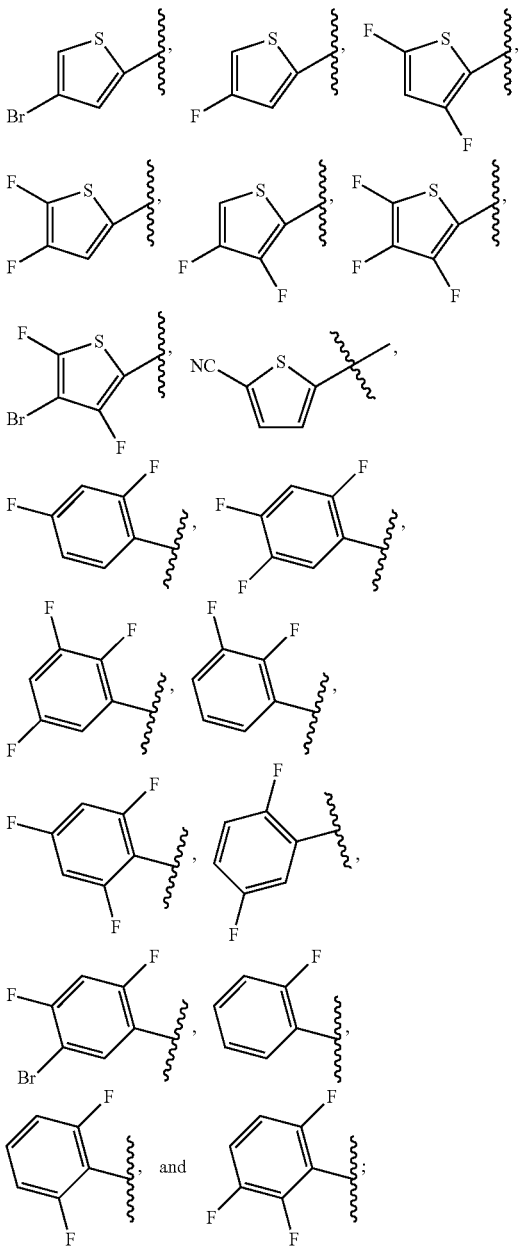

-L$_3$- is absent or a divalent —CH$_2$— group;
ring B is phenyl;
n is 0;
r is 1; and and the moiety

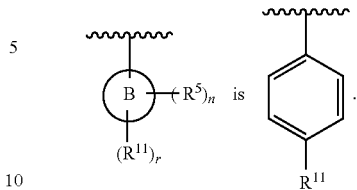

In one such embodiment, R$^{11}$ is —SF$_5$. In another such embodiment, R$^{11}$ is —OSF$_5$.

In another embodiment, the present invention encompasses deuterates of the compounds of the invention, or tautomers thereof, or a pharmaceutically acceptable salt of said deuterated compound or tautomer of the invention. Specific, non-limiting examples of deuterated compounds of the invention are as described and exemplified herein and include, deuterated compounds of Formulas (I$^d$), (II$^d$), and (III$^d$). Those of ordinary skill in the art will readily appreciate that, in addition to the non-limiting examples shown, other available hydrogen atoms may be deuterated in a similar manner as described hereinbelow. Such deuterated compounds are also to be considered as being among the compounds of the invention. The resulting compound is referred to herein as a "deuterated" compound of the invention or, alternatively, as "deuterate(s)" of compounds of the invention. The compounds of the invention may be deuterated in a manner known to those of ordinary skill in the art, e.g., as described herein.

Thus, in one non-limiting embodiment, deuterated compounds of the invention have the structural Formula (I$^d$):

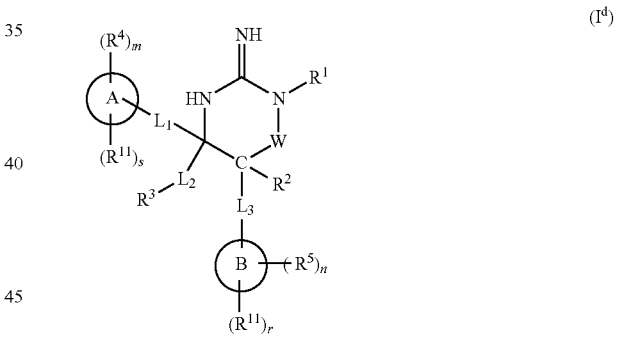

wherein:
one or more hydrogen atoms present in R$^1$, R$^2$, R$^3$, R$^4$ (when present) and/or R$^5$ (when present) is replaced by deuterium; and each of the remaining variables is as defined in Formula (I), or as described in any of the embodiments described herein, e.g., those of formulas (IA), (IA-1), (IA-2), (II), (II-A), (II-A1), and (II-A2), and the various embodiments thereof, are also within the scope of the compounds of Formula (I$^d$).

For example, in one non-limiting embodiment, in Formula (I$^d$), R$^1$ is D and each of W, R$^2$, R$^3$, R$^4$, R$^5$, R$^{11}$, -L$_1$-, -L$_2$-, -L$_3$-, ring A, ring B, m, n, r, and s are as defined in Formula (I) or as in any one of (IA), (IA-1), (IA-2), (II), (II-A), (II-A1), or (II-A2), or the various embodiments described herein.

As another example, in another non-limiting embodiment, in Formula (I$^d$), R$^2$ is D and each of W, R$^1$, R$^3$, R$^4$, R$^5$, R$^{11}$, -L$_1$-, -L$_2$-, -L$_3$-, ring A, ring B, m, n, r, and s are as defined in Formula (I) or as in any one of (IA), (IA-1), (IA-2), (II), (II-A), (II-A1), or (II-A2), or the various embodiments described herein.

As another example, in another non-limiting embodiment, in Formula ($I^d$), $R^4$ is D and each of W, $R^1$, $R^2$, $R^3$, $R^5$, $R^{11}$, -$L_1$-, -$L_2$-, -$L_3$-, ring A, ring B, m, n, r, and s are as defined in Formula (I) or as in any one of (IA), (IA-1), (IA-2), (II), (II-A), (II-A1), or (II-A2), or the various embodiments described herein.

As another example, in another non-limiting embodiment, in Formula ($I^d$), $R^5$ is D and each of W, $R^1$, $R^2$, $R^3$, $R^4$, $R^{11}$, -$L_1$-, -$L_2$-, -$L_3$-, ring A, ring B, m, n, r, and s are as defined in Formula (I) or as in any one of (IA), (IA-1), (IA-2), (II), (II-A), (II-A1), or (II-A2), or the various embodiments described herein.

As another example, in another non-limiting embodiment, in Formula ($I^d$), $R^{11}$ is D and each of W, $R^1$, $R^2$, $R^3$, $R^4$, -$L_1$-, -$L_2$-, -$L_3$-, ring A, ring B, m, n, r, and s are as defined in Formula (I) or as in any one of (IA), (IA-1), (IA-2), (II), (II-A), (II-A1), or (II-A2), or the various embodiments described herein.

By way of further illustration, in another non-limiting embodiment, deuterated compounds of the invention have the structural Formula ($II^d$):

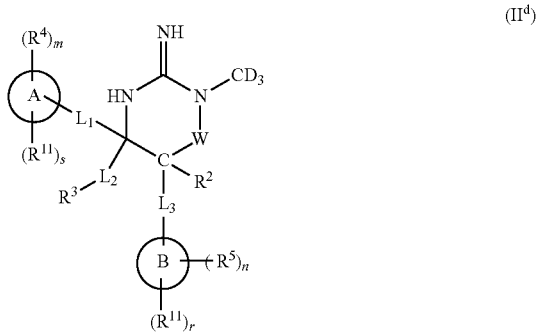

wherein:

the moiety —$CD_3$ represents a deuterated form of the moiety —$CH_3$; and each of the remaining variables is as defined in Formula (I), or as described in any of the embodiments described herein, e.g., those of formulas (IA), (IA-1), (IA-2), (II), (II-A), (II-A1), and (II-A2), and the various embodiments thereof, are also within the scope of the compounds of Formula ($II^d$).

By way of further illustration, in another non-limiting embodiment, deuterated compounds of the invention have the structural Formula ($III^d$):

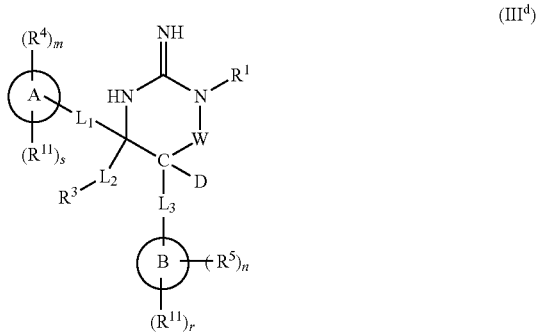

wherein:

the moiety -D represents a deuterated form of hydrogen; and each of the remaining variables is as defined in Formula (I), or as described in any of the embodiments described herein, e.g., those of formulas (IA), (IA-1), (IA-2), (II), (II-A), (II-A1), and (II-A2), and the various embodiments thereof, are also within the scope of the compounds of Formula ($III^d$).

In another embodiment, the present invention encompasses a stereoisomer or racemic mixture of a compound of the invention, or a tautomer thereof, or a pharmaceutically acceptable salt of said compound or said tautomer. It shall be appreciated that, while the present invention encompasses all stereoisomers and racemic mixtures of the compounds of the invention, the stereoconfiguration shown in the structural formulas and in the examples are also contemplated as being within the scope of the invention.

In another embodiment, 1 to 3 carbon atoms of the compounds of the invention may be replaced with 1 to 3 silicon atoms so long as all valency requirements are satisfied.

In another embodiment, the compounds of the invention are each of the compounds of the tables below and have a structure shown for the corresponding example in the preparative examples below.

Other embodiments, the present invention includes tautomers and stereoisomers of each of the compounds in Table 1 below, and pharmaceutically acceptable salts and solvates of said compounds, said stereoisomers, and/or said tautomers.

In another embodiment, the invention provides a composition comprising at least one compound of the invention, or a tautomer or stereoisomer thereof, or salt or solvate of said compound, said stereoisomer, or said tautomer, and a suitable carrier or diluent.

In another embodiment, the invention provides a pharmaceutical composition comprising at least one compound of the invention, or a tautomer or stereoisomer thereof, or pharmaceutically acceptable salt or solvate of said compound, said stereoisomer, or said tautomer, and a pharmaceutically acceptable carrier or diluent.

In another embodiment, the invention provides a pharmaceutical composition comprising at least one solvate of a compound of the invention, or a tautomer or isomer thereof, or pharmaceutically acceptable salt or solvate of said compound or said tautomer, and a pharmaceutically acceptable carrier or diluent.

In another embodiment, the invention provides a pharmaceutical composition comprising at least one pharmaceutically acceptable salt of a compound of the invention, or a tautomer or stereoisomer thereof, or pharmaceutically acceptable salt or solvate of said compound, said stereoisomer, or said tautomer, and a pharmaceutically acceptable carrier or diluent.

In another embodiment, the invention provides a pharmaceutical composition comprising at least one tautomer of a compound of the invention, or a tautomer or stereoisomer thereof, or pharmaceutically acceptable salt or solvate of said compound, said stereoisomer, or said tautomer, and a pharmaceutically acceptable carrier or diluent.

In another embodiment, the invention provides a pharmaceutical composition comprising at least one compound of the invention, or a tautomer or stereoisomer thereof, or pharmaceutically acceptable salt or solvate of said compound, said stereoisomer, or said tautomer, together with at least one additional therapeutic agent, and a pharmaceutically acceptable carrier or diluent.

Non-limiting examples of additional therapeutic agents for use in combination with the compounds of the invention include drugs selected from the group consisting of: (a) drugs useful for the treatment of Alzheimer's disease and/or drugs useful for treating one or more symptoms of Alzheimer's disease, (b) drugs useful for inhibiting the synthesis Aβ, and (c) drugs useful for treating neurodegenerative diseases.

Additional non-limiting examples of additional therapeutic agents for use in combination with the compounds of the invention include drugs useful for the treatment, prevention, delay of onset, amelioration of any pathology associated with Aβ and/or a symptom thereof. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $β_2$ microglobulins and complications arising therefrom in hemodialysis patients), scrapie, bovine spongiform encephalitis, and Creutzfeld-Jakob disease, comprising administering to said patient at least one compound of the invention, or a tautomer or isomer thereof, or pharmaceutically acceptable salt or solvate of said compound or said tautomer, in an amount effective to inhibit said pathology or pathologies.

In embodiments of the invention comprising at least one additional therapeutic agent, additional non-limiting examples of additional therapeutic agents for use in combination with compounds of the invention include: muscarinic antagonists (e.g., $m_1$ agonists (such as acetylcholine, oxotremorine, carbachol, or McNa343), or $m_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®), galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g, PBT2); and GPR3 modulators; and antihistamines such as Dimebolin (e.g., Dimebon®, Pfizer).

In another embodiment, the invention provides a pharmaceutical composition comprising an effective amount of one or more (e.g., one) compounds of the invention, and effective amount of one or more cholinesterase inhibitors (e.g., acetyl- and/or butyrylchlolinesterase inhibitors), and a pharmaceutically acceptable carrier.

In another embodiment, the invention provides a pharmaceutical composition comprising an effective amount of one or more (e.g., one) compounds of the invention, and effective amount of one or more muscarinic antagonists (e.g., $m_1$ agonists or $m_2$ antagonists), and a pharmaceutically acceptable carrier.

In one embodiment, the invention provides combinations comprising an effective (i.e., therapeutically effective) amount of one or more compounds of the invention, in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e, donepezil hydrochloride, available as the Aricept® brand of donepezil hydrochloride), N-methyl-D-aspartate receptor inhibitors (such as, for example, Namenda® (memantine HCl)); anti-amyloid antibodies (such as bapineuzumab, Wyeth/Elan), gamma secretase inhibitors, gamma secretase modulators, and beta secretase inhibitors other than the compounds of the invention.

In one embodiment, the invention provides combinations comprising an effective (i.e., therapeutically effective) amount of one or more compounds of the invention, in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e, donepezil hydrochloride, available as the Aricept® brand of donepezil hydrochloride), N-methyl-D-aspartate receptor inhibitors (such as, for example, Namenda® (memantine HCl)).

In one embodiment, the invention provides combinations comprising an effective (i.e., therapeutically effective) amount of one or more compounds of the invention, in combination with an effective (i.e., therapeutically effective) amount of one or more gamma secretase inhibitors.

In one embodiment, the invention provides combinations comprising an effective (i.e., therapeutically effective) amount of one or more compounds of the invention, in combination with an effective (i.e., therapeutically effective) amount of one or more gamma secretase modulators.

In one embodiment, the invention provides combinations comprising an effective (i.e., therapeutically effective) amount of one or more compounds of the invention, or a tautomer or stereoisomer thereof, or pharmaceutically acceptable salt or solvate of said compound, said stereoisomer, or said tautomer, in combination with an effective (i.e., therapeutically effective) amount of one or more gamma secretase inhibitors and in further combination with one or more gamma secretase modulators.

In another embodiment, the invention provides a compound of the invention, or a tautomer or stereoisomer thereof, or pharmaceutically acceptable salt or solvate of said compound, said stereoisomer, or said tautomer, in pure form.

In another embodiment, the invention provides a compound of the invention or a tautomer or stereoisomer thereof, or pharmaceutically acceptable salt or solvate of said compound, said stereoisomer, or said tautomer, in isolated form.

In another embodiment, the invention provides a compound of the invention or a tautomer or stereoisomer thereof, or pharmaceutically acceptable salt or solvate of said compound, said stereoisomer, or said tautomer, in pure and isolated form.

Esters and prodrugs of the compounds of the invention, or tautomers or stereoisomers thereof, or pharmaceutically acceptable salts or solvates of said compounds, said stereoisomers, and/or said tautomers, are also contemplated as being included within the scope of the invention, and are described more fully below.

Deuterates of the compounds of the invention, or tautomers or stereoisomers of said deuterates, or pharmaceutically acceptable salts or solvates of said deuterates, said stereoisomers, and/or said tautomers, are also contemplated as being included within the scope of the invention, and are described more fully above.

In another embodiment, the invention provides a method of preparing a pharmaceutical composition comprising the step of admixing at least one compound of the invention, or a tautomer or stereoisomer thereof, or pharmaceutically acceptable salt or solvate of said compound, said stereoisomer, or said tautomer, and a pharmaceutically acceptable carrier or diluent.

In another embodiment, the invention provides a method of inhibiting β-secretase comprising exposing a population of cells expressing β-secretase to at least one compound of the invention, or a tautomer or stereoisomer thereof, or pharmaceutically acceptable salt or solvate of said compound, said stereoisomer, or said tautomer, in an amount effective to inhibit β-secretase.

In another embodiment, the invention provides a method of inhibiting β-secretase in a patient in need thereof comprising administering at least one compound of the invention, or a tautomer or stereoisomer thereof, or pharmaceutically acceptable salt or solvate of said compound, said stereoisomer, or said tautomer, in a therapeutically effective amount to inhibit β-secretase in said patient.

In another embodiment, the invention provides a method of inhibiting BACE-1 comprising exposing a population of cells expressing BACE-1 to at least one compound of the invention, or a tautomer or stereoisomer thereof, or pharmaceutically acceptable salt or solvate of said compound or said tautomer, in an amount effective to inhibit BACE-1 in said patient. In one such embodiment, said population of cells is in vivo. In another such embodiment, said population of cells is ex vivo. In another such embodiment, said population of cells is in vitro.

In another embodiment, the invention provides a method of inhibiting BACE-1 in a patient in need thereof comprising administering to said patient at least one compound of the invention, or a tautomer or stereoisomer thereof, or pharmaceutically acceptable salt or solvate of said compound, said stereoisomer, or said tautomer, in a therapeutically effective amount to inhibit BACE-1 in said patient.

In another embodiment, the invention provides a method of inhibiting the formation of Aβ from APP in a patient in need thereof, comprising administering to said patient at least one compound of the invention, or a tautomer or stereoisomer thereof, or pharmaceutically acceptable salt or solvate of said compound, said stereoisomer, or said tautomer, in an amount effective to inhibit said Aβ formation.

In another embodiment, the invention provides a method of inhibiting the formation of Aβ plaque in a patient in need thereof, comprising administering to said patient at least one compound of the invention, or a tautomer or stereoisomer thereof, or pharmaceutically acceptable salt or solvate of said compound, said stereoisomer, or said tautomer, in an amount effective to inhibit said Aβ plaque formation.

In another embodiment, the invention provides a method of inhibiting the formation of Aβ fibrils in a patient in need thereof, comprising administering to said patient at least one compound of the invention, or a tautomer or stereoisomer thereof, or pharmaceutically acceptable salt or solvate of said compound, said stereoisomer, or said tautomer, in an amount effective to inhibit said Aβ fibril formation.

In another embodiment, the invention provides a method of inhibiting the formation of Aβ oligomers in a patient in need thereof, comprising administering to said patient at least one compound of the invention, or a tautomer or stereoisomer thereof, or pharmaceutically acceptable salt or solvate of said compound, said stereoisomer, or said tautomer, in an amount effective to inhibit said Aβ fibril formation.

In another embodiment, the invention provides a method of inhibiting the formation of Aβ fibrils and Aβ oligomers in a patient in need thereof, comprising administering to said patient at least one compound of the invention, or a tautomer or stereoisomer thereof, or pharmaceutically acceptable salt or solvate of said compound, said stereoisomer, or said tautomer, in an amount effective to inhibit said Aβ fibril formation.

In another embodiment, the invention provides a method of inhibiting the formation of senile plaques and/or neurofibrillary tangles in a patient in need thereof, comprising administering to said patient at least one compound of the invention, or a tautomer or stereoisomer thereof, or pharmaceutically acceptable salt or solvate of said compound, said stereoisomer, or said tautomer, in an amount effective to inhibit said Aβ fibril formation.

In another embodiment, the invention provides a method of treating, preventing, and/or delaying the onset of an amyloid β pathology ("Aβ pathology") and/or one or more symptoms of said pathology comprising administering at least one compound of the invention, or a tautomer or stereoisomer thereof, or pharmaceutically acceptable salt or solvate of said compound, said stereoisomer, or said tautomer, to a patient in need thereof in an amount effective to treat said pathology.

In another embodiment, the invention provides a method of treating, preventing, and/or delaying the onset of one or more pathologies associated with Aβ and/or one or more symptoms of one or more pathologies associated with Aβ. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/ or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $\beta_2$ microglobulins and complications arising therefrom in hemodialysis patients), scrapie, bovine spongiform encephalitis, Creutzfeld-Jakob disease, and traumatic brain injury ("TBI"), comprising administering to said patient at least one compound of the invention, or a tautomer or stereoisomer thereof, or pharmaceutically acceptable salt or solvate of said compound, said stereoisomer, or said tautomer, in an amount effective to inhibit said pathology or pathologies.

In one embodiment, the invention provides a method of treating one or more neurodegenerative diseases, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of inhibiting the deposition of amyloid protein (e.g., amyloid beta protein) in, on or around neurological tissue (e.g., the brain), comprising administering an effective (i.e., therapeutically effective) amount of one or more compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of inhibiting the deposition of amyloid protein (e.g., amyloid beta protein) in, on or around neurological tissue (e.g., the brain), comprising administering an effective (i.e., therapeutically effective) amount of a compound of the invention (or a tautomer or stereoisomer thereof, or pharmaceutically acceptable salt or solvate of said compound, said stereoisomer, or said tautomer) to a patient in need of treatment.

In one embodiment, the invention provides a method of treating Alzheimer's disease, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating Alzheimer's disease, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer) in combination with an effective (i.e., therapeutically effective) amount of one or more additional therapeutic agents useful for treating Alzheimer's disease to a patient in need of treatment.

In one embodiment, the invention provides a method of treating Alzheimer's disease, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer), in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e, donepezil hydrochloride, available as the Aricept® brand of donepezil hydrochloride), to a patient in need of treatment.

In one embodiment, the invention provides a method of treating Alzheimer's disease, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer), in combination with an effective (i.e., therapeutically effective) amount of one or more compounds selected from the group consisting of Aβ antibody inhibitors, gamma secretase inhibitors, gamma secretase modulators, and beta secretase inhibitors other than a compound of the invention.

In one embodiment, the invention provides a method of treating Alzheimer's disease, comprising administering an effective amount of one or more (e.g., one) compounds of the invention (or a tautomer or stereoisomer thereof, or pharmaceutically acceptable salt or solvate of said compound, said stereoisomer, or said tautomer), in combination with an effective amount of one or more compounds selected from the group consisting of Aβ antibody inhibitors, gamma secretase inhibitors, gamma secretase modulators, and beta secretase inhibitors.

In one embodiment, the invention provides a method of treating Alzheimer's disease, comprising administering an effective amount of one or more (e.g., one) compounds of the invention (or a tautomer or stereoisomer thereof, or pharmaceutically acceptable salt or solvate of said compound, said stereoisomer, or said tautomer), in combination with an effective amount of one or more BACE inhibitors.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of Exelon (rivastigmine).

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of Cognex (tacrine).

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of a Tau kinase inhibitor.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more Tau kinase inhibitor (e.g., GSK3beta inhibitor, cdk5 inhibitor, ERK inhibitor).

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one anti-Abeta vaccination (active immunization).

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more APP ligands.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more agents that upregulate insulin degrading enzyme and/or neprilysin.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe).

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more fibrates (for example, clofibrate, Clofibride, Etofibrate, Aluminium Clofibrate).

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more LXR agonists.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more MP mimics.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more 5-HT6 receptor antagonists.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more nicotinic receptor agonists.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more H3 receptor antagonists.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more histone deacetylase inhibitors.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more hsp90 inhibitors.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more m1 muscarinic receptor agonists.

Another embodiment of this invention is directed to a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more 5-HT6 receptor antagonists, or mGluR1, or mGluR5 positive allosteric modulators or agonists.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more mGluR2/3 antagonists.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more anti-inflammatory agents that can reduce neuroinflammation.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more Prostaglandin EP2 receptor antagonists.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more PAI-1 inhibitors.

In one embodiment, the invention provides a method of treating Alzheimer's disease, comprising administering an effective amount of one or more compounds of the invention (or a tautomer or stereoisomer thereof, or pharmaceutically acceptable salt or solvate of said compound, said stereoisomer, or said tautomer), in combination with an effective amount of one or more agents that can induce Abeta efflux such as gelsolin.

In one embodiment, the invention provides a method of treating Down's syndrome, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating Down's syndrome, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer), in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e, donepezil hydrochloride, available as the Aricept® brand of donepezil hydrochloride), to a patient in need of treatment.

In one embodiment, the invention provides a method of treating mild cognitive impairment, comprising administering an effective amount of one or more (e.g., one) compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating mild cognitive impairment, comprising administering an effective amount of one or more (e.g., one) compounds of the invention (or a tautomer or stereoisomer thereof, or pharmaceutically acceptable salt or solvate of said compound, said stereoisomer, or said tautomer), and an effective amount of one or more additional therapeutic agents suitable for use in such patients, to a patient in need of treatment.

In one embodiment, the invention provides a method of treating glaucoma, comprising administering an effective amount of one or more (e.g., one) compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating glaucoma, comprising administering an effective amount of one or more (e.g., one) compounds of the invention (or a tautomer or stereoisomer thereof, or pharmaceutically acceptable salt or solvate of said compound, said stereoisomer, or said tautomer), and an effective amount of one or more additional therapeutic agents suitable for use in such patients, to a patient in need of treatment.

In one embodiment, the invention provides a method of treating cerebral amyloid angiopathy, comprising administering an effective amount of one or more (e.g., one) compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating cerebral amyloid angiopathy, comprising administering an effective amount of one or more (e.g., one) compounds of the invention (or a tautomer or stereoisomer thereof, or pharmaceutically acceptable salt or solvate of said compound, said stereoisomer, or said tautomer), and an effective amount of one or more additional therapeutic agents suitable for use in such patients, to a patient in need of treatment.

In one embodiment, the invention provides a method of treating stroke, comprising administering an effective amount of one or more (e.g., one) compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating stroke, comprising administering an effective amount of one or more (e.g., one) compounds of the invention (or a tautomer or stereoisomer thereof, or pharmaceutically acceptable salt or solvate of said compound, said stereoisomer, or said tautomer), and an effective amount of one or more additional therapeutic agents suitable for use in such patients, to a patient in need of treatment.

In one embodiment, the invention provides a method of treating dementia, comprising administering an effective amount of one or more (e.g., one) compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating dementia, comprising administering an effective amount of one or more (e.g., one) compounds of the invention (or a tautomer or stereoisomer thereof, or pharmaceutically acceptable salt or solvate of said compound, said stereoisomer, or said tautomer), and an effective amount of one or more additional therapeutic agents suitable for use in such patients, to a patient in need of treatment.

In one embodiment, the invention provides a method of treating microgliosis, comprising administering an effective amount of one or more (e.g., one) compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating microgliosis, comprising administering an effective amount of one or more (e.g., one) compounds of the invention (or a tautomer or stereoisomer thereof, or pharmaceutically acceptable salt or solvate of said compound, said stereoisomer, or said tautomer), and an effective amount of one or more additional therapeutic agents suitable for use in such patients, to a patient in need of treatment.

In one embodiment, the invention provides a method of treating brain inflammation, comprising administering an effective amount of one or more (e.g., one) compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating brain inflammation, comprising administering an effective amount of one or more (e.g., one) compounds of the invention (or a tautomer or stereoisomer thereof, or pharmaceutically acceptable salt or solvate of said compound, said stereoisomer, or said tautomer), and an effective amount of one or more additional therapeutic agents suitable for use in such patients, to a patient in need of treatment.

In one embodiment, the invention provides a method of treating traumatic brain injury, comprising administering an effective amount of one or more (e.g., one) compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating olfactory function loss, comprising administering an effective amount of one or more (e.g., one) compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating olfactory function loss, comprising administering an effective amount of one or more (e.g., one) compounds of the invention (or a tautomer or stereoisomer thereof, or pharmaceutically acceptable salt or solvate of said compound, said stereoisomer, or said tautomer), and an effective amount of one or more additional therapeutic agents suitable for use in such patients, to a patient in need of treatment.

In one embodiment, the invention provides a kit comprising, in separate containers, in a single package, pharmaceutical compositions for use in combination, wherein one container comprises an effective amount of a compound of the invention (or a tautomer or stereoisomer thereof, or pharmaceutically acceptable salt or solvate of said compound, said stereoisomer, or said tautomer) in a pharmaceutically acceptable carrier, and another container (i.e., a second container) comprises an effective amount of another pharmaceutically active ingredient, the combined quantities of the compound of the invention and the other pharmaceutically active ingredient being effective to: (a) treat Alzheimer's disease, or (b) inhibit the deposition of amyloid protein in, on or around neurological tissue (e.g., the brain), or (c) treat neurodegenerative diseases, or (d) inhibit the activity of BACE-1.

In one embodiment, the invention provides a kit comprising, in separate containers, in a single package, pharmaceutical compositions for use in combination, wherein one container comprises an effective amount of a compound of the invention (or a tautomer or stereoisomer thereof, or pharmaceutically acceptable salt or solvate of said compound, said stereoisomer, or said tautomer) in a pharmaceutically acceptable carrier, and another container (i.e., a second container) comprises an effective amount of another pharmaceutically active ingredient (as described below), the combined quantities of the compound of the invention and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) inhibit the activity of BACE-1.

In various embodiments, the invention provides any one of the methods disclosed above and below wherein the compound(s) of the invention is a compound or compounds selected from the group consisting of the exemplary compounds of the invention described below.

In various embodiments, the invention provides any one of the pharmaceutical compositions disclosed above and below wherein the compound(s) of the invention is a compound or compounds selected from the group consisting of the exemplary compounds of the invention described below.

Other embodiments of this invention are directed to any one of the embodiments above or below that are directed to compounds of the invention, or the use of compounds of the invention (e.g. the embodiments directed to methods of treatment, pharmaceutical compositions and kits).

In another embodiment, the invention provides for the use of a compound of the invention, or a tautomer or stereoisomer thereof, or pharmaceutically acceptable salt or solvate of said compound, said stereoisomer, or said tautomer, in the manufacture of a medicament for use in the treatment, the delay of onset, and/or the prevention of one or more Aβ pathologies and/or in the treatment, the delay of onset, and/or the prevention of one or more symptoms of one or more Aβ pathologies.

In another embodiment, the invention provides a kit comprising: (a) one or more compounds of the invention, or a tautomer or stereoisomer thereof, or pharmaceutically acceptable salt or solvate of said compound, said stereoisomer, or said tautomer, preferably provided as a pharmaceutical composition and in a suitable container or containers and/or with suitable packaging; (b) optionally one or more additional active agents, which if present are preferably provided as a pharmaceutical composition and in a suitable container or containers and/or with suitable packaging; and (c) instructions for use, for example written instructions on how to administer the compound or compositions.

In another embodiment, the invention provides a kit comprising a single container or multiple containers: (a) a pharmaceutically acceptable composition comprising one or more compounds of claim 1, or a tautomer or stereoisomer thereof, or pharmaceutically acceptable salt or solvate of said compound, said stereoisomer, or said tautomer, (b) optionally pharmaceutically acceptable composition comprising one or more additional therapeutic agents; and (c) instructions for use their use. Said kit may optionally comprise labeling appropriate to the intended use or uses.

Definitions

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

It shall be understood that, in the various embodiments of the invention described herein, any variable not specifically defined in the context of the embodiment is as defined in Formula (I). All valences not explicitly filled are assumed to be filled by hydrogen.

As described herein, variables such as $R^1$, $R^2$, and $R^3$ may be unsubstituted or substituted with one or more $R^4$ groups. It shall be understood that the upper limit of the number of substituents (referred to in the phrase "one or more substituents") is the number of available hydrogen atoms on the relevant moiety ($R^1$, $R^2$, or $R^3$) that are available for replacement by a substituent which will result in a chemically stable moiety.

As described herein, one or more of the variables of the general formulae representing the various embodiments of the compounds of the invention (e.g., variables -$L_1$-, -$L_2$-, and -$L_3$-) optionally independently present or absent. It shall be understood that where such a is absent, the moieties which are shown connected by that variable are directly attached. Thus, by way of non-limiting illustration only, a compound of Formula (I) wherein -$L_1$-, -$L_2$-, -$L_3$-, and -$L_4$- are each absent is understood to be depicted as:

The moiety which may be optionally substituted as described herein, represents a ring referred to herein as "ring A."

The moiety which may be optionally substituted as described herein, represents a ring referred to herein as "ring B."

The moiety which may be optionally substituted as described herein, represents a ring referred to herein as "ring C."

In the various Formulas of the compounds of the invention, e.g., in Formula (I), m, n, p, q, r, s, and t are each independently selected integers, wherein:
m is 0 or more,
n is 0 or more,
p is 0 or more,
q is 0 or more,
r is 0, 1, or 2,
s is 0, 1, or 2, and
t is 0, 1, or 2,
with the provisos that:
(i) the maximum value of the sum of m, q, and s is the maximum number of available substitutable hydrogen atoms on ring A,
(ii) the maximum value of the sum of n and r is the maximum number of available substitutable hydrogen atoms on ring B, and
(iii) the maximum value of the sum of p and t is the maximum number of available substitutable hydrogen atoms on ring C, and
(iv) the sum of r, s, and t is 1 or 2.

Except for salt forms, the "maximum number of substitutable hydrogen atoms" refers to the maximum number that will result in a neutral molecule. By way of non-limiting illustration, when ring A is a phenyl group, the minimum value of the sum of m, s, and q is 0 and the maximum value of m the sum of m, s, and q is 5. When ring A is a group, the minimum value of the sum of m, s, and q is 0 and the maximum value of m, s, and q is 4.

In one embodiment, in Formula (I), m, n, p, q, r, s, and t are each independently selected integers, wherein:
m is 0 or more,
n is 0 or more,
p is 0 or more,
q is 0 or more,
r is 0, 1, or 2
s is 0, 1, or 2,
t is 0, 1, or 2,
wherein the minimum value of the sum of m, s, and q is 0 and the maximum value of the sum of m, s, and q is 17,
the minimum value of the sum of p and t (when present) is 0 and the maximum value of the sum of p and t (when present) is 17, and
the minimum value of the sum of n and r is 0 and the maximum value of the sum of n and r is 17.

In the compounds of the invention, e.g., in Formula (I), each of ring A and ring B is independently selected from the group consisting of a monocyclic aryl, a monocyclic heteroaryl, a monocyclic cycloalkyl, a monocyclic cycloalkenyl, a monocyclic heterocycloalkyl, a monocyclic heterocycloalkenyl, and a multicyclic group, each of which groups may be unsubstituted or optionally further substituted as shown.

As used herein, the term "monocyclic aryl" refers to phenyl.

As used herein, the term "monocyclic heteroaryl" refers to a 4- to 7-membered monocyclic heteroaryl group comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moieties include pyridyl, pyrazinyl, furanyl, thienyl, pyrimidinyl, pyridazinyl, pyridone, thiazolyl, isothiazolyl, oxazolyl, isoxazolyl, pyrazolyl, furazanyl, pyrrolyl, pyrazolyl, triazolyl, thiadiazolyl (e.g., 1,2,4-thiadiazolyl), pyrazinyl, pyridazinyl, imidazolyl, and triazinyl (e.g., 1,2,4-triazinyl), and oxides thereof.

As used herein, the term "monocyclic cycloalkyl" refers to a 3- to 7-membered monocyclic cycloalkyl group. Non-limiting examples of monocyclic cycloalkyl groups include cyclopropyl, cyclobutyl, cyclopentyl, cyclohexyl, and cycloheptyl.

As used herein, the term "monocyclic cycloalkenyl" refers to a non-aromatic 3- to 7-membered cycloalkyl group which contains one or more carbon-carbon double bonds. Non-limiting examples include cyclopropenyl, cyclobutenyl, cyclopentenyl, cyclohexenyl, and cycloheptenyl.

As used herein, the term "monocyclic heterocycloalkyl" refers to a 4- to 7-membered monocyclic heterocycloalkyl group comprising from 1 to 4 ring heteroatoms, said ring heteroatoms being independently selected from the group consisting of N,N-oxide, O, S, S-oxide, S(O), and S(O)₂. The point of attachment to the parent moiety is to any available ring carbon or ring heteroatom. Non-limiting examples of monocyclic heterocycloalkyl groups include piperidyl, oxetanyl, pyrrolidinyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof.

Non-limiting examples of lower alkyl-substituted oxetanyl include the moiety:

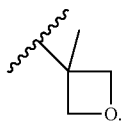

As used herein, the term "monocyclic heterocycloalkenyl" refers to a 4- to 7-membered monocyclic heterocycloalkenyl group comprising from 1 to 4 ring heteroatoms, said ring heteroatoms being independently selected from the group consisting of N,N-oxide, O, S, S-oxide, S(O), and S(O)₂. The point of attachment to the parent moiety is to any available ring carbon or ring heteroatom. Non-limiting examples of monocyclic heterocyloalkenyl groups include 1,2,3,4- tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, dihydrothiophenyl, and dihydrothiopyranyl, and oxides thereof.

As used herein, the term "multicyclic group" refers to a fused ring system comprising two (bicyclic), three (tricyclic), or more fused rings, wherein each ring of the fused ring system is independently selected from the group consisting of phenyl, monocyclic heteroaryl, monocyclic cycloalkyl, monocyclic cycloalkenyl, monocyclic heterocycloalkyl, and monocyclic heterocycloalkenyl. The point of attachment to the parent moiety is to any available ring carbon or (if present) ring heteroatom on any of the fused rings.

It shall be understood that each of the following multicyclic groups pictured may be unsubstituted or substituted, as described herein. Only the point of attachment to the parent moiety is shown by the wavy line.

The term multicyclic groups includes bicyclic aromatic groups. Non-limiting examples of multicyclic groups which are bicyclic aromatic groups include:

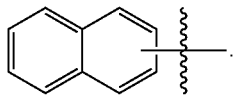

The term multicyclic groups includes bicyclic heteroaromatic groups comprising from 1 to 3 or more ring heteroatoms, each said ring heteroatom being independently selected from the group consisting of N, O, and S, S(O), S(O)₂, and oxides of N, O, and S, and oxides thereof. Non-limiting examples of multicyclic groups which are bicyclic heteroaromatic groups comprising from 1 to 3 ring heteroatoms, each said ring heteroatom being independently selected from N, O, and S include the following, and oxides thereof:

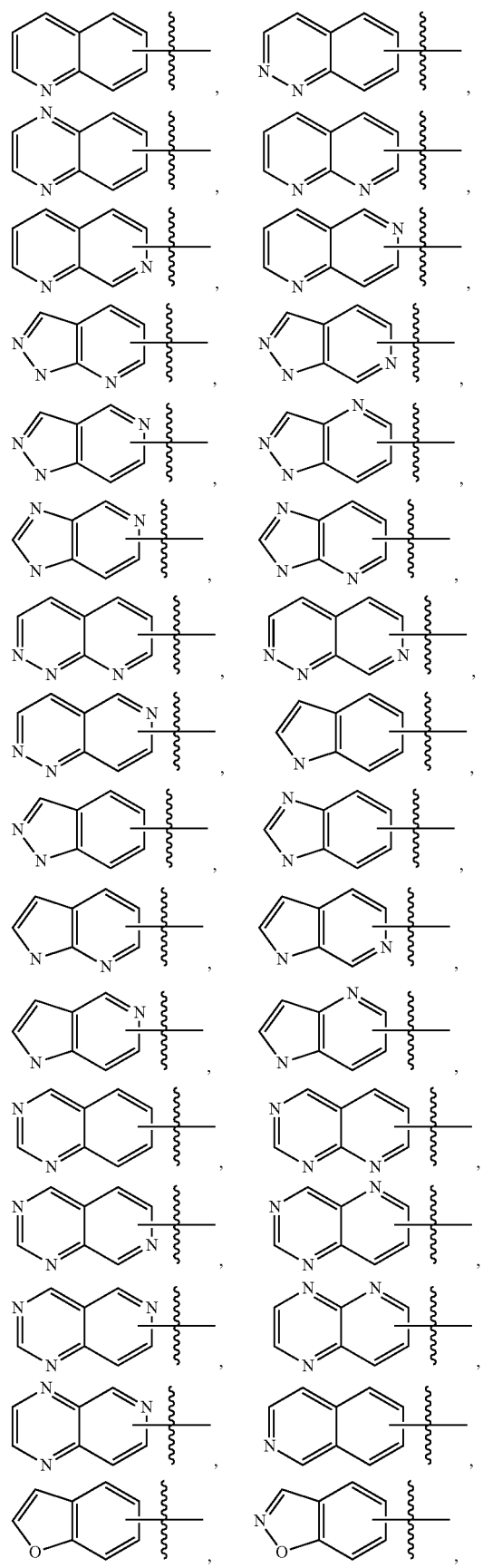

-continued

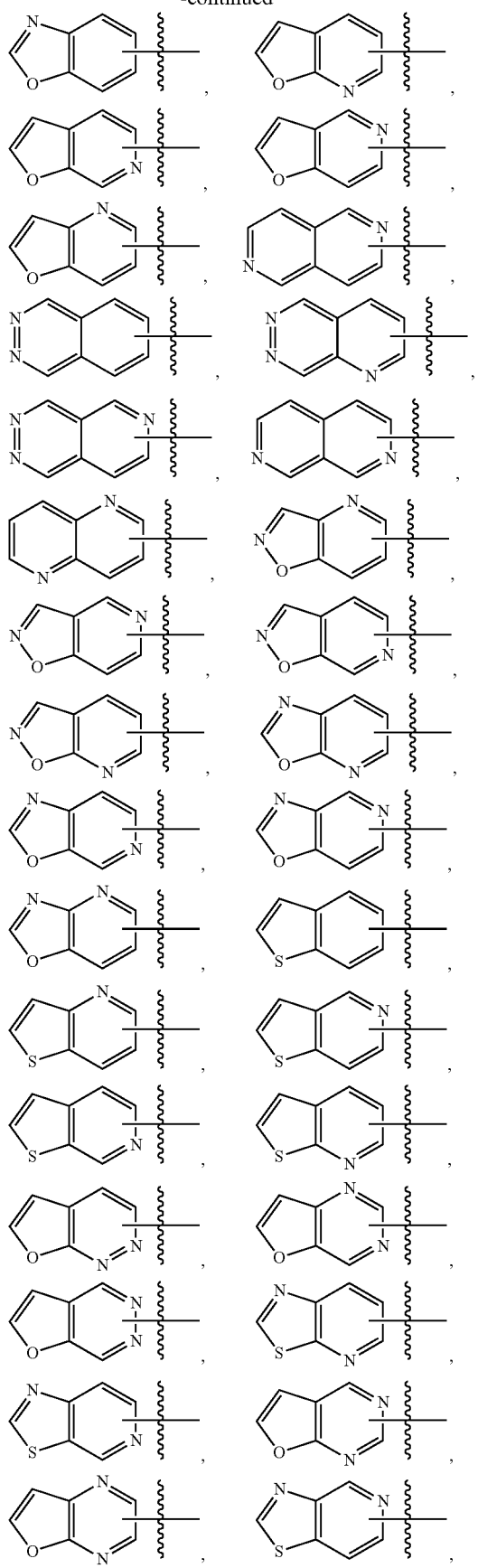

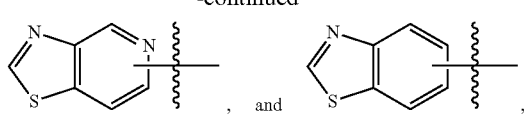

, and

The term multicyclic groups includes saturated bicyclic cycloalkyl groups. Non-limiting examples of multicyclic groups which are saturated bicyclic cycloalkyl groups include the following:

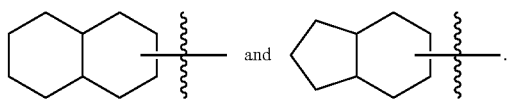

and

The term multicyclic group includes partially unsaturated bicyclic cycloalkyl groups. Non-limiting examples of multicyclic groups which comprise partially unsaturated bicyclic cycloalkyl groups include the following:

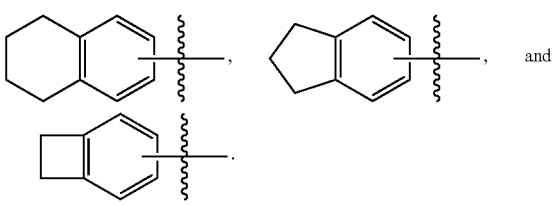

, and

The term multicyclic groups includes partially or fully saturated bicyclic groups comprising from 1 to 3 ring heteroatoms, each said ring heteroatom is independently selected from the group consisting of N, O, and S, S(O), S(O)$_2$, and oxides of N and S. Such rings may also optionally contain one or more oxo groups, as defined herein. Non-limiting examples of multicyclic groups which are partially or fully saturated bicyclic groups comprising from 1 to 3 ring heteroatoms, each said ring heteroatom being independently selected from N, O, and S include the following, and oxides thereof:

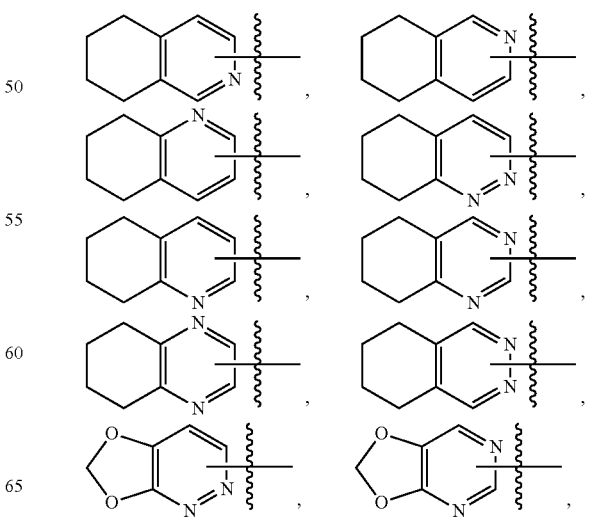

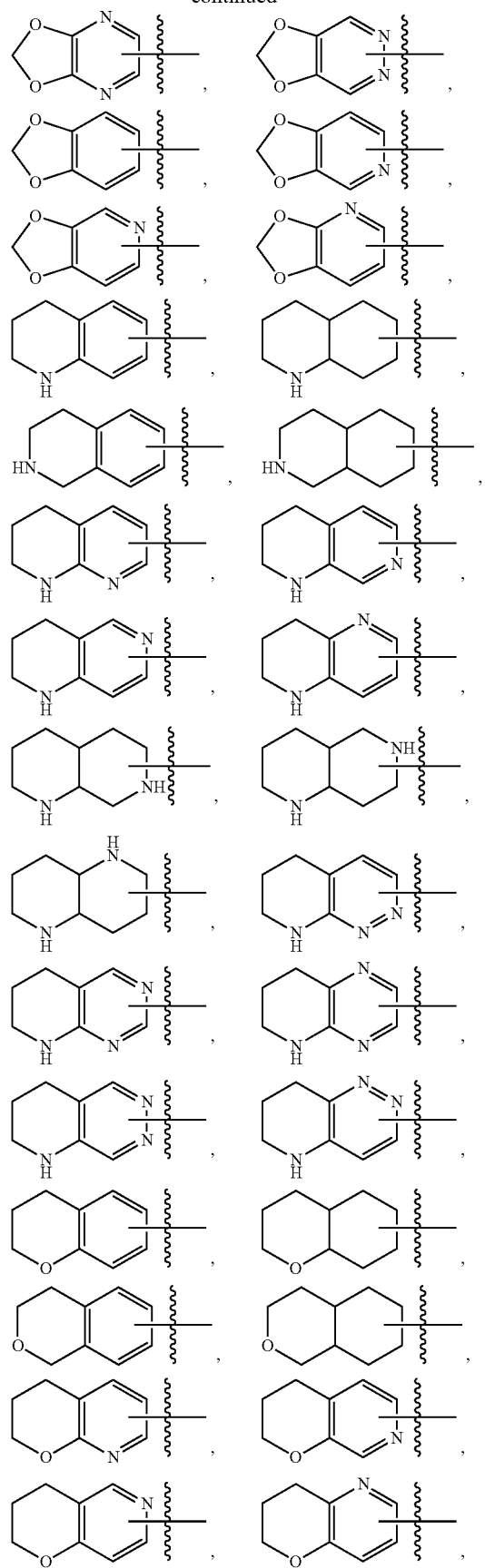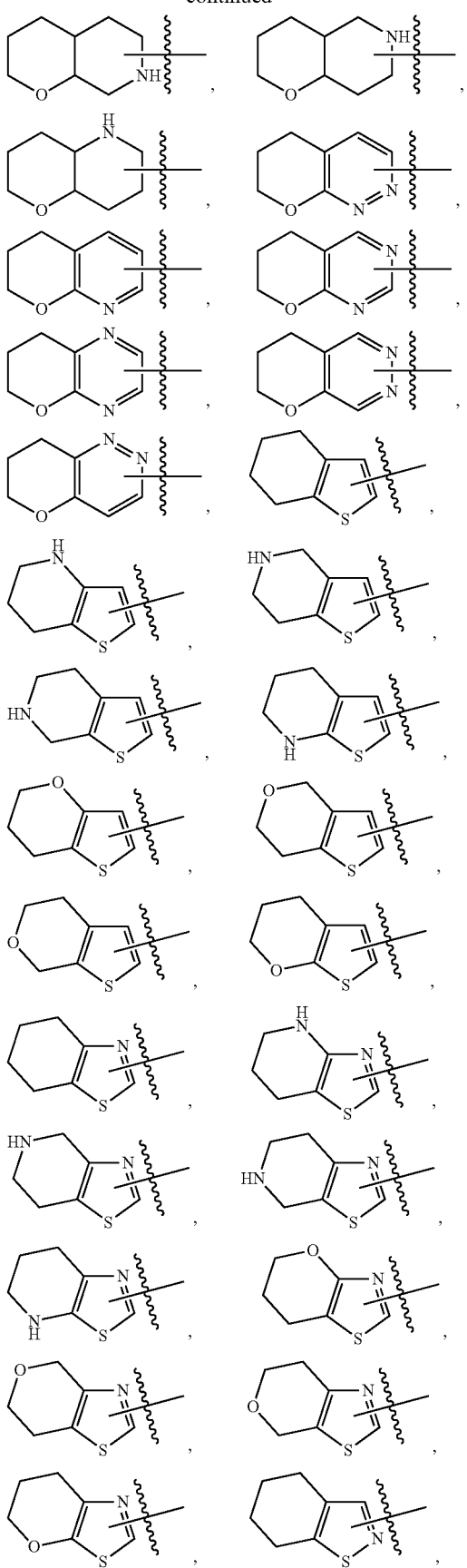

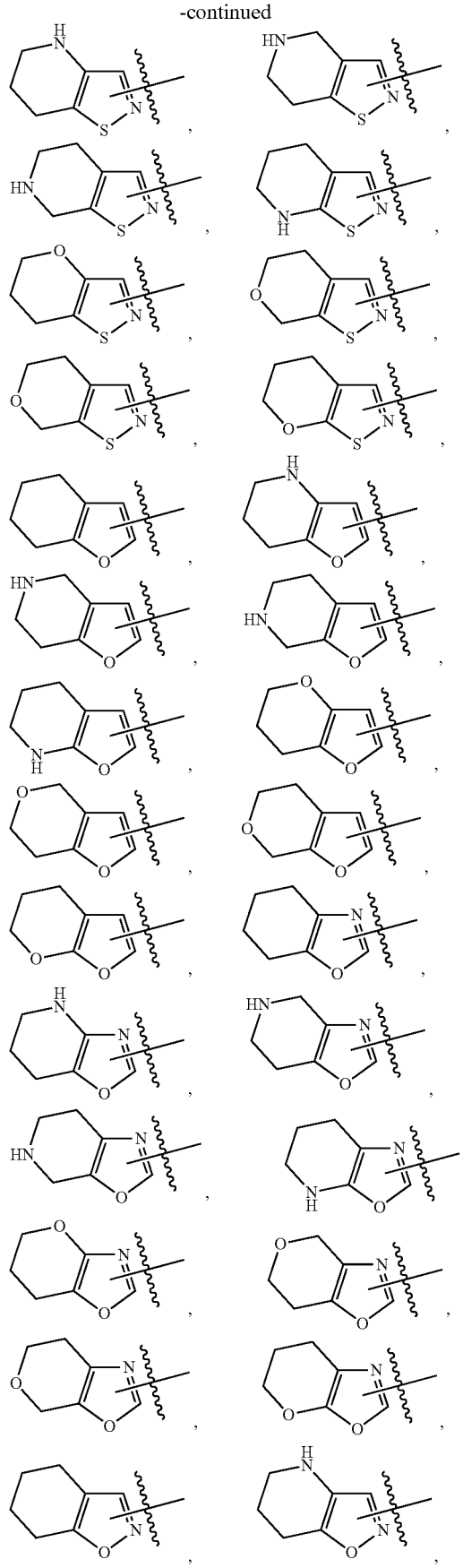
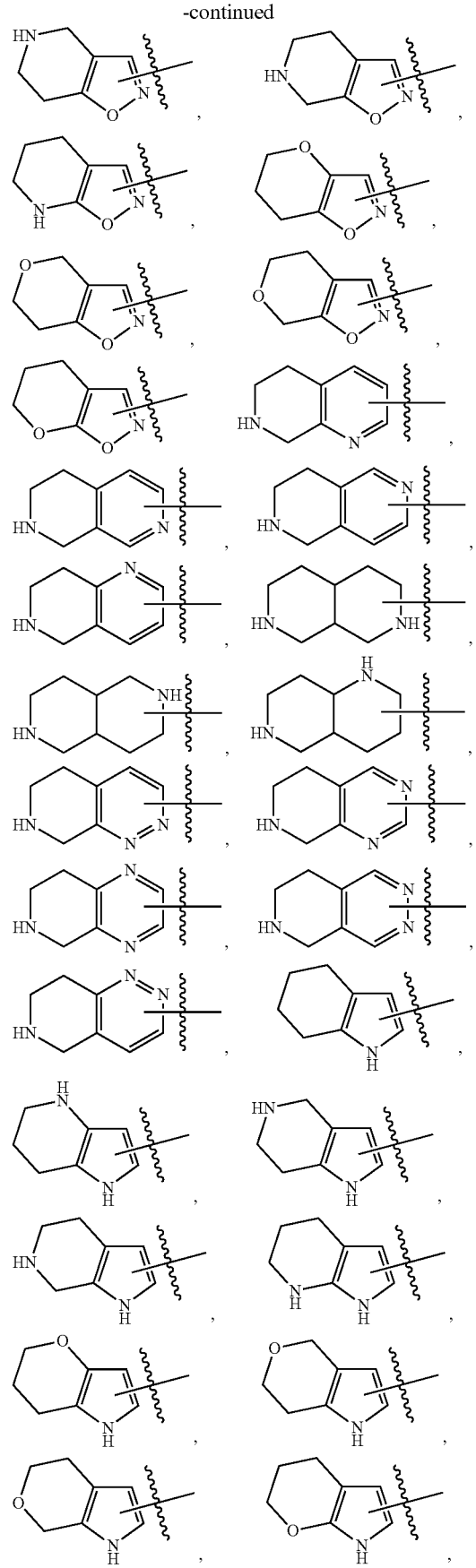

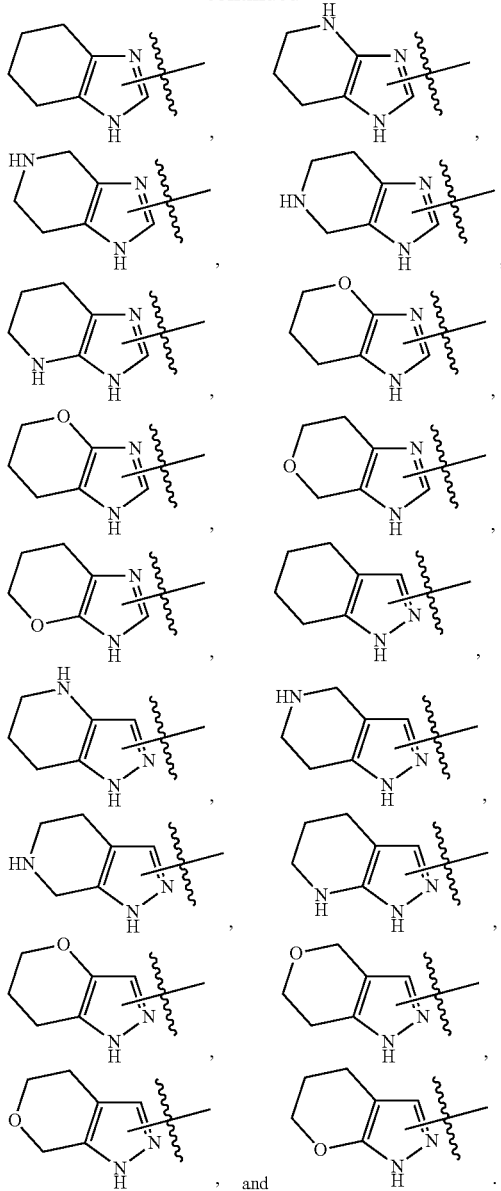

The term multicyclic groups includes aromatic tricyclic groups, cycloalkyl tricyclic groups, as well as heteroaromatic and partially and fully saturated tricyclic groups. For tricyclic groups comprising ring heteroatoms, said tricyclic groups comprise one or more (e.g., from 1 to 5) ring heteroatoms, wherein each said ring heteroatom is independently selected from N, O, and S, S(O), S(O)$_2$, and oxides of N, O, and S: Non-limiting examples of tricyclic multicyclic groups include the following, and, where possible, oxides thereof:

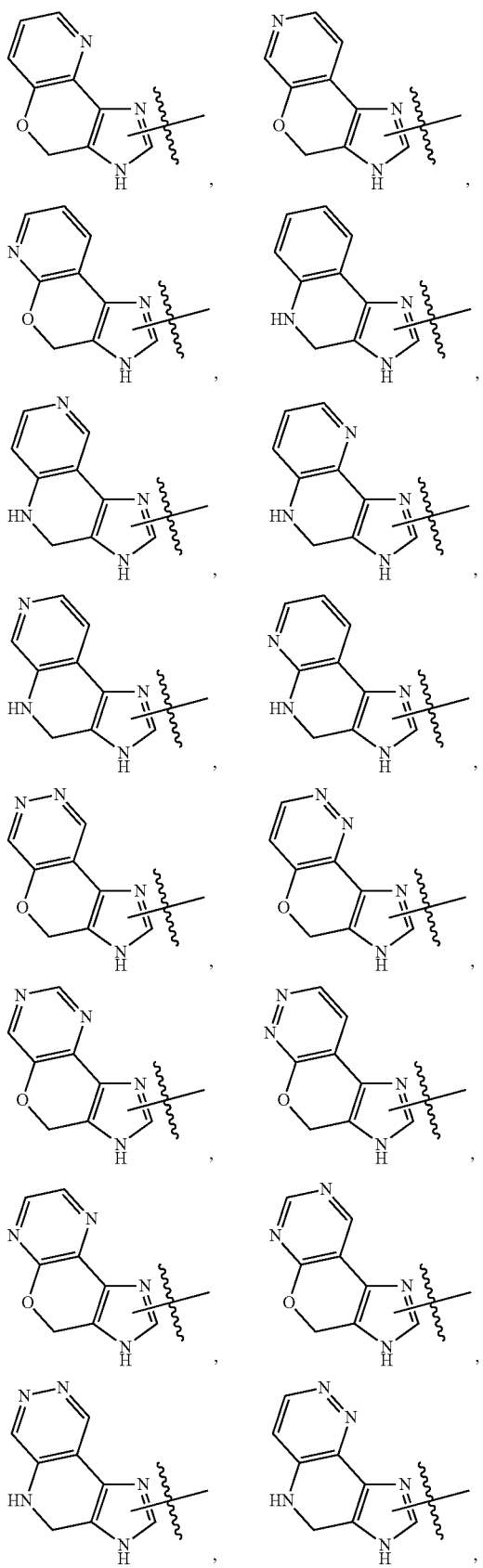

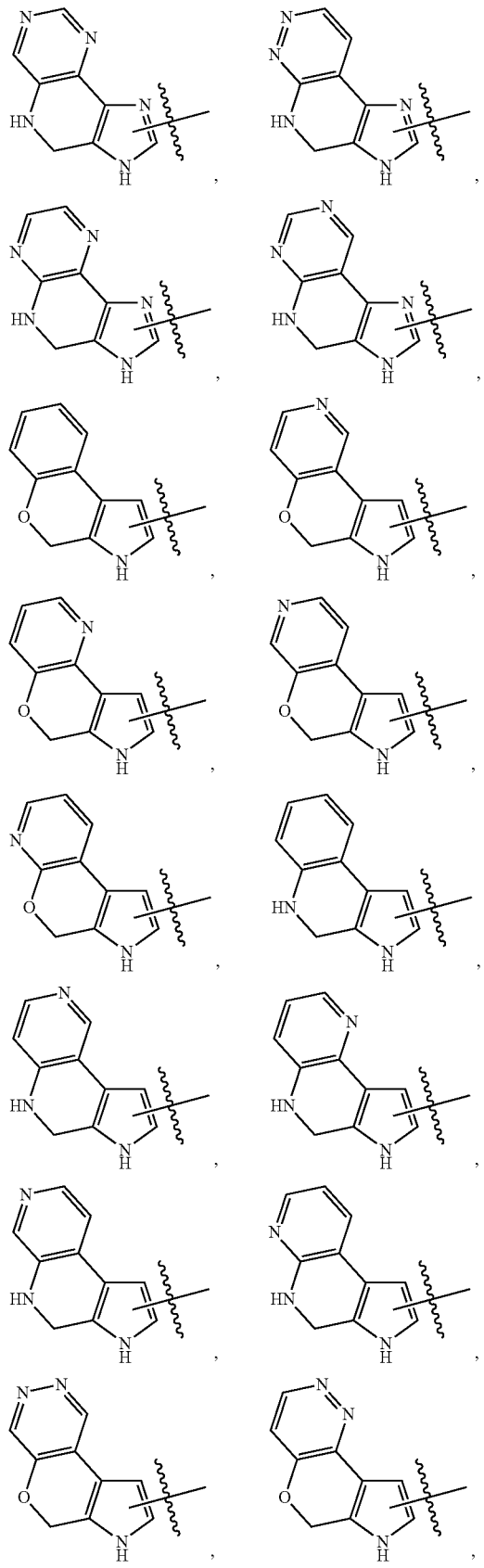
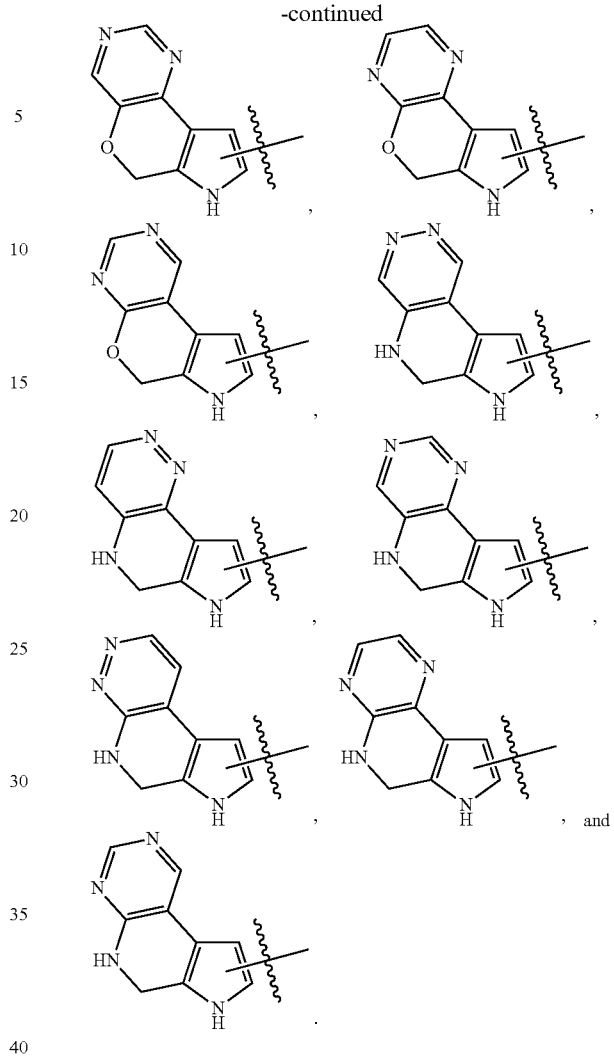

"Patient" includes both human and non-human animals. Non-human animals include those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the aforesaid "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the aforesaid bulk composition and individual dosage units.

"Halogen" means fluorine, chlorine, bromine, or iodine. Preferred are fluorine, chlorine and bromine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being as described herein or independently selected from the group consisting of halo, alkyl, haloalkyl, spirocycloalkyl, aryl, cycloalkyl, cyano, hydroxy, alkoxy, alkylthio, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Haloalkyl" means an alkyl as defined above wherein one or more hydrogen atoms on the alkyl is replaced by a halo group defined above.

"Heteroalkyl" means an alkyl moiety as defined above, having one or more carbon atoms, for example one, two or three carbon atoms, replaced with one or more heteroatoms, which may be the same or different, where the point of attachment to the remainder of the molecule is through a carbon atom of the heteroalkyl radical. Suitable such heteroatoms include O, S, S(O), S(O)$_2$, and —NH—, —N(alkyl)-. Non-limiting examples include ethers, thioethers, amines, hydroxymethyl, 3-hydroxypropyl, 1,2-dihydroxyethyl, 2-methoxyethyl, 2-aminoethyl, 2-dimethylaminoethyl, and the like.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene. More generally, the suffix "ene" on alkyl, aryl, heterocycloalkyl, etc. indicates a divalent moiety, e.g., —CH$_2$CH$_2$— is ethylene, and

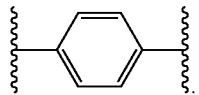 [SMILES: *c1ccc(*)cc1]

is para-phenylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Alkenylene" means a difunctional group obtained by removal of a hydrogen from an alkenyl group that is defined above. Non-limiting examples of alkenylene include —CH═CH—, —C(CH$_3$)═CH—, and —CH═CHCH$_2$—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (alternatively referred to herein as thiophenyl), pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined herein. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like. Further non-limiting examples of cycloalkyl include the following:

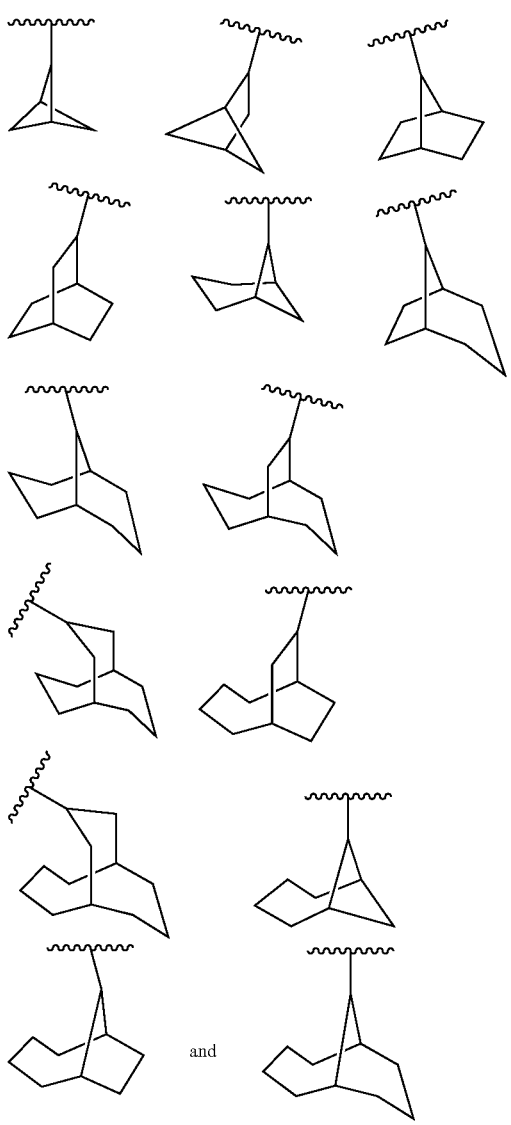

and

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

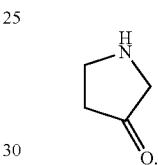

"Heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes rings wherein =O replaces two available hydrogens on the same carbon atom (i.e., heterocyclyl includes rings having a carbonyl group in the ring). Example of such moiety is pyrrolidenone (or pyrrolone):

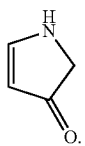

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

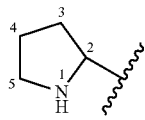

there is no —OH attached directly to carbons marked 2 and 5.

It should also be noted that tautomeric forms of the compounds of the invention are also contemplated as being within the scope of the invention. Thus, for example, the formulas:

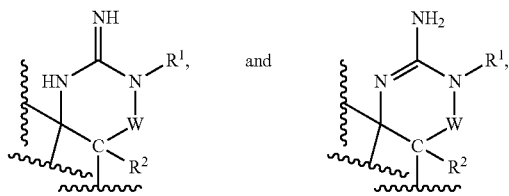

are considered equivalent in the various compounds of the invention.

"Arylcycloalkyl" (or "arylfused cycloalkyl") means a group derived from a fused aryl and cycloalkyl as defined herein. Preferred arylcycloalkyls are those wherein aryl is phenyl (which may be referred to as "benzofused") and cycloalkyl consists of about 5 to about 6 ring atoms. The arylcycloalkyl can be optionally substituted as described herein. Non-limiting examples of suitable arylcycloalkyls include indanyl (a benzofused cycloalkyl) and 1,2,3,4-tetrahydronaphthyl and the like. The bond to the parent moiety is through a non-aromatic carbon atom.

"Arylheterocycloalkyl" (or "arylfused heterocycloalkyl") means a group derived from a fused aryl and heterocycloalkyl as defined herein. Preferred arylheterocycloalkyls are those wherein aryl is phenyl (which may be referred to as "benzofused") and heterocycloalkyl consists of about 5 to about 6 ring atoms. The arylheterocycloalkyl can be optionally substituted, and/or contain the oxide or oxo, as described herein. Non-limiting examples of suitable arylfused heterocycloalkyls include:

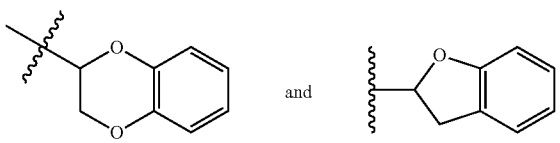 [SMILES: *C1COc2ccccc2O1 ; *C1Cc2ccccc2O1]

The bond to the parent moiety is through a non-aromatic carbon atom.

It is also understood that the terms "arylfused aryl", "arylfused cycloalkyl", "arylfused cycloalkenyl", "arylfused heterocycloalkyl", arylfused heterocycloalkenyl", "arylfused heteroaryl", "cycloalkylfused aryl", "cycloalkylfused cycloalkyl", "cycloalkylfused cycloalkenyl", "cycloalkylfused heterocycloalkyl", "cycloalkylfused heterocycloalkenyl", "cycloalkylfused heteroaryl, "cycloalkenylfused aryl", "cycloalkenylfused cycloalkyl", "cycloalkenylfused cycloalkenyl", "cycloalkenylfused heterocycloalkyl", "cycloalkenylfused heterocycloalkenyl", "cycloalkenylfused heteroaryl", "heterocycloalkylfused aryl", "heterocycloalkylfused cycloalkyl", "heterocycloalkylfused cycloalkenyl", "heterocycloalkylfused heterocycloalkyl", "heterocycloalkylfused heterocycloalkenyl", "heterocycloalkylfused heteroaryl", "heterocycloalkenylfused aryl", "heterocycloalkenylfused cycloalkyl", "heterocycloalkenylfused cycloalkenyl", "heterocycloalkenylfused heterocycloalkyl", "heterocycloalkenylfused heterocycloalkenyl", "heterocycloalkenylfused heteroaryl", "heteroarylfused aryl", "heteroarylfused cycloalkyl", "heteroarylfused cycloalkenyl", "heteroarylfused heterocycloalkyl", "heteroarylfused heterocycloalkenyl", and "heteroarylfused heteroaryl" are similarly represented by the combination of the groups aryl, cycloalkyl, cycloalkenyl, heterocycloalkyl, heterocycloalkenyl, and heteroaryl, as previously described. Any such groups may be unsubstituted or substituted with one or more ring system substituents at any available position as described herein.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl. The term (and similar terms) may be written as "arylalkyl-" to indicate the point of attachment to the parent moiety.

Similarly, "heteroarylalkyl", "cycloalkylalkyl", "cycloalkenylalkyl", "heterocycloalkylalkyl", "heterocycloalkenylalkyl", etc., mean a heteroaryl, cycloalkyl, cycloalkenyl, heterocycloalkyl, heterocycloalkenyl, etc. as described herein bound to a parent moiety through an alkyl group. Preferred groups contain a lower alkyl group. Such alkyl groups may be straight or branched, unsubstituted and/or substituted as described herein.

Similarly, "arylfused arylalkyl-", arylfused cycloalkylalkyl-, etc., means an arylfused aryl group, arylfused cycloalkyl group, etc. linked to a parent moiety through an alkyl group. Preferred groups contain a lower alkyl group. Such alkyl groups may be straight or branched, unsubstituted and/or substituted as described herein.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloakether" means a non-aromatic ring of 3 to 7 members comprising an oxygen atom and 2 to 7 carbon atoms. Ring carbon atoms can be substituted, provided that substituents adjacent to the ring oxygen do not include halo or substituents joined to the ring through an oxygen, nitrogen or sulfur atom.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl, adamantylpropyl, and the like.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclylalkyl" (or "heterocycloalkylalkyl") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenylalkyl" means a heterocyclenyl moiety as defined above linked via an alkyl moiety (defined above) to a parent core.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Cyanoalkyl" means a NC-alkyl- group in which alkyl is as previously defined. Preferred cyanoalkyls contain lower alkyl. Non-limiting examples of suitable cyanoalkyl groups include cyanomethyl and 2-cyanoethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1- naphthoyl.

"Heteroaroyl" means an heteroaryl-C(O)— group in which the heteroaryl group is as previously described. The bond to the parent moiety is through the carbonyl. Non-limiting examples of suitable groups include pyridoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkyoxyalkyl" means a group derived from an alkoxy and alkyl as defined herein. The bond to the parent moiety is through the alkyl.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" (or "arylalkyloxy") means an aralkyl-O— group (an arylaklyl-O— group) in which the aralkyl group is as previously described. Non-limiting examples of suitable aralkyloxy groups include benzyloxy and 1- or 2-naphthalenemethoxy. The bond to the parent moiety is through the ether oxygen.

"Arylalkenyl" means a group derived from an aryl and alkenyl as defined herein. Preferred arylalkenyls are those wherein aryl is phenyl and the alkenyl consists of about 3 to about 6 atoms. The arylalkenyl can be optionally substituted by one or more substituents. The bond to the parent moiety is through a non-aromatic carbon atom.

"Arylalkynyl" means a group derived from a aryl and alkenyl as defined herein. Preferred arylalkynyls are those wherein aryl is phenyl and the alkynyl consists of about 3 to about 6 atoms. The arylalkynyl can be optionally substituted by one or more substituents. The bond to the parent moiety is through a non-aromatic carbon atom.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

"Spirocycloalkyl" means a cycloalkyl group attached to a parent moiety at a single carbon atom. Non-limiting examples of spirocycloalkyl wherein the parent moiety is a cycloalkyl include Spiro[2.5]octane, spiro[2.4]heptane, etc. Non-limiting examples of spirocycloalkyl wherein the parent moiety is an The alkyl moiety linking fused ring systems (such as the alkyl moiety in heteroarylfused heteroarylalkyl-) may optionally be substituted with spirocycloalkyl or other groups as described herein. Non-limiting spirocycloalkyl groups include spirocyclopropyl, spriorcyclobutyl, spirocycloheptyl, and spirocyclohexyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl- moiety or the like includes substitution on any ring portion and/or on the alkyl portion of the group.

When a variable appears more than once in a group, e.g., $R^8$ in —$N(R^8)_2$, or a variable appears more than once in a structure presented herein, the variables can be the same or different.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art. With respect to the compositions and methods comprising the use of "at least one compound of the invention, e.g., of Formula (II)," one to three compounds of the invention, e.g., of Formula (II) can be administered at the same time, preferably one.

Compounds of the invention may contain one or more rings having one or more ring system substituents. "Ring system substituent" means a substituent attached to an aromatic or non-aromatic ring system which, for example, replaces an available hydrogen on the ring system. Ring system substituents may be the same or different, each being as described herein or independently selected from the group consisting of alkyl, alkenyl, alkynyl, haloalkyl, heteroalkyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—$NH_2$, —C(=NH)—$NH_2$, —C(=NH)—NH(alkyl), $Y_1Y_2$N—, $Y_1Y_2$N-alkyl-, $Y_1Y_2$NC(O)—, $Y_1Y_2NSO_2$— and —$SO_2NY_1Y_2$, wherein $Y_1$ and $Y_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moieties are rings such as heteroaryl, cycloalkyl, cycloalkenyl, heterocloalkyl, and heterocycloalkenyl rings. Additional non-limiting examples include methylene dioxy, ethylenedioxy, —$C(CH_3)_2$— and the like which form moieties such as, for example:

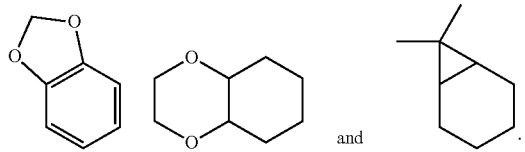

As used herein, the term "composition" is intended to encompass a product comprising the specified ingredients in the specified amounts, as well as any product which results, directly or indirectly, from combination of the specified ingredients in the specified amounts.

The line —, as a bond generally indicates a mixture of, or either of, the possible isomers, e.g., containing (R)- and (S)-stereochemistry. For example:

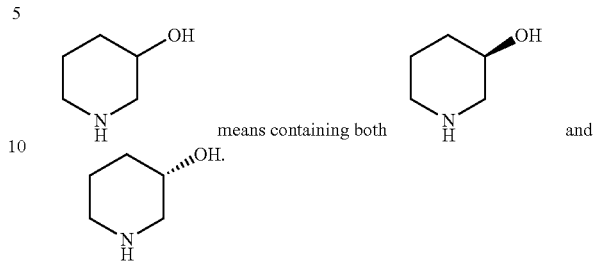

The wavy line ～, as used herein, indicates a point of attachment to the rest of the compound. For example, each wavy line in the following structure:

indicates a point of attachment to the core structure, as described herein.

Lines drawn into the ring systems, such as, for example:

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g., In this specification, where there are multiple oxygen and/or sulfur atoms in a ring system, there cannot be any adjacent oxygen and/or sulfur present in said ring system.

It is noted that the carbon atoms for compounds of the invention may be replaced with 1 to 3 silicon atoms so long as all valency requirements are satisfied.

As well known in the art, a bond drawn from a particular atom wherein no moiety is depicted at the terminal end of the bond indicates a methyl group bound through that bond to the atom, unless stated otherwise. For example:

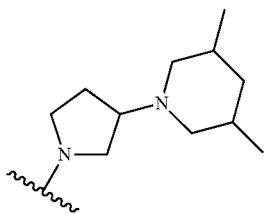 [SMILES: *N1CCC(N2CC(C)CC(C)C2)C1]

represents

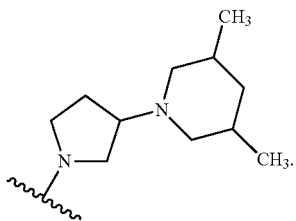 [SMILES: *N1CCC(N2CC(C)CC(C)C2)C1]

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer or stereoisomer thereof, or pharmaceutically acceptable salt or solvate of said compound, said stereoisomer, or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al., *Protective Groups in organic Synthesis* (1991), Wiley, New York.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-(C1-C2)alkyl and piperidino-, pyrrolidino- or morpholino$(C_2-C_3)$ alkyl, and the like.

Similarly, if a compound of the invention contains an alcohol functional group, a prodrug can be formed by the replacement of the hydrogen atom of the alcohol group with a group such as, for example, $(C_1-C_6)$alkanoyloxymethyl, 1-(($C_1-C_6$) alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, $—P(O)(O(C_1-C_6)alkyl)_2$ or glycosyl (the radical resulting from the removal of a hydroxyl group of the hemiacetal form of a carbohydrate), and the like.

If a compound of the invention incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, $—C(OH)C(O)OY^1$ wherein $Y^1$ is H, $(C_1-C_6)$alkyl or benzyl, $—C(OY^2)Y^3$ wherein $Y^2$ is $(C_1-C_4)$alkyl and $Y^3$ is $(C_1-C_6)$alkyl, carboxy $(C_1-C_6)$alkyl, amino $(C_1-C_4)$alkyl or mono-N— or di-N,N—$(C_1-C_6)$alkylaminoalkyl, $—C(Y^4)Y^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al., *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of the invention can form salts which are also within the scope of this invention. Reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the invention may be formed, for example, by reacting a compound of the invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl at al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of the invention, and salts, solvates, esters and prodrugs thereof, may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of the invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of the invention can generally be prepared by following procedures analogous to those disclosed in the Schemes and/or in the Examples hereinbelow, by substituting an appropriate isotopically labelled reagent for a non-isotopically labelled reagent. Non-limiting examples of deuterated compounds of the invention are described hereinbelow.

Polymorphic forms of the compounds of the invention, and of the salts, solvates, esters and prodrugs of the compounds of the invention, are intended to be included in the present invention.

Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

As discussed above, the amount and frequency of administration of the compounds of the invention and/or the pharmaceutically acceptable salts thereof will be regulated according to the judgment of the attending clinician considering such factors as age, condition and size of the patient as well as severity of the symptoms being treated.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, in an aspect, this invention includes combinations comprising an amount of at least one compound of the invention, or a pharmaceutically acceptable salt, solvate, ester or prodrug thereof, and an effective amount of one or more additional agents described above.

The pharmacological properties of the compounds of this invention may be confirmed by a number of pharmacological assays. Certain assays are exemplified elsewhere in this document.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

In one embodiment, the compound is administered orally.

In some embodiments, it may be advantageous for the pharmaceutical preparation comprising one or more compounds of the invention be prepared in a unit dosage form. In such forms, the preparation is subdivided into suitably sized unit doses containing appropriate quantities of the active component, e.g., an effective amount to achieve the desired purpose.

PREPARATIVE EXAMPLES

Compounds of the invention can be made using procedures known in the art. The following reaction schemes show typical procedures, but those skilled in the art will recognize that other procedures can also be suitable.

Where NMR data are presented, spectra were obtained on either a Varian VXR-200 (200 MHz, $^1$H), Varian Gemini-300 (300 MHz) or XL-400 (400 MHz), or Bruker AVANCE 300 or 500 MHz spectrometers and are reported as ppm (δ) down field from Me$_4$Si with number of protons, multiplicities, and coupling constants in Hertz indicated parenthetically. Optical rotation data was obtained on a Perkin Elmer 341 polarimeter and substrate concentration c is reported in mg/mL.

Techniques, solvents and reagents may be referred to by their following abbreviations:
Thin layer chromatography: TLC
High performance liquid chromatography: HPLC
ethyl acetate: AcOEt or EtOAc
methanol: MeOH
ethanol: EtOH
ether or diethyl ether: Et$_2$O
tetrahydrofuran: THF
Acetonitrile: MeCN
1,2-dimethoxyethane: DME
Trifluoroacetic acid: TFA
Dimethylacetamide: DMA
Dimethylformamide: DMF
Dimethylsulfoxide: DMSO
triethylamine: Et$_3$N or TEA
tert-Butoxycarbonyl: t-Boc or Boc
2-(Trimethylsilyl)ethoxycarbonyl: Teoc
nuclear magnetic resonance spectroscopy: NMR
liquid chromatography mass spectrometry: LCMS
high resolution mass spectrometry: HRMS
liters: L
milliliters: mL
millimoles: mmol
microliters: μl (or μL)
grams: g
milligrams: mg
centimeters: cm
room temperature (ambient, about 25° C.): rt (or RT)
minutes: min
Retention time: t$_R$
hours: h (or hr)
N-bromosuccinimide: NBS
Methyl magnesium bromide: MeMgBr
iron(III) acetylacetonate: Fe(acac)$_3$
Diphenylphosphoryl azide: DPPA
1-(3-Dimethylaminopropyl)-3-ethylcarbodiimide hydrochloride: EDCl
Diisopropylethylamine: DIEA or iPr$_2$NEt
Diisopropylamine: iPr$_2$NH
2-(Trimethylsilyl)ethanol: TMSethanol
3-Chloroperoxybenzoic acid: mCPBA
n-Butyllithium: nBuLi
lithium diisopropylamide: LDA
[1,1'-Bis(diphenylphosphino)ferrocene]dichloropalladium (II): PdCl$_2$dppf
Palladium(II) acetate: Pd(OAc)$_2$
Methanesulfonyl chloride: MeSO$_2$Cl
Benzyl: Bn
saturated: Sat.
round bottom flask: RBF
acetonitrile: MeCN
butyl: Bu
4-methoxy benzyl: PMB
Sodium methoxide: NaOMe
Hexane: hex (or hex.)
Molar: M
aqueous: aq.
acetic acid: AcOH (or HOAc)
methylene chloride: DCM
reverse phase: RP
dichloro ethane: DCE
phenyl: Ph
preparative: prep (or prep.)

The following general procedures were employed in the preparation of examples 1-9 unless noted otherwise: $^1$H and $^{13}$C NMR spectra were taken in CDCl$_3$ or CD$_3$OD at 400 MHz and 75 MHz respectively. Chemical shifts are reported in parts per million using the solvent internal standard. Anhydrous solvents (CH$_2$Cl$_2$, toluene, methanol, THF) were purchased directly from Aldrich and used without further purification. All other reagents were used as supplied. All reactions were carried out in flame-dried glassware under argon or nitrogen atmosphere unless otherwise specified. Analytical thin layer chromatography was performed on 0.25 mm silica gel 60 Å plates. Flash chromatography was performed over normal-phase silica gel RediSep ISCO columns using UV detection (220 or 254 nm). Conditions for LCMS and RP-HPLC analyses are as follows:

Conditions A
Column: Gemini C-18, 50×4.6 mm, 5 micron, obtained from Phenomenex; mobile phase: A: 0.05% TFA in water, B: 0.05% TFA in acetonitrile; gradient: 90:10 to 5:95 (A:B) over 5 min; flow rate: 1.0 mL/min; UV detection: 254 nm; ESI-MS: Electra Spray Ionization Liquid chromatography-mass spectrometry (ESI LC/MS) was performed on a PE SCIEX API-150EX, single quadrupole mass spectrometer.

Conditions B
Column: Waters SunFire C-18 4.6 mm×50 mm; mobile phase: A: 0.05% TFA in water, B: 0.05% TFA in acetonitrile; gradient: 90:10 (A:B) for 1 min, 90:10 to 0:100 (A:B) over 4 min, 0:100 (A:B) for 2 min; flow rate: 1.0 mL/min; detection: 254 nm, mass spectrometer: Finnigan LCQ Duo electrospray.

Conditions C
Column: Agilent Zorbax SB-C18 (3.0×50 mm) 1.8 um; mobile phase: A: 0.1% TFA in water, B: 0.1% TFA in acetonitrile; gradient: 90:10 (A:B) for 0.3 min, 90:10 to 5:95 (A:B) over 5.1 min, 5:95 (A:B) for 1.2 min; flow rate: 1.0 mL/min; UV detection: 254 and 220 nm, mass spectrometer: Agilent 6140 quadrupole.

Conditions D
Column: Agilent Zorbax SB-C18 (3.0×50 mm) 1.8 um; mobile phase: A: 0.1% TFA in water, B: 0.1% TFA in acetonitrile; gradient: 90:10 (A:B) for 0.3 min, 90:10 to 5:95 (A:B) over 1.2 min, 5:95 (A:B) for 1.2 min. Flow rate: 1.0 mL/min; UV detection: 254 and 220 nm, mass spectrometer: Agilent 6140 quadrupole.

Conditions E
Column: Novapak HR-C18 (25×100 mm) 6 um in Waters PrepLC 25 mm module; mobile phase: A: 0.1% TFA in water, B: 0.1% TFA in acetonitrile; gradient: 90:10 (A:B) for 1 min, 90:10 to 5:95 (A:B) over 10 min, 5:95 (A:B) for 5 min. Flow rate: 30 mL/min; UV detection: 254 or 220 nm.

Example 1

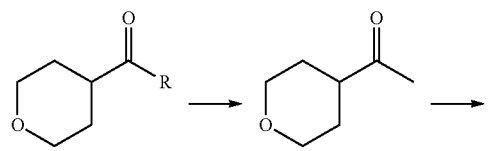

1 R = OH
2 R = N(Me)OMe

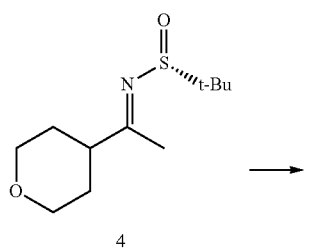

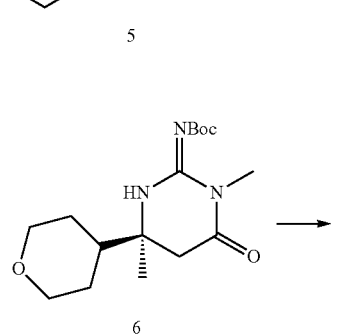

-continued

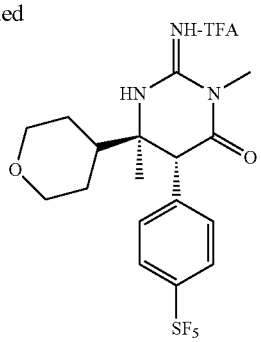

(5R,6R)-2-imino-3,6-dimethyl-6-(tetrahydro-2H-pyran-4-yl)-5-(4-(pentafluorothio)phenyl)tetrahydro-pyrimidin-4(1H)-one (8)

Step 1

To a solution of tetrahydro-2H-pyran-4-carboxylic acid 1 (4.0 g, 31 mmol) in DCM (65 mL) was added sequentially N,O-dimethylhydroxylamine hydrochloride (3.3 g, 34 mmol), 4-methylmorpholine (7.4 mL, 68 mmol), and N-(3-dimethylaminopropyl)-N'-ethylcarbodiimide hydrochloride (6.5 g, 34 mmol). The resulting mixture was stirred at RT for 18 h. At that time, the reaction was diluted with 1N HCl and EtOAc and stirred vigorously until both phases cleared. The phases were separated, and the aqueous layer was extracted with EtOAc. The organic portions were combined, washed with brine, dried over MgSO$_4$, filtered, and concentrated. The crude residue was subjected to column chromatography (120 g silica, 80 ml/min, 0% to 100% EtOAc/hexanes) to give N-methoxy-N-methyltetrahydro-2H-pyran-4-carboxamide 2 (4.3 g, 24.8 mmol, 81%). LCMS for 2 (conditions D): t$_R$=1.12 min, m/e=174.3 (M+H, base).

Step 2

A flask was charged with N-methoxy-N-methyltetrahydro-2H-pyran-4-carboxamide 2 (11.7 g, 67.5 mmol) and THF (350 mL). The resulting mixture was immersed in a cooling bath at −60° C., and methylmagnesium bromide (3.0 M in ether, 33.8 mL, 101.4 mmol) was added via syringe over ~8 min. The temperature of the bath was allowed to rise to 0° C. over 6 h. At that time, the reaction was diluted with water and EtOAc and stirred vigorously for 10 min. The phases were separated, and the aqueous layer was extracted with EtOAc. The organic portions were combined, washed with brine, dried over MgSO$_4$, filtered, and concentrated. The crude residue was subjected to column chromatography (120 g silica, 80 mL/min, 0% to 100% EtOAc/hexanes) to give 4-acetyltetrahydro-4H-pyran 3 (7.05 g, 55.0 mmol, 81%). $^1$H NMR (400 MHz, CDCl$_3$) for 3: δ 3.95 (ddd, J=11.6, 4.4, 2.8 Hz, 2 H), 3.38 (dt, J$_d$=2.8 Hz, J$_t$=11.6 Hz, 2 H), 2.50 (m, 1 H), 2.12 (s, 3 H), 1.75 (m, 2 H), 1.65 (m, 2 H). LCMS for 3 (conditions D): t$_R$=0.83 min, m/e=129.4 (M+H, base).

Step 3

A 200 mL sealed tube was charged with 4-acetyltetrahydro-4H-pyran 3 (7.0 g, 55 mmol), THF (100 mL), and a solution of titanium(IV) ethoxide (28.6 mL, 136 mmol) in THF (30 mL). The resulting mixture was degassed by evacuation and back-fill with N$_2$ (3×), sealed, and immersed in a 85° C. oil bath. After 30 h, the reaction was poured into an erlenmeyer containing 300 mL of water, and the mixture was further diluted with EtOAc (200 mL) and stirred vigorously for 15 minutes. The mixture was then filtered through paper with copious EtOAc washes. The phases of the filtrate were separated and the aqueous portion was extracted 2× with EtOAc. The organic portions were combined, washed with brine, dried over $MgSO_4$, filtered, and concentrated. This crude sample was subjected to column chromatography (ISCO, 330 g silica, 100 mL/min, 0% to 100% EtOAc/hexanes) to give (R)-2-methyl-N-(1-(tetrahydro-2H-pyran-4-yl)ethylidene)propane-2-sulfinamide 4 (9.2 g, 73%). LCMS (conditions D): $t_R$=1.85 min, m/e=232.2 (M+H, base).

Step 4

To a 0° C. solution of N,N-diisopropylamine (12.7 mL, 90.8 mmol) in THF (120 mL) was added n-butyllithium (2.5 M in hexanes, 35.1 mL) over ~5 min. The resulting solution was stirred at 0° C. for 10 min, then the cooling bath was removed and the mixture stirred for an additional 10 min before it was finally cooled to −78° C. To this solution of LDA was then added via cannula a −78° C. solution of methyl acetate (6.01 mL, 75.6 mmol) in THF (30 mL) over ~5 min. This mixture was stirred at −78° C. for 30 min, and then a mixture of chlorotriisopropoxytitanium (27.1 mL, 113 mmol) and THF (30 mL) was added via syringe. After 30 min, a RT solution of (R)-2-methyl-N-(1-(tetrahydro-2H-pyran-4-yl)ethylidene)propane-2-sulfinamide 4 (7.0 g, 30 mmol) in THF (40 mL) was added via cannula over ~5 min. The reaction was then stirred at −78° C. for 5 h. At that time, while still at −78° C., the reaction was diluted rapidly with water (300 mL) and agitated. The reaction was allowed to gradually warm to RT overnight with stirring. At that time, the mixture was further diluted with EtOAc and water, and the mixture was filtered with copious EtOAc washes. The phases of the filtrate were separated and the aqueous layer was extracted 2× with EtOAc. The organic portions were combined, washed with brine, dried over $MgSO_4$, filtered and concentrated. The crude sample was subjected to column chromatography (ISCO, 330 g silica, 100 mL/min, 0% to 25% i-PrOH/hexanes) to give (S)-methyl 3-((R)-1,1-dimethylethylsulfinamido)-3-(tetrahydro-2H-pyran-4-yl)butanoate 5 (6.5 g, 70%). LCMS (conditions D) for 5: $t_R$=1.90 min, m/e=306.2 (M+H, base), 328.2 (M+Na).

Step 5

To a mixture of (S)-methyl 3-((R)-1,1-dimethylethylsulfinamido)-3-(tetrahydro-2H-pyran-4-yl)butanoate 5 (6.5 g, 21 mmol), DCM (70 mL), and MeOH (35 mL) was added hydrogen chloride solution (4.0 M in 1,4-dioxane, 79.8 mL). The resulting mixture was stirred at RT for 2 h. At that time, the reaction was concentrated and then diluted with toluene (100 mL) and re-concentrated. This material was dissolved in DMF (100 mL) and N-tert-butylcarbamoyl-N'-methylthiourea (5.06 g, 26.6 mmol), N,N-diisopropylethylamine (16.7 mL, 95.8 mmol), and N-(3-dimethylaminopropyl)-N'-ethylcarbodiimide hydrochloride (6.12 g, 31.9 mmol) were added. The mixture was immersed in a 45° C. oil bath and allowed to stir overnight. After 16 h, the reaction was diluted with water (200 mL), 3N HCl (50 mL) and EtOAc and stirred vigorously for 10 min. The phases were separated and the aqueous layer was extracted 2× with EtOAc. The organic portions were combined, washed with sat. aq. $NaHCO_3$ and brine, dried over $MgSO_4$, filtered and concentrated. This crude sample was subjected to column chromatography (ISCO, 330 g silica, 100 ml/min, 0% to 100% EtOAc/hexanes) to give (S)-tert-butyl 1,4-dimethyl-6-oxo-4-(tetrahydro-2H-pyran-4-yl)tetrahydropyrimidin-2(1H)-ylidenecarbamate 6 (5.9 g, 85%). $^1$H NMR (400 MHz, $CDCl_3$) for 6: δ=9.98 (s, 1 H), 4.03 (m, 2 H), 3.34 (m, 2 H), 3.27 (s, 3 H), 2.62 (ABq, $J_{AB}$=16.4 Hz, $\Delta v_{AB}$=66.8 Hz, 2 H), 1.66 (m, 1 H), 1.57 (m, 2 H), 1.49 (s, 9 H), 1.43 (m, 3 H), 1.25 (s, 3 H). LCMS for 6 (conditions D): $t_R$=1.86 min, m/e=326.3 (M+H), 270.2 (M−t−Bu+H, base).

Step 6

A flame-dried 20 mL microwave tube was charged with (S)-tert-butyl-1,4-dim ethyl-6-oxo-4-(tetrahydro-2H-pyran-4-yl tetrahydro-pyrimidin-2(1H)-ylidenecarbamate 6 (0.500 g, 1.54 mmol) and THF (4 mL). The tube was then immersed in a cooling bath at −50° C. and lithium hexamethyldisilazide (1.0 M in THF, 3.84 mL) was added to the solution via syringe over ~5 min. After 45 minutes, the bath had warmed to −30° C., and a solution of zinc dichloride (1.3 M in THF, 3.08 mL) was added via syringe. After an additional 45 minutes, keeping the bath between −30° C. and −20° C. during that time, 1-bromo-4-(pentafluorothio)benzene (0.565 g, 2.00 mmol) was added via syringe as a solution in THF (1 mL), followed by palladium(II) acetate (8.6 mg, 0.038 mmol) and 1,2,3,4,5-pentaphenyl-1'-(di-t-butylphosphino)ferrocene (55 mg, 0.077 mmol) as solids. The tube was sealed and the mixture was degassed by evacuation and back-fill with $N_2$ (3×). The tube was then immersed in an oil bath at 50° C. and allowed to stir. After ~16, the reaction was cooled and loaded directly onto a 24 g silica column, dried under $N_2$ flow for 2 h, and then subjected to column chromatography running the small column in series onto a larger column (ISCO, 120 g silica, 90 mL/min, 0% to 40% EtOAc/hexanes) to give tert-butyl (4R,5R)-1,4-dimethyl-6-oxo-4-(tetrahydro-2H-pyran-4-yl)-5-(4-(pentafluorothio)phenyl)-tetrahydropyrimidin-2(1H)-ylidenecarbamate 7 (0.43 g, 53%). LCMS for 7 (conditions D): $t_R$=2.32 min, m/e=528.2 (M+H), 472.2 (M−t−Bu+H, base), 550.2 (M+Na).

Step 7

A flask was charged with tert-butyl (4R,5R)-1,4-dimethyl-6-oxo-4-(tetrahydro-2H-pyran-4-yl)-5-(4-(pentafluorothio)phenyl)-tetrahydropyrimidin-2(1H)-ylidenecarbamate 7 (0.43 g, 0.82 mmol), DCM (4.5 mL), and trifluoroacetic acid (1.5 mL, 19 mmol). After 3 h, the mixture was diluted with toluene and concentrated. The resulting crude residue was precipitated from a mixture of DCM (~2 mL), $Et_2O$ (~10 mL), and hexanes (~10 mL) to give (5R,6R)-2-imino-3,6-dimethyl-6-(tetrahydro-2H-pyran-4-yl)-5-(4-(pentafluorothio)phenyl)-tetrahydropyrimidin-4(1H)-one 2,2,2-trifluoroacetate (0.37 g, 90%) as its trifluoroacetic acid salt 8. $^1$H NMR (400 MHz, $CD_3OD$) for 8: δ 7.87 (m, 2 H), 7.46 (br d, J=15.6 Hz, 2 H), 4.39 (s, 1 H), 4.01 (m, 2H), 3.40 (s, 3 H), 3.36 (m, 2 H), 1.81 (m, 1 H), 1.71 (m, 1 H), 1.52 (m, 2 H), 1.09 (s, 3H). LCMS for 8 (conditions A): $t_R$=3.07 min, m/e=428.2 (M+H).

Examples 2-8 were prepared using methods similar to that described in Example 1.

Example 2

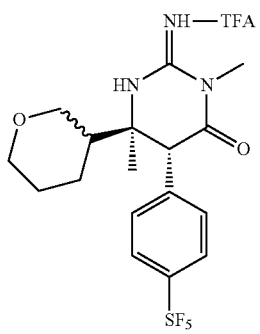

(5R,6R)-2-imino-3,6-dimethyl-6-(tetrahydro-2H-pyran-3-0)-5-(4-(pentafluorothio)phenyl)tetrahydro-pyrimidin-4(1H)-one (9)

$^1$H NMR (400 MHz, CD$_3$OD) for 9: δ 7.87 (m, 4 H), 7.46 (br d, J=8.4 Hz, 4 H), 4.40 (s, 1 H), 4.39 (s, 1 H), 4.04 (m, 2 H), 3.87 (m, 2 H), 3.40 (s, 6 H), 3.36 (m, 4 h), 1.98 (m, 2 H), 1.78 (m, 4 H), 1.65-1.50 (m, 4 H), 1.10 (s, 3 H), 1.08 (s, 3 H). LCMS for 9 (conditions A): t$_R$=3.15 min, m/e=428.2 (M+H).

Example 3

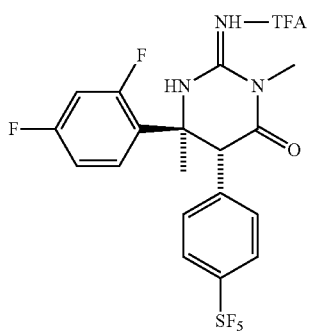

Pentafluoro[4-[(hexahydro-2-imino-1,4(S)-dimethyl-6-oxo-4-(2,4-difluorophenyl)-5(R)-pyrimidinyl]phenyl]sulfur (10)

$^1$H NMR (400 MHz, CD$_3$OD) for 10: δ=7.82 (d, J=9.2 Hz, 2 H), 7.35 (d, J=8.4 Hz, 2 H), 7.32 (m, 1 H), 7.12 (m, 1 H), 7.00 (m, 1 H), 4.87 (s, 1 H), 3.37 (s, 3 H), 1.57 (s, 3 H); LCMS for 10 (conditions A) t$_R$=3.35 min; 456.3 (M+H-TFA)$^+$

Example 4

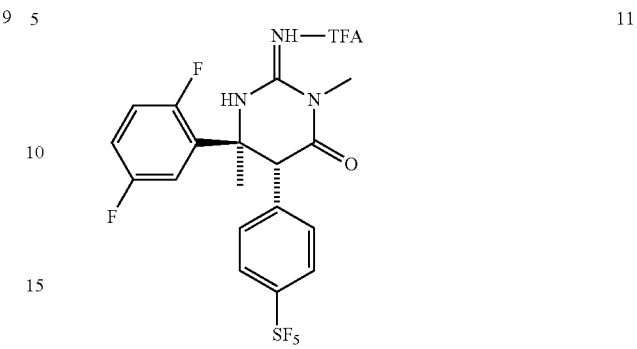

Pentafluoro[4-[hexahydro-2-imino-1,4(S)-dimethyl-6-oxo-4-(2,5-difluorophenyl)-5(R)-pyrimidinyl]phenyl]sulfur (11)

$^1$H NMR (400 MHz, CD$_3$OD) for 11: δ=7.82 (d, J=8.4 Hz, 2 H), 7.38 (d, J=8.8 Hz, 2 H), 7.27 (m, 1 H), 7.19 (m, 1 H), 7.08 (m, 1 H), 4.87 (s, 1 H), 3.37 (s, 3 H), 1.54 (s, 3 H); LCMS for 11 (conditions A) t$_R$=3.35 min; 456.3 (M+H−TFA)$^+$

Example 5

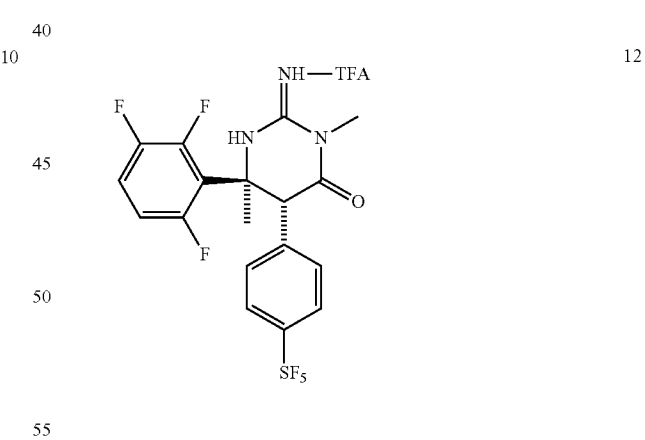

Pentafluoro[4-[hexahydro-2-imino-1,4(S)-dimethyl-6-oxo-4-(2,3,6-trifluorophenyl)-5(R)-pyrimidinyl]phenyl]sulfur (12)

$^1$H NMR (400 MHz, DMSO-d6) for 12: δ=7.94 (m, 2 H), 7.62 (m, 1 H), 7.43 (m, 2 H), 7.19 (m, 1 H), 4.83 (s, 1 H), 3.30 (s, 3 H), 1.56 (s, 3 H); LCMS for 12 (conditions A) t$_R$=3.37 min; 474.3 (M+H−TFA)$^+$

Example 6

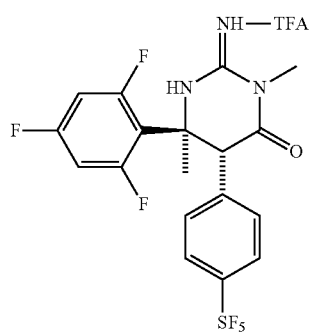

Pentafluoro[4-[hexahydro-2-imino-1,4(S)-dimethyl-6-oxo-4-(2,4,6-trifluorophenyl)-5(R)-pyrimidinyl]phenyl]sulfur (13)

$^1$H NMR (400 MHz, CD$_3$OD) for 13: δ=7.85 (d, J=8.8 Hz, 2 H), 7.39 (d, J=8.4 Hz, 2 H), 6.97 (m, 2 H), 4.81 (s, 1 H), 3.39 (s, 3 H), 1.61 (s, 3 H); LCMS for 13 (conditions A) $t_R$=3.33 min; 474.3 (M+H−TFA)$^+$

Example 7

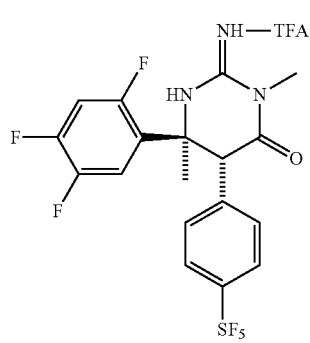

Pentafluoro[4-[hexahydro-2-imino-1,4(S)-dimethyl-6-oxo-4-(2,4,5-trifluorophenyl)-5(R)-pyrimidinyl]phenyl]sulfur (14)

$^1$H NMR (400 MHz, CD$_3$OD) for 14: δ=7.83 (d, J=6.4 Hz, 2 H), 7.20-7.40 (m, 4 H), 4.88 (s, 1 H), 3.38 (s, 3 H), 1.58 (s, 3 H); LCMS for 14 (conditions A) $t_R$=3.33 min; 474.3 (M+H−TFA)$^+$

Example 8

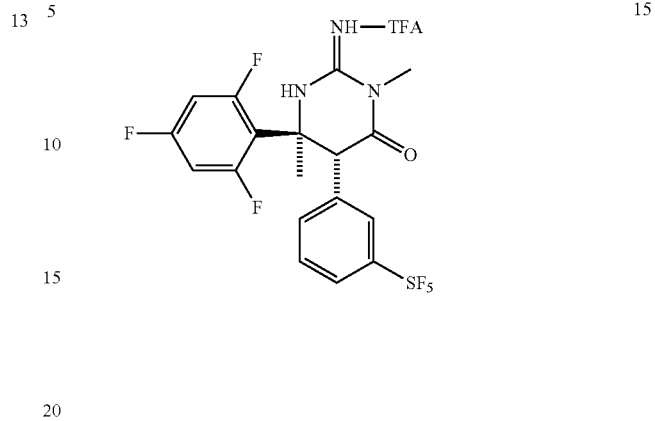

Pentafluoro[3-[hexahydro-2-imino-1,4(S)-dimethyl-6-oxo-4-(2,4,6-trifluorophenyl)-5(R)-pyrimidinyl]phenyl]sulfur (15)

$^1$H NMR (500 MHz, CD$_3$OD) for 15 δ=7.93 (m, 1 H), 7.62 (m, 1 H), 7.50 (m, 2 H), 7.28 (m, 2 H), 4.91 (s, 1 H), 3.31 (s, 3 H), 1.61 (s, 3 H); LCMS for 15 (conditions B) $t_R$=2.44 min; 474.0 (M+H−TFA)$^+$

Example 9

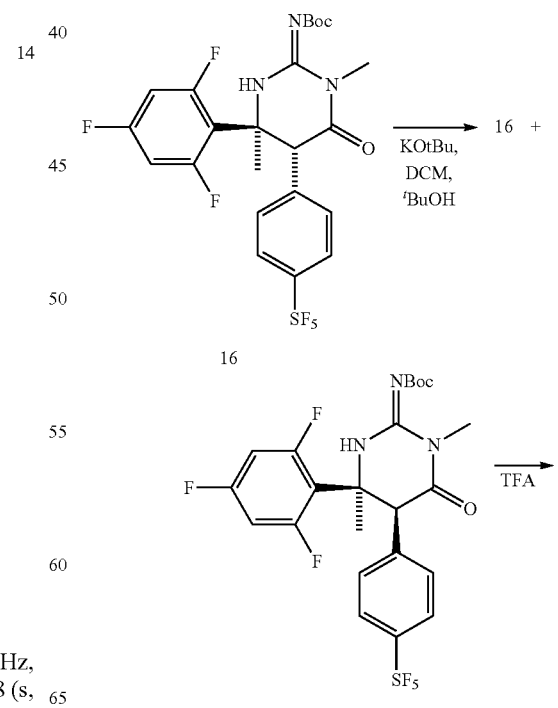

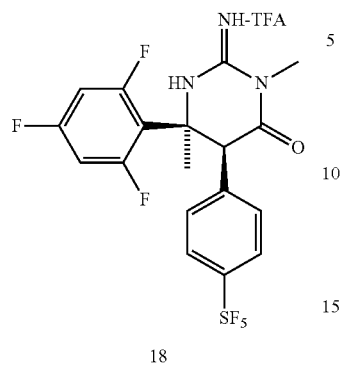

18

Pentafluoro[4-[hexahydro-2-imino-1,4(S)-dimethyl-6-oxo-4-(2,4,6-trifluorophenyl)-5(S)-pyrimidinyl]phenyl]sulfur (18)

To a solution of intermediate 16 (2.00 g, 3.49 mmol, 1 equiv, obtained as described in Example 6 before final deprotection) in $CH_2Cl_2$ (6 mL) and tert-butanol (24 mL) at RT was added potassium tert-butoxide (2.35 g, 21 mmol, 6 equiv). After 30 minutes, the orange solution was diluted with water and EtOAc. The organic layer was washed with brine (1×), dried over $MgSO_4$, and concentrated under reduced pressure to give a reddish foam (1.84 g), which was subjected to reverse-phase HPLC (conditions E). Repeated purifications via reverse-phase HPLC ultimately yielded pure epimer 17 (LCMS for 17 (conditions D) $t_R$=2.48 min) and recovered starting epimer 16 (LCMS for 16 (conditions D) $t_R$=2.54 min). Intermediate 17 (45 mg, 0.078 mmol) was dissolved in $CH_2Cl_2$ (2 mL) and TFA (2.mL) was added at room temperature. The reaction was stirred until LCMS-analysis of an aliquot in MeOH showed complete conversion. Toluene (10 mL) was added, and the volatiles were removed under reduced pressure. The residue was further dried under high vacuum, then dissolved in MeOH (~1 mL/100 mg residue), filtered through a 0.45 um PTFE filter, and subjected to reverse-phase HPLC (conditions B). Appropriate fractions were combined and concentrated under reduced pressure to give the desired product 18 as a white solid (36.9 mg TFA salt, 0.065 mmol, 83% yield). $^1$H NMR (400 MHz, $CD_3OD$) for 18 δ=7.71 (m, 2 H), 7.20 (m, 2 H), 6.85 (m, 2 H), 4.74 (s, 1 H), 3.43 (s, 3 H), 2.05 (s, 3 H); LCMS for 18 (conditions A) $t_R$=3.28 min; 474.3 (M+H−TFA)$^+$ Table 1 sets forth non-limiting examples of compounds of the invention. Esters, prodrugs, solvates, and tautomers of these compounds, and salts (including pharmaceutically acceptable salts) of said compounds, esters, prodrugs, solvates, and tautomers thereof, are also included within the scope of the invention. The compounds set forth in Table 1 were made according to methods described herein or analogous thereto.

TABLE 1

| Ex. # | Structure |
|---|---|
| 1 | 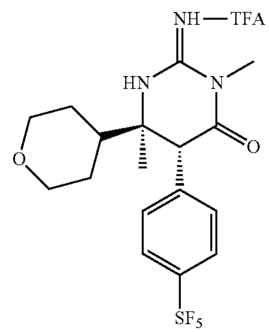 |
| 2 | 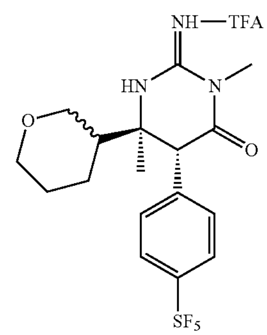 |
| 3 | 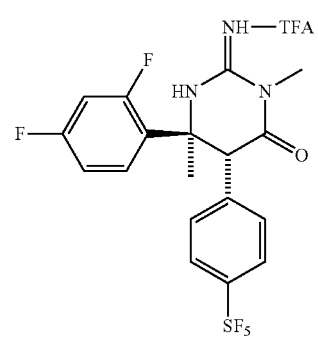 |
| 4 | 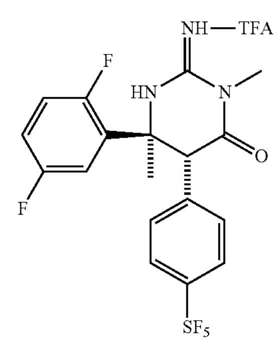 |

TABLE 1-continued

| Ex. # | Structure |
|---|---|
| 5 | 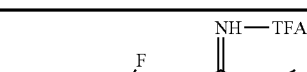 |
| 6 | 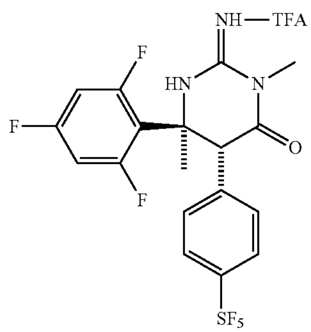 |
| 7 | 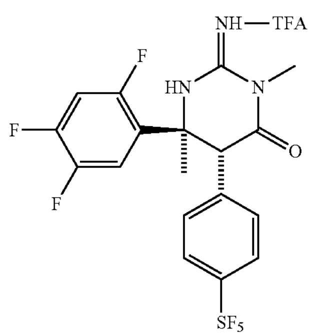 |
| 8 | 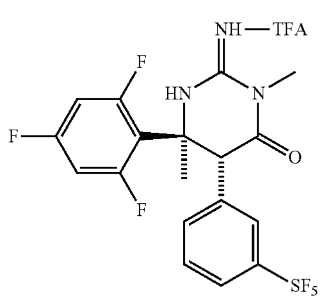 |

TABLE 1-continued

| Ex. # | Structure |
|---|---|
| 9 | 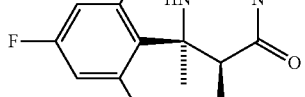 |

Assays

The protocol that was used to determine the recited values is described as follows.

BACE1 HTRF FRET Assay

Reagents

Na$^+$-Acetate pH 5.0

1% Brij-35

Glycerol

Dimethyl Sulfoxide (DMSO)

Recombinant human soluble BACE1 catalytic domain (>95% pure)

APP Swedish mutant peptide substrate (QSY7-APP$^{swe}$-Eu): QSY7-EISEVNLDAEFC-Europium-amide A homogeneous time-resolved FRET assay was used to determine IC$_{50}$ values for inhibitors of the soluble human BACE1 catalytic domain. This assay monitored the increase of 620 nm fluorescence that resulted from BACE1 cleavage of an APPswedish APP$^{swe}$ mutant peptide FRET substrate (QSY7-EISEVNLDAEFC-Europium-amide). This substrate contained an N-terminal QSY7 moiety that served as a quencher of the C-terminal Europium fluorophore (620 nm Em). In the absence of enzyme activity, 620 nm fluorescence was low in the assay and increased linearly over 3 hours in the presence of uninhibited BACE1 enzyme. Inhibition of BACE1 cleavage of the QSY7-APP$^{swe}$-Eu substrate by inhibitors was manifested as a suppression of 620 nm fluorescence.

Varying concentrations of inhibitors at 3× the final desired concentration in a volume of 10 ul were preincubated with purified human BACE1 catalytic domain (3 nM in 10 μl) for 30 minutes at 30° C. in reaction buffer containing 20 mM Na-Acetate pH 5.0, 10% glycerol, 0.1% Brij-35 and 7.5% DSMO. Reactions were initiated by addition of 10 μl of 600 nM QSY7-APP$^{swe}$-Eu substrate (200 nM final) to give a final reaction volume of 30 μl in a 384 well Nunc HTRF plate. The reactions were incubated at 30° C. for 1.5 hours. The 620 nm fluorescence was then read on a Rubystar HTRF plate reader (BMG Labtechnologies) using a 50 μs delay followed by a 400 millisecond acquisition time window. Inhibitor IC$_{50}$ values were derived from non-linear regression analysis of concentration response curves. K$_i$ values were then calculated from IC$_{50}$ values using the Cheng-Prusoff equation using a previously determined μm value of 8 μM for the QSY7-APP$^{swe}$-Eu substrate at BACE1.

All of the compounds of the invention set forth in Table 1 exhibited K$_i$ values of less than about 200 nM and greater than about 2 nM in this assay.

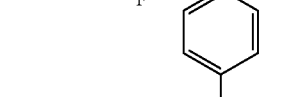

BACE Inhibitor Whole Cell $IC_{50}$ Determination Using HEK293-APP$^{swe/lon}$ Cells HEK293 cells were obtained from the American Type Culture Collection (ATCC) and stably transfected with the human amyloid precursor protein cDNA containing the FAD Swedish (enhances β-secretase processing) and London (enhances Aβ42 cleavage) mutations. A HEK293 stable clone with Aβ expression (HEK293-APP$^{swe/lon}$) was identified and maintained at 37° C., 5% $CO_2$ in the ATCC-recommended growth media supplemented with hygromycin. Determination of compound $IC_{50}$ values for inhibition of APP processing (reduction of Aβ1-40, Aβ1-42 and sAPPβ levels) in HEK293-APP$^{swe/lon}$ cells was accomplished by treatment of cells with various concentrations of compounds diluted in fresh complete growth media for 4 hours at 37° C., 5% $CO_2$. Aβ40 or Aβ42 were measured in 15 μl of media using a mesoscale based ELISA assay. Full length Aβ40 and Aβ42 peptides were captured with the N-terminal specific biotinylated-WO2 monoclonal antibody and detected using either the ruthenylated Aβ40 C-terminal specific monoclonal antibody, G2-10 or the ruthenylated Aβ42 C-terminal specific monoclonal antibody G2-11 respectively. Raw electrochemiluminescence values were measured using a Mesoscale Sector Imager plate reader and were plotted as a function of compound concentration. $IC_{50}$ values were interpolated from the data using nonlinear regression analysis (Sigmoidal dose response fit with variable slope) of the data using GraphPad Prism software.

While the present invention has been described in view of the specific embodiments set forth above, many alternatives, modifications and other variations thereof will be apparent to those of ordinary skill in the art. All such alternatives, modifications and variations are intended to fall within the spirit and scope of the present invention.

We claim:

1. A compound, or pharmaceutically acceptable salt thereof, said compound having the structural Formula (a):

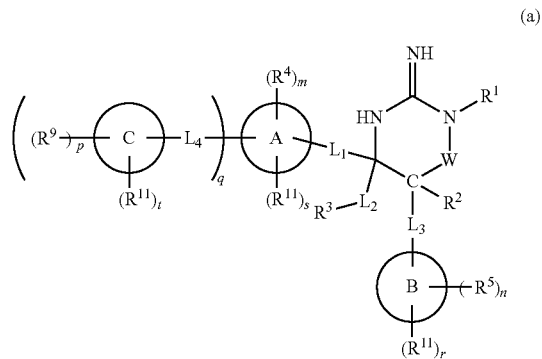

(a)

wherein:

W is selected from the group consisting of —C(O)—, —C(S)—, and —C(=NR$^{8A}$)—;

-$L_1$- is present or absent and when present represents a divalent moiety selected from the group consisting of -alkyl-, -haloalkyl-, -heteroalkyl-, -alkenyl-, and -alkynyl-;

-$L_2$- is present or absent and when present represents a divalent moiety selected from the group consisting of -alkyl-, -haloalkyl-, -heteroalkyl-, -alkenyl-, and -alkynyl-;

-$L_3$- is present or absent and when present represents a divalent moiety selected from the group consisting of -alkyl-, -haloalkyl-, -heteroalkyl-, -alkenyl-, and -alkynyl-;

each -$L_4$- (when present) independently is present or absent and when present represents a divalent moiety independently selected from the group consisting of -alkyl-, -haloalkyl-, -heteroalkyl-, -alkenyl-, -alkynyl-, —N(R$^8$)—, —NHC(O)—, and —C(O)NH—;

m, n, p, q, r, s, and t are each independently selected integers, wherein:

m is 0 or more, n is 0 or more, p is 0 or more, q is 0 or more, r is 0, 1, or 2, s is 0, 1, or 2, t is 0, 1, or 2, with the provisos that:

(i) the maximum value of the sum of m, q, and s is the maximum number of available substitutable hydrogen atoms on ring A, (ii) the maximum value of the sum of n and r is the maximum number of available substitutable hydrogen atoms on ring B, and (iii) the maximum value of the sum of p and t is the maximum number of available substitutable hydrogen atoms on ring C, and (iv) the sum of r, s, and t is 1 or 2;

R$^1$ is selected from the group consisting of: H, alkyl, haloalkyl, heteroalkyl, heterohaloalkyl, cycloalkyl, cycloalkylalkyl-, heterocycloalkyl, heterocycloalkylalkyl-, aryl, arylalkyl-, heteroaryl, and heteroarylalkyl-, wherein each of said alkyl, haloalkyl, heteroalkyl, heterohaloalkyl, cycloalkyl, cycloalkylalkyl-, heterocycloalkyl, heterocycloalkylalkyl-, aryl, arylalkyl-, heteroaryl, and heteroarylalkyl- of R$^1$ is unsubstituted or substituted with from 1 to 5 independently selected R$^{10}$ groups;

R$^2$ is selected from the group consisting of H, alkyl, halo, haloalkyl, aryl, arylalkyl-, heteroaryl, heteroarylalkyl-, cycloalkyl, cycloalkylalkyl-, cycloalkenyl, heterocycloalkyl, and heterocycloalkenyl, wherein each of said alkyl, haloalkyl, aryl, arylalkyl-, heteroaryl, heteroarylalkyl-, cycloalkyl, cycloalkylalkyl-, cycloalkenyl, heterocycloalkyl, and heterocycloalkenyl of R$^2$ is unsubstituted or substituted with from 1 to 5 independently selected R$^{10}$ groups;

R$^3$ is selected from the group consisting of alkyl, aryl, heteroaryl, cycloalkyl, cycloalkenyl, heterocycloalkyl, and heterocycloalkenyl, wherein each of said alkyl, aryl, heteroaryl, cycloalkyl, cycloalkenyl, heterocycloalkyl, and heterocycloalkenyl of R$^3$ is unsubstituted or substituted with from 1 to 5 independently selected R$^{10}$ groups;

ring A is selected from the group consisting of monocyclic aryl, monocyclic heteroaryl, monocyclic cycloalkyl, monocyclic cycloalkenyl, monocyclic heterocycloalkyl, monocyclic heterocycloalkenyl, and a multicyclic group;

each R$^4$ (when present) is independently selected from the group consisting of halo, —CN, —NO$_2$, —Si(R$^6$)$_3$, —P(O)(OR$^7$)$_2$, —P(O)(OR$^7$)(R$^7$), —N(R$^8$)$_2$, —NR$^8$C(O)R$^7$, —NR$^8$S(O)$_2$R$^7$, —NR$^8$C(O)N(R$^8$)$_2$, —NR$^8$C(O)OR$^7$, —C(O)R$^7$, —C(O)$_2$R$^7$, —C(O)N(R$^8$)$_2$, —S(O)R$^7$, —S(O)$_2$R$^7$, —S(O)$_2$N(R$^8$)$_2$, —OR$^7$, —SR', alkyl, haloalkyl, haloalkoxy, heteroalkyl, alkenyl, alkynyl, cycloalkyl, cycloalkylalkyl-, heterocycloalkyl, aryl, and heteroaryl, wherein each said alkyl, haloalkyl, haloalkoxy, heteroalkyl, alkenyl, alkynyl, cycloalkyl, cycloalkylalkyl-, heterocycloalkyl, aryl, and heteroaryl of $R^4$ (when present) is optionally independently unsubstituted or further substituted with one or more independently selected groups selected from the group consisting of lower alkyl, lower alkenyl, lower alkynyl, lower heteroalkyl, halo, —CN, —SF$_5$, —OSF$_5$, —NO$_2$, —N(R$^8$)$_2$, —OR$^7$, —C(O)N(R$^8$)$_2$, and cycloalkyl;

ring B is selected from the group consisting of monocyclic aryl, monocyclic heteroaryl, monocyclic cycloalkyl, monocyclic cycloalkenyl, monocyclic heterocycloalkyl, monocyclic heterocycloalkenyl, and a multicyclic group;

each $R^5$ (when present) is independently selected from the group consisting of halo, —CN, —NO$_2$, —Si(R$^6$)$_3$, —P(O)(OR$^7$)$_2$, —P(O)(OR$^7$)(R$^7$), —N(R$^8$)$_2$, —NR$^8$C(O)R$^7$, —NR$^8$S(O)$_2$R$^7$, —NR$^8$C(O)N(R$^8$)$_2$, —NR$^8$C(O)OR$^7$, —C(O)R$^7$, —C(O)$_2$R$^7$, —C(O)N(R$^8$)$_2$, —S(O)R$^7$, —S(O)$_2$R$^7$, —S(O)$_2$N(R$^8$)$_2$, —OR$^7$, —SR$^7$, alkyl, haloalkyl, haloalkoxy, heteroalkyl, alkenyl, alkynyl, cycloalkyl, cycloalkylalkyl-, heterocycloalkyl, aryl, and heteroaryl, wherein each said alkyl, haloalkyl, haloalkoxy, heteroalkyl, alkenyl, alkynyl, cycloalkyl, cycloalkylalkyl-, heterocycloalkyl, aryl, and heteroaryl of $R^5$ (when present) is optionally independently unsubstituted or further substituted with one or more independently selected groups selected from the group consisting of lower alkyl, lower alkenyl, lower alkynyl, lower heteroalkyl, halo, —CN, —SF$_5$, —OSF$_5$, —NO$_2$, —N(R$^8$)$_2$, —OR$^7$, —C(O)N(R$^8$)$_2$, and cycloalkyl;

each ring C (when present) is independently selected from the group consisting of monocyclic aryl, monocyclic heteroaryl, monocyclic cycloalkyl, monocyclic cycloalkenyl, monocyclic heterocycloalkyl, monocyclic heterocycloalkenyl, and a multicyclic group;

each $R^6$ (when present) is independently selected from the group consisting of alkyl, aryl, arylalkyl-, haloalkyl, cycloalkyl, cycloalkylalkyl-, heteroaryl, and heteroarylalkyl-;

each $R^7$ (when present) is independently selected from the group consisting of H, alkyl, alkenyl, heteroalkyl, haloalkyl, aryl, arylalkyl-, heteroaryl, heteroarylalkyl-, cycloalkyl, cycloalkylalkyl-, heterocycloalkyl, and heterocycloalkylalkyl-;

each $R^8$ (when present) is independently selected from the group consisting of H, alkyl, alkenyl, heteroalkyl, haloalkyl, aryl, arylalkyl-, heteroaryl, heteroarylalkyl-, cycloalkyl, cycloalkylalkyl-, heterocycloalkyl, and heterocycloalkylalkyl-;

$R^{8A}$ is selected from the group consisting of alkyl, alkenyl, cycloalkyl, cycloalkylalkyl, heterocycloalkyl, heterocycloalkylalkyl, aryl, arylalkyl, heteroaryl, heteroarylalkyl, arylcycloalkyl, OR$^7$, —CN, —C(O)R$^7$, —C(O)OR$^7$, —S(O)$_2$R$^7$, —C(O)N(R$^8$)$_2$, —S(O)N(R$^8$)$_2$, —S(O)$_2$N(R$^8$)$_2$, —NO$_2$, and —N(R$^8$)$_2$;

each $R^9$ (when present) is independently selected from the group consisting of: halogen, —CN, —NO$_2$, —Si(R$^6$)$_3$, —P(O)(OR$^7$)$_2$, —P(O)(OR$^7$)(R$^7$), —N(R$^8$)$_2$, —NR$^8$C(O)R$^7$, —NR$^8$S(O)$_2$R$^7$, —NR$^8$C(O)N(R$^8$)$_2$, —NR$^8$C(O)OR$^7$, —C(O)R$^7$, —C(O)$_2$R$^7$, —C(O)N(R$^8$)$_2$, —S(O)R$^7$, —S(O)$_2$R$^7$, —S(O)$_2$N(R$^8$)$_2$, —OR$^7$, —SR$^7$, alkyl, haloalkyl, heteroalkyl, alkenyl, alkynyl, aryl, arylalkyl-, cycloalkyl, heteroaryl, heteroarylalkyl-, and heterocycloalkyl;

each $R^{10}$ (when present) is independently selected from the group consisting of halo, —CN, —NO$_2$, —Si(R$^6$)$_3$, —P(O)(OR$^7$)$_2$, —P(O)(OR$^7$)(R$^7$), —N(R$^8$)$_2$, —NR$^8$C(O)R$^7$, —NR$^8$S(O)$_2$R$^7$, —NR$^8$C(O)N(R$^8$)$_2$, —NR$^8$C(O)OR$^7$, —C(O)R$^7$, —C(O)$_2$R$^7$, —C(O)N(R$^8$)$_2$, —S(O)R$^7$, —S(O)$_2$R$^7$, —S(O)$_2$N(R$^8$)$_2$, —OR$^7$, —SR$^7$, alkyl, haloalkyl, haloalkoxy, heteroalkyl, alkenyl, alkynyl, cycloalkyl, heterocycloalkyl, aryl, and heteroaryl, wherein each said alkyl, haloalkyl, haloalkoxy, heteroalkyl, alkenyl, alkynyl, cycloalkyl, heterocycloalkyl, aryl, and heteroaryl of $R^{10}$ (when present) is optionally independently unsubstituted or further substituted with one or more independently selected groups selected from the group consisting of lower alkyl, lower alkenyl, lower alkynyl, lower heteroalkyl, halo, —CN, —NO$_2$, —N(R$^8$)$_2$, —OR$^7$, —C(O)N(R$^8$)$_2$, and cycloalkyl; and each $R^{11}$ is independently selected from the group consisting of —SF$_5$ and —OSF$_5$.

2. A compound, or pharmaceutically acceptable salt thereof, said compound having the structural Formula (I):

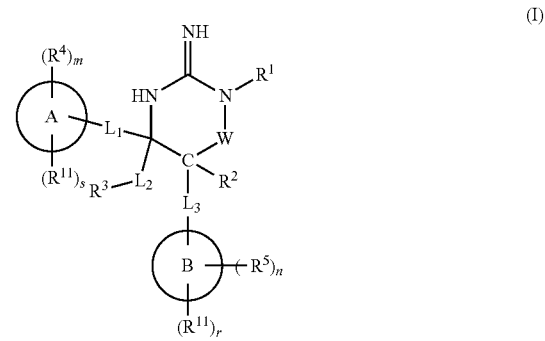

(I)

wherein:

W is selected from the group consisting of —C(O)—, —C(S)—, and —C(=NR$^{8A}$)—;

-L$_1$- is present or absent and when present represents a divalent moiety selected from the group consisting of -alkyl-, -haloalkyl-, -heteroalkyl-, -alkenyl-, and -alkynyl-;

-L$_2$- is present or absent and when present represents a divalent moiety selected from the group consisting of -alkyl-, -haloalkyl-, -heteroalkyl-, -alkenyl-, and -alkynyl-;

-L$_3$- is present or absent and when present represents a divalent moiety selected from the group consisting of -alkyl-, -haloalkyl-, -heteroalkyl-, -alkenyl-, and -alkynyl-;

m, n, r, and s are each independently selected integers, wherein:

m is 0 or more, n is 0 or more, r is 0, 1, or 2, s is 0, 1, or 2, with the provisos that:

(i) the maximum value of the sum of m and s is the maximum number of available substitutable hydrogen atoms on ring A, (ii) the maximum value of the sum of n and r is the maximum number of available substitutable hydrogen atoms on ring B, and (iii) the sum of r and s is 1 or 2;

$R^1$ is selected from the group consisting of: H, alkyl, haloalkyl, heteroalkyl, heterohaloalkyl, cycloalkyl, cycloalkylalkyl-, heterocycloalkyl, heterocycloalkylalkyl-, aryl, arylalkyl-, heteroaryl, and heteroarylalkyl-, wherein each of said alkyl, haloalkyl, heteroalkyl, heterohaloalkyl, cycloalkyl, cycloalkylalkyl-, heterocycloalkyl, heterocycloalkylalkyl-, aryl, arylalkyl-, heteroaryl, and heteroarylalkyl- of $R^1$ is unsubstituted or substituted with from 1 to 5 independently selected $R^{10}$ groups;

$R^2$ is selected from the group consisting of H, alkyl, halo, haloalkyl, aryl, arylalkyl-, heteroaryl, heteroarylalkyl-, cycloalkyl, cycloalkylalkyl-, cycloalkenyl, heterocycloalkyl, and heterocycloalkenyl, wherein each of said alkyl, haloalkyl, aryl, arylalkyl-, heteroaryl, heteroarylalkyl-, cycloalkyl, cycloalkylalkyl-, cycloalkenyl, heterocycloalkyl, and heterocycloalkenyl of $R^2$ is unsubstituted or substituted with from 1 to 5 independently selected $R^{10}$ groups;

$R^3$ is selected from the group consisting of alkyl, aryl, heteroaryl, cycloalkyl, cycloalkenyl, heterocycloalkyl, and heterocycloalkenyl, wherein each of said alkyl, aryl, heteroaryl, cycloalkyl, cycloalkenyl, heterocycloalkyl, and heterocycloalkenyl of $R^3$ is unsubstituted or substituted with from 1 to 5 independently selected $R^{10}$ groups;

ring A is selected from the group consisting of monocyclic aryl, monocyclic heteroaryl, monocyclic cycloalkyl, monocyclic cycloalkenyl, monocyclic heterocycloalkyl, monocyclic heterocycloalkenyl, and a multicyclic group;

each $R^4$ (when present) is independently selected from the group consisting of halo, —CN, —NO$_2$, —Si(R$^6$)$_3$, —P(O)(OR$^7$)$_2$, —P(O)(OR$^7$)(R$^7$), —N(R$^8$)$_2$, —NR$^8$C(O)R$^7$, —NR$^8$S(O)$_2$R$^7$, —NR$^8$C(O)N(R$^8$)$_2$, —NR$^8$C(O)OR$^7$, —C(O)R$^7$, —C(O)$_2$R$^7$, —C(O)N(R$^8$)$_2$, —S(O)R$^7$, —S(O)$_2$R$^7$, —S(O)$_2$N(R$^8$)$_2$, —OR$^7$, —SR$^7$, alkyl, haloalkyl, haloalkoxy, heteroalkyl, alkenyl, alkynyl, cycloalkyl, cycloalkylalkyl-, heterocycloalkyl, aryl, and heteroaryl, wherein each said alkyl, haloalkyl, haloalkoxy, heteroalkyl, alkenyl, alkynyl, cycloalkyl, cycloalkylalkyl-, heterocycloalkyl, aryl, and heteroaryl of $R^4$ (when present) is optionally independently unsubstituted or further substituted with one or more independently selected groups selected from the group consisting of lower alkyl, lower alkenyl, lower alkynyl, lower heteroalkyl, halo, —CN, —SF$_5$, —OSF$_5$, —NO$_2$, —N(R$^8$)$_2$, —OR$^7$, —C(O)N(R$^8$)$_2$, and cycloalkyl;

ring B is selected from the group consisting of monocyclic aryl, monocyclic heteroaryl, monocyclic cycloalkyl, monocyclic cycloalkenyl, monocyclic heterocycloalkyl, monocyclic heterocycloalkenyl, and a multicyclic group;

each $R^5$ (when present) is independently selected from the group consisting of halo, —CN, —NO$_2$, —Si(R$^6$)$_3$, —P(O)(OR$^7$)(R$^7$), —N(R$^8$)$_2$, —NR$^8$C(O)R$^7$, —NR$^8$S(O)$_2$R$^7$, —NR$^8$C(O)N(R$^8$)$_2$, —NR$^8$C(O)OR$^7$, —C(O)R$^7$, —C(O)$_2$R$^7$, —C(O)N(R$^8$)$_2$, —S(O)R$^7$, —S(O)$_2$R$^7$, —S(O)$_2$N(R$^8$)$_2$, —OR$^7$, —SR$^7$, alkyl, haloalkyl, haloalkoxy, heteroalkyl, alkenyl, alkynyl, cycloalkyl, cycloalkylalkyl-, heterocycloalkyl, aryl, and heteroaryl, wherein each said alkyl, haloalkyl, haloalkoxy, heteroalkyl, alkenyl, alkynyl, cycloalkyl, cycloalkylalkyl-, heterocycloalkyl, aryl, and heteroaryl of $R^5$ (when present) is optionally independently unsubstituted or further substituted with one or more independently selected groups selected from the group consisting of lower alkyl, lower alkenyl, lower alkynyl, lower heteroalkyl, halo, —CN, —SF$_5$, —OSF$_5$, —NO$_2$, —N(R$^8$)$_2$, —OR$^7$, —C(O)N(R$^8$)$_2$, and cycloalkyl;

each $R^6$ (when present) is independently selected from the group consisting of alkyl, aryl, arylalkyl-, haloalkyl, cycloalkyl, cycloalkylalkyl-, heteroaryl, and heteroarylalkyl-;

each $R^7$ (when present) is independently selected from the group consisting of H, alkyl, alkenyl, heteroalkyl, haloalkyl, aryl, arylalkyl-, heteroaryl, heteroarylalkyl-, cycloalkyl, cycloalkylalkyl-, heterocycloalkyl, and heterocycloalkylalkyl-;

each $R^8$ (when present) is independently selected from the group consisting of H, alkyl, alkenyl, heteroalkyl, haloalkyl, aryl, arylalkyl-, heteroaryl, heteroarylalkyl-, cycloalkyl, cycloalkylalkyl-, heterocycloalkyl, and heterocycloalkylalkyl-;

$R^{8A}$ is selected from the group consisting of alkyl, alkenyl, cycloalkyl, cycloalkylalkyl, heterocycloalkyl, heterocycloalkylalkyl, aryl, arylalkyl, heteroaryl, heteroarylalkyl, arylcycloalkyl, OR$^7$, —CN, —C(O)R$^7$, —C(O)OR$^7$, —S(O)$_2$R$^7$, —C(O)N(R$^8$)$_2$, —S(O)$_2$N(R$^8$)$_2$, —S(O)$_2$N(R$^8$)$_2$, —NO$_2$, and —N(R$^8$)$_2$;

each $R^{10}$ (when present) is independently selected from the group consisting of halo, —CN, —NO$_2$, —Si(R$^6$)$_3$, —P(O)(OR$^7$)$_2$, —P(O)(OR$^7$)(R$^7$), —N(R$^8$)$_2$, —NR$^8$C(O)R$^7$, —NR$^8$S(O)$_2$R$^7$, —NR$^8$C(O)N(R$^8$)$_2$, —NR$^8$C(O)OR$^7$, —C(O)R$^7$, —C(O)$_2$R$^7$, —C(O)N(R$^8$)$_2$, —S(O)R$^7$, —S(O)$_2$R$^7$, —S(O)$_2$N(R$^8$)$_2$, —OR$^7$, —SR$^7$, alkyl, haloalkyl, haloalkoxy, heteroalkyl, alkenyl, alkynyl, cycloalkyl, heterocycloalkyl, aryl, and heteroaryl, wherein each said alkyl, haloalkyl, haloalkoxy, heteroalkyl, alkenyl, alkynyl, cycloalkyl, heterocycloalkyl, aryl, and heteroaryl of $R^{10}$ (when present) is optionally independently unsubstituted or further substituted with one or more independently selected groups selected from the group consisting of lower alkyl, lower alkenyl, lower alkynyl, lower heteroalkyl, halo, —CN, —NO$_2$, —N(R$^8$)$_2$, —OR$^7$, —C(O)N(R$^8$)$_2$, and cycloalkyl; and each $R^{11}$ is independently selected from the group consisting of —SF$_5$ and —OSF$_5$.

3. A compound of claim 1, or a pharmaceutically acceptable salt thereof, wherein:

$R^1$ is selected from the group consisting of H, lower alkyl, and cyclopropyl.

4. A compound of claim 1, or a pharmaceutically acceptable salt thereof, wherein:

$R^2$ is H.

5. A compound of claim 1, or a pharmaceutically acceptable salt thereof, wherein:

-L$_2$- is a bond or a -alkyl- group; and $R^3$ is selected from the group consisting H, alkyl, haloalkyl, heteroalkyl, cycloalkyl, and cycloalkylalkyl-.

6. A compound of claim 1, or a pharmaceutically acceptable salt thereof, said compound having a structural Formula (II):

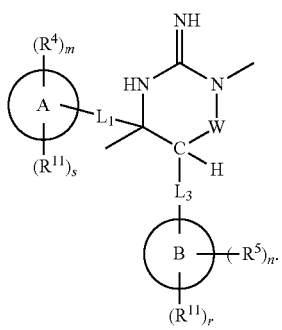

(II)

7. A compound of claim 6, or a pharmaceutically acceptable salt thereof, wherein:
-L$_1$- is a bond or a divalent -alkyl- group;
m is 0 or more;
s is 0, 1, or 2;
ring A is selected from the group consisting of phenyl, pyridyl, pyrazinyl, pyrazolyl, furanyl, thienyl, pyrimidinyl, pyridazinyl, thiazolyl, and oxazolyl;
each R$^4$ (when present) is independently selected from the group consisting of halo, —CN, —NO$_2$, —N(R$^8$)$_2$, —NR$^8$C(O)R$^7$, —C(O)N(R$^8$)$_2$, —OR$^7$, alkyl, haloalkyl, heteroalkyl, and alkynyl;
-L$_3$- is a bond or a divalent —CH$_2$— group;
n is 0 or more;
r is 0, 1, or 2;
ring B is selected from the group consisting of phenyl, benzoxazolyl, benzofuranyl, benzimidazolyl, benzisoxazolyl, pyridyl, pyrazinyl, furanyl, thienyl, pyrimidinyl, pyridazinyl, thiazolyl, oxazolyl, quinolinyl, isoquinolinyl, dihydroquinolinyl, naphthyl, benzothienyl, benzothiazolyl, indazolyl, and indolyl;
each R$^5$ (when present) is independently selected from the group consisting of halo, —CN, —N(R$^8$)$_2$, —NR$^8$C(O)R$^7$, —NR$^8$S(O)$_2$R$^7$, —C(O)R$^7$, —S(O)R$^7$, S(O)$_2$R$^7$, —OR$^7$, —SR$^7$, alkyl, haloalkyl, heteroalkyl, —O-heteroalkyl, alkenyl, cycloalkyl, heterocycloalkyl, aryl, and monocyclic heteroaryl,
wherein each said alkyl, said alkenyl, said alkenyl, said cycloalkyl, said heterocycloalkyl, said aryl, and said monocyclic heteroaryl of R$^5$ (when present) is optionally and independently further substituted with one or more groups independently selected from the group consisting of halo, lower alkyl, lower alkenyl, lower alkynyl, lower heteroalkyl, —CN, —NO$_2$, —N(R$^8$)$_2$, and —OH;
with the provisos that
(i) the sum of m and s is the maximum number of substitutable hydrogen atoms on ring A,
(ii) the sum of n and r is the maximum number of substitutable hydrogen atoms on ring B, and
(iii) the sum of r and s is 1 or 2.

8. A compound of claim 6, or a pharmaceutically acceptable salt thereof, wherein:
-L$_1$- is a bond or a divalent —CH$_2$- group;
ring A is selected from the group consisting of phenyl and thienyl;
wherein, when ring. A is phenyl, the sum of m and s is 0 to 5, and
when ring A is thienyl, the sum of m and s is 0 to 3;
each R$^4$ (when present) is independently selected from the group consisting of halo, —CN, —NO$_2$, —N(R$^8$)$_2$, —NR$^8$C(O)R$^7$, —C(O)N(R$^8$)$_2$, OR$^7$, alkyl, haloalkyl, heteroalkyl, and alkynyl;

-L$_3$- is a bond or a diavalent -alkyl- group;
ring B is selected from the group consisting of phenyl, pyridyl, thienyl, naphthyl, quinolinyl, isoquinolinyl, and benzothienyl;
n is 0 or more;
r is 0, 1, or 2, with the provisos that (i) the sum of n and r is the maximum number of substitutable hydrogen atoms on ring B, and (ii) the sum of r and s is 1 or 2;
each R$^5$ (when present) is independently selected from the group consisting of halo, —CN, —N(R$^8$)$_2$, —NR$^8$C(O)R$^7$, —NR$^8$S(O)$_2$R$^7$ —C(O)R$^7$, —S(O)R$^7$, —S(O)$_2$R$^7$, —SR', alkyl, haloalkyl, heteroalkyl, —O-heteroalkyl, alkenyl, alkynyl, cyclopropyl, cyclobutyl, cyclopentyl, cyclohexyl, phenyl, pyridyl, furanyl, thienyl, pyridazinyl, oxazolyl, isoxazolyl, oxetanyl, and pyrrolyl,
wherein each said alkyl, -alkoxy, haloalkyl, heteroalkyl, —O-heteroalkyl, alkynyl, cyclopropyl, cyclobutyl, cyclopentyl, cyclohexyl, phenyl, pyridyl, furanyl, thienyl, pyridazinyl, oxazolyl, isoxazolyl, oxetanyl, and pyrrolyl of R$^5$ (when present) is optionally and independently further substituted with one or more groups independently selected from the group consisting of halo, lower alkyl, lower alkenyl, lower alkynyl, lower heteroalkyl, —CN, —NO$_2$, —N(R$^8$)$_2$, and —OH;
and each R$^7$ and each R$^8$ (when present) is independently selected from the group consisting of H and lower alkyl.

9. A compound of claim 6, or a pharmaceutically acceptable salt thereof, wherein:
-L1- is a bond or a divalent —CH$_2$- group;
the moiety,

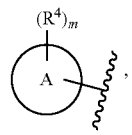

is selected from the group consisting of

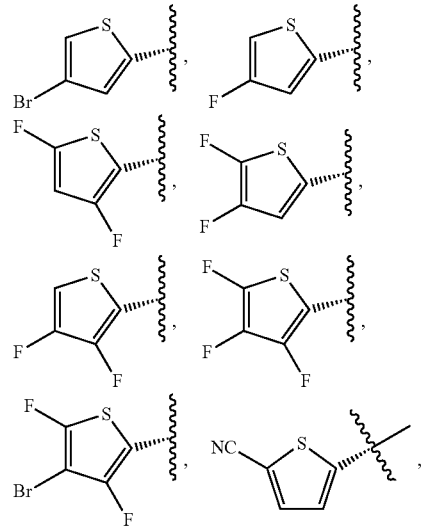

-continued

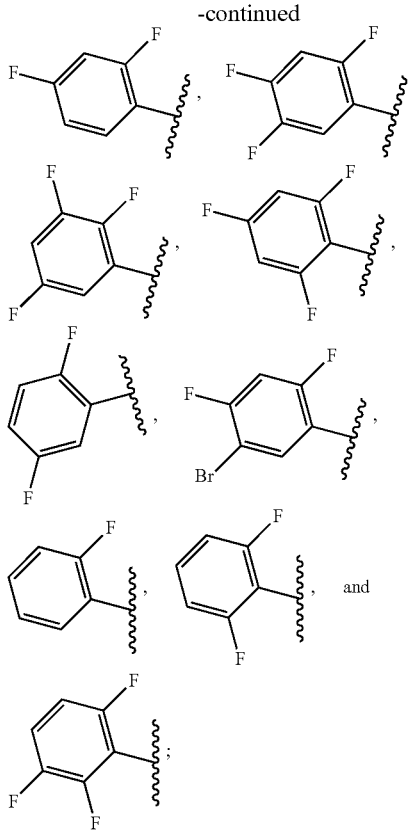

n is 0, 1, 2, or 3;

ring B is selected from the group consisting of phenyl, pyridyl, thienyl, naphthyl, quinolinyl, isoquinolinyl, and benzothienyl; and each $R^5$ (when present) is independently selected from the group consisting of halo, —CN, —SF$_5$, lower alkyl, lower alkenyl, lower haloalkyl, —C(O)—Cyclopropyl, oxetanyl, lower alkyl—Substituted oxetanyl, cyclopropyl, lower heteroalkyl substituted cyclopropyl, lower alkyl—CN, lower heteroalkyl, and phenyl.

10. A compound of claim 6, or a pharmaceutically acceptable salt thereof, wherein:

-L$_1$- is a bond or a divalent —CH$_2$- group;

s is 0;

the moiety,

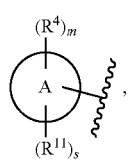

is selected from the group consisting of

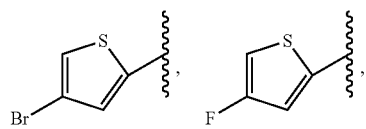

-continued

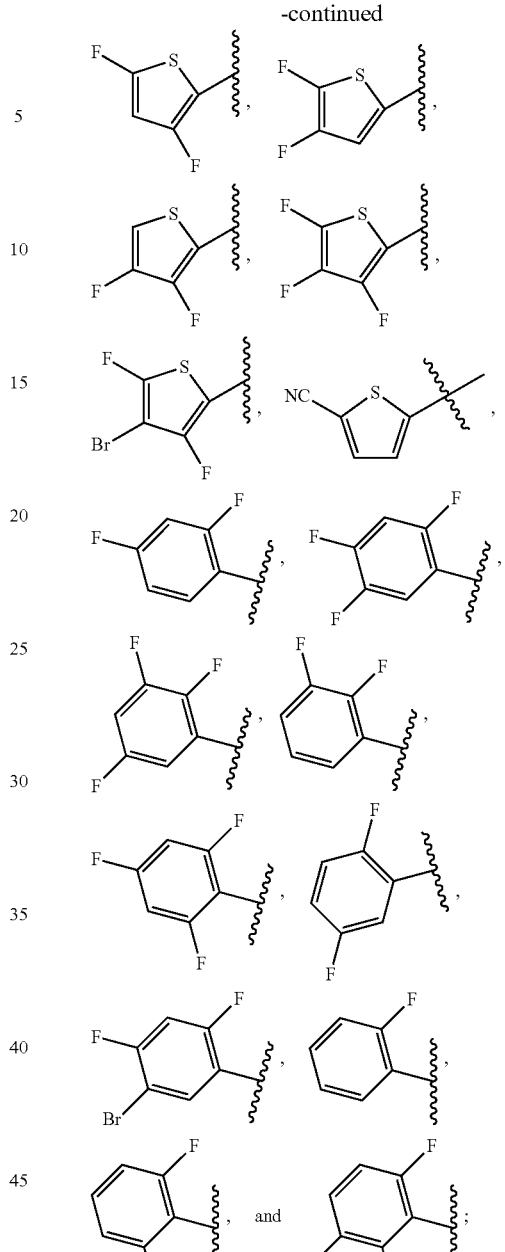

n is 0, 1, 2, or 3, r is 1 or 2;

ring B is selected from the group consisting of phenyl, pyridyl, thienyl, naphthyl, quinolinyl, isoquinolinyl, and benzothienyl; and each $R^5$ (when present) is independently selected from the group consisting of halo, —CN, lower alkyl, lower alkenyl, lower haloalkyl, —C(O)-Cyclopropyl, oxetanyl, lower alkyl-Substituted oxetanyl, cyclopropyl, lower heteroalkyl substituted cyclopropyl, lower alkyl-CN, lower heteroalkyl, and phenyl.

11. A compound of claim 6, or a pharmaceutically acceptable salt thereof, wherein:

-L$_1$- is a bond or a divalent —CH$_2$- group;

s is 0;

the moiety,

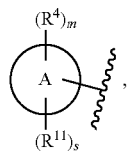

is selected from the group consisting of

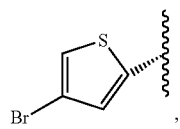 , 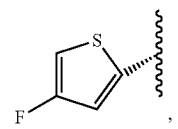 ,

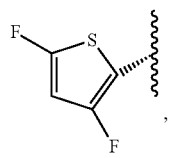 , 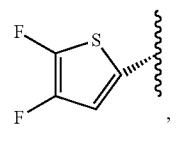 ,

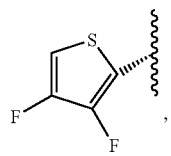 , 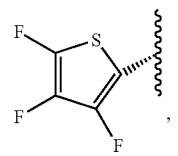 ,

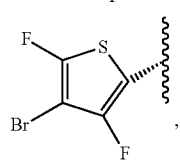 , 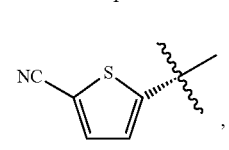 ,

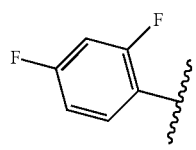 , 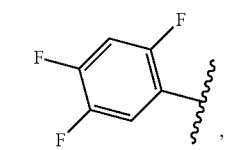 ,

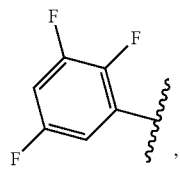 , 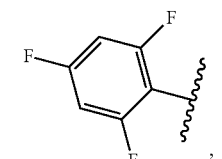 ,

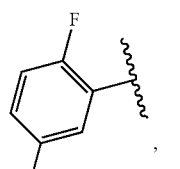 , 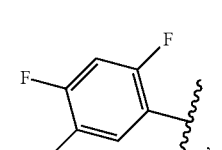 ,

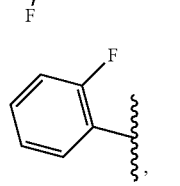 , 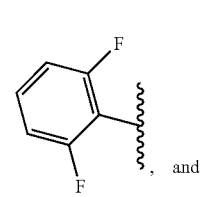 , and

-continued

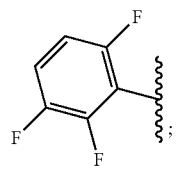 ;

-$L_3$- is a bond or a divalent —$CH_2$— group;

ring B is phenyl;

n is 0;

r is 1; and and the moiety

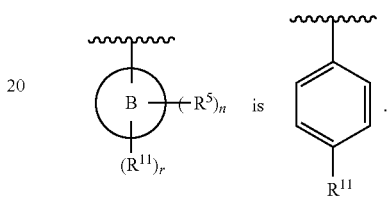

12. A compound of claim 11, or a pharmaceutically acceptable salt thereof, wherein:

$R^{11}$ is —$SF_5$.

13. A compound of claim 11, or a pharmaceutically acceptable salt thereof, wherein:

$R^{11}$ is —$OSF_5$.

14. A compound, or a pharmaceutically acceptable salt thereof, said compound being selected from the group consisting of:

| Ex. # | Structure |
|---|---|
| 1 | 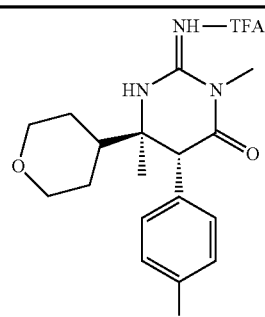 |
| 2 | 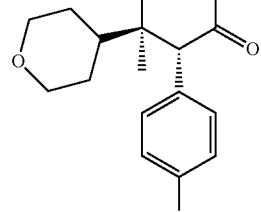 |

-continued

| Ex. # | Structure |
|---|---|
| 3 | 2,4-difluorophenyl / methyl / 4-SF5-phenyl dihydropyrimidinone with NH—TFA |
| 4 | 2,5-difluorophenyl / methyl / 4-SF5-phenyl dihydropyrimidinone with NH—TFA |
| 5 | 2,3-difluorophenyl / methyl / 4-SF5-phenyl dihydropyrimidinone with NH—TFA |
| 6 | 2,4,6-trifluorophenyl / methyl / 4-SF5-phenyl dihydropyrimidinone with NH—TFA |

-continued

| Ex. # | Structure |
|---|---|
| 7 | 2,4,5-trifluorophenyl / methyl / 4-SF5-phenyl dihydropyrimidinone with NH—TFA |
| 8 | 2,4,6-trifluorophenyl / methyl / 3-SF5-phenyl dihydropyrimidinone with NH—TFA |
| 9 | 2,4,6-trifluorophenyl / methyl / 4-SF5-phenyl dihydropyrimidinone with NH—TFA |

15. A pharmaceutical composition comprising at least one compound of any one of claims 1-14, or a pharmaceutically acceptable salt thereoof, and a pharmaceutically acceptable carrier or diluent.

16. A pharmaceutical composition of claim 15, wherein said at least one additional therapeutic agent is at least one agent selected from:

$m_1$ agonists; $m_2$ antagonists; cholinesterase inhibitors; galantamine; rivastigimine; N-methyl-D-aspartate receptor antagonists; combinations of cholinesterase inhibitors and N-methyl-D-aspartate receptor antagonists; gamma secretase modulators; gamma secretase inhibitors; non—Steroidal anti-inflammatory agents; anti-inflammatory agents that can reduce neuroinflammation; anti-amyloid antibodies; vitamin E; nicotinic acetylcholine receptor agonists; CB1 receptor inverse agonists; CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors; Tau aggregation inhibitors; RAGE inhibitors; anti-Abeta vaccine; APP ligands; agents that upregulate insulin, cholesterol lowering agents; cholesterol absorption inhibitors; combinations of HMG-CoA reductase inhibitors and cholesterol absorption inhibitors; fibrates; combinations of fibrates and cholesterol lowering agents and/or cholesterol absorption inhibitors; nicotinic receptor agonists; niacin; combinations of niacin and cholesterol absorption inhibitors and/or cholesterol lowering agents; LXR agonists; LRP mimics; H3 receptor antagonists; histone deacetylase inhibitors; hsp90 inhibitors; 5-HT4 agonists; 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux; Metal—Protein attenuating compound; GPR3 modulators; and antihistamines.

* * * * *